(12) United States Patent
Merrell et al.

(10) Patent No.: US 11,420,010 B1
(45) Date of Patent: Aug. 23, 2022

(54) BAG AND VALVE FOR ADVANCED RESPIRATORY SUPPORT

(71) Applicant: Compact Medical Solutions LLC, Indianapolis, IN (US)

(72) Inventors: Jonathan Merrell, Indianapolis, IN (US); Adam Scott, Anderson, IN (US); Jacob Flagle, New Palestine, IN (US); Daniel Lane, Sunberry, OH (US)

(73) Assignee: Compact Medical Inc., Indianapolis, IN (US)

( * ) Notice: Subject to any disclaimer, the term of this patent is extended or adjusted under 35 U.S.C. 154(b) by 0 days.

(21) Appl. No.: 17/537,169

(22) Filed: Nov. 29, 2021

Related U.S. Application Data

(60) Provisional application No. 63/251,373, filed on Oct. 1, 2021.

(51) Int. Cl.
| | |
|---|---|
| *A61M 16/00* | (2006.01) |
| *A61M 16/20* | (2006.01) |
| *A61M 16/10* | (2006.01) |

(52) U.S. Cl.
CPC ...... *A61M 16/208* (2013.01); *A61M 16/0078* (2013.01); *A61M 16/1055* (2013.01);
(Continued)

(58) Field of Classification Search
CPC ............ A61M 16/201; A61M 16/0078; A61M 16/209; A61M 16/006; A61M 16/0084;
(Continued)

(56) References Cited

U.S. PATENT DOCUMENTS

| 3,063,620 A | 11/1962 | Black |
| 3,420,225 A | 1/1969 | Holden et al. |

(Continued)

FOREIGN PATENT DOCUMENTS

| CN | 108654014 A | 10/2018 |
| CN | 208287315 U | 12/2018 |

(Continued)

OTHER PUBLICATIONS

Advanced Emergency Nursing Journal, "Early Modern Resuscitators", first available May 3, 2014. (https://journals.lww.com/aenjournal/blog/aenj-blog/Lists/Posts/Post.aspx? I 0=40) (Year: 2014).

(Continued)

*Primary Examiner* — Margaret M Luarca
(74) *Attorney, Agent, or Firm* — Merchant & Gould P.C.

(57) ABSTRACT

A respiratory device provides respiratory support to a patient. The respiratory device includes an expandable bag and a rigid valve housing. The expandable bag has an air inlet valve as well as a first and second sides that are bounded, respectively, by first and second rigid side panels. Each of the first and second rigid side panels includes a biasing member projection. The rigid valve housing is in fluid communication with the expandable bag. The rigid valve housing includes an adjustable tidal volume control device that interfaces with the biasing member projection of each of the first and second rigid side panels to set one of a plurality of predetermined tidal volumes for the expandable bag in an uncompressed or compressed configuration. The rigid valve housing additionally includes a patient breathing interface connection member.

21 Claims, 59 Drawing Sheets

(52) U.S. Cl.
CPC ... *A61M 16/209* (2014.02); *A61M 2205/3344* (2013.01); *A61M 2205/3379* (2013.01); *A61M 2205/583* (2013.01); *A61M 2205/586* (2013.01); *A61M 2205/7509* (2013.01); *A61M 2230/43* (2013.01)

(58) Field of Classification Search
CPC . A61M 16/0081; A61M 16/208; A61M 16/20
See application file for complete search history.

(56) References Cited

U.S. PATENT DOCUMENTS

| | | | |
|---|---|---|---|
| 3,473,529 A | 10/1969 | Wallace | |
| 4,060,077 A | 11/1977 | Friedman | |
| 4,349,015 A | 9/1982 | Alferness | |
| 4,498,472 A | 2/1985 | Tanaka | |
| 4,501,271 A | 2/1985 | Clifton et al. | |
| 4,539,985 A | 9/1985 | Magrath | |
| 4,821,713 A | 4/1989 | Bauman | |
| 4,870,962 A | 10/1989 | Sitnik | |
| 4,898,166 A | 2/1990 | Rose et al. | |
| D309,025 S | 7/1990 | Beacham | |
| 5,109,840 A | 5/1992 | Daleiden | |
| 5,163,424 A | 11/1992 | Kohnke | |
| 5,301,667 A | 4/1994 | McGrail et al. | |
| 5,558,371 A | 9/1996 | Lordo | |
| 5,762,063 A | 6/1998 | Coates et al. | |
| 5,787,880 A | 8/1998 | Swanson et al. | |
| 5,857,460 A | 1/1999 | Popitz | |
| 6,283,120 B1 | 9/2001 | Kellon | |
| 6,792,947 B1 | 9/2004 | Bowden | |
| 7,051,596 B1 | 5/2006 | Lau et al. | |
| 7,172,557 B1 | 2/2007 | Parker | |
| 7,537,008 B2 | 5/2009 | Halpern | |
| D653,760 S | 2/2012 | Johnson | |
| 8,443,803 B2 | 5/2013 | Reisman | |
| 8,844,521 B2 | 9/2014 | McCarthy | |
| 8,936,024 B2 | 1/2015 | Pearce | |
| D809,130 S | 1/2018 | Yang | |
| 9,861,775 B1* | 1/2018 | Farmer | A61M 16/0075 |
| D865,300 S | 10/2019 | Fallgatter | |
| 10,525,223 B2 | 1/2020 | Merrell et al. | |
| 10,960,172 B2 | 3/2021 | Merrell et al. | |
| 11,179,529 B2 | 11/2021 | Merrell et al. | |
| 2002/0029779 A1 | 3/2002 | Schmidt et al. | |
| 2002/0117173 A1 | 8/2002 | Lynn et al. | |
| 2006/0180146 A1 | 8/2006 | Thompson et al. | |
| 2006/0266358 A1 | 11/2006 | Hoogland | |
| 2010/0236557 A1 | 9/2010 | Reisman | |
| 2010/0263670 A1 | 10/2010 | Pearce | |
| 2011/0120472 A1 | 5/2011 | Lee et al. | |
| 2012/0012111 A1* | 1/2012 | Howe, Jr. | A61M 16/1055 128/205.12 |
| 2013/0092166 A1 | 4/2013 | Pearce | |
| 2013/0118498 A1 | 5/2013 | Robitaille et al. | |
| 2013/0192601 A1 | 8/2013 | Reischl et al. | |
| 2014/0107518 A1 | 4/2014 | Korneff | |
| 2014/0318544 A1 | 10/2014 | Murphy et al. | |
| 2015/0202429 A1 | 7/2015 | Fritzsche | |
| 2016/0256661 A1 | 9/2016 | Battersby et al. | |
| 2016/0263339 A1 | 9/2016 | Greenberg | |
| 2016/0367781 A1* | 12/2016 | McCollum | A61M 16/201 |
| 2017/0157348 A1 | 6/2017 | Gillespie et al. | |
| 2018/0021533 A1 | 1/2018 | Gausche-Hill et al. | |
| 2018/0036531 A1 | 2/2018 | Schwarz et al. | |
| 2018/0272096 A1 | 9/2018 | Rubin | |
| 2019/0366029 A1* | 12/2019 | Prabhudesai | A61M 16/208 |
| 2020/0078550 A1* | 3/2020 | Islava | A61M 16/0084 |
| 2020/0345967 A1 | 11/2020 | Merrell et al. | |
| 2021/0213219 A1 | 7/2021 | Merrell et al. | |

FOREIGN PATENT DOCUMENTS

| | | |
|---|---|---|
| EP | 0 421 007 A1 | 4/1991 |
| IN | 328653-001-0001 | 2/2021 |
| WO | 2013112914 A2 | 8/2013 |
| WO | 2014140776 A1 | 9/2014 |
| WO | 2016130867 A1 | 8/2016 |
| WO | 2017163131 A1 | 9/2017 |
| WO | 2018/035137 A1 | 2/2018 |

OTHER PUBLICATIONS

Amazon, "Intex Bellows Foot Pump Series", first available Jul. 14, 2020. (https://www.amazon.com/Intex-Bellows-Foot-Pump-Series/dp/B08CXYYMZQ) (Year: 2020).

Amazon, "Medline Industries CPRM2216 Pediatric Manual Resuscitator", first available Mar. 18, 2016. (https://www.amazon.com/Medline-Industries-CPRM2216-Pediatric-Resuscitator/dp/B00KG88RRE/ref=zg_bs_8297519011 _9?_encoding=UTF8 &psc= 1 & refRI D=2V1 RBK6DKV2EB209G5N2) (Year: 2016).

Amazon, "PVC Adult Tool Bag Resuscitator Bag for First Aid Training", first available Mar. 30, 2020. (https://www.amazon.com/dp/ B0885ZT812/ref=cm_sw _em_r _mt_dp_7M BI Fb6F872G3) (Year: 2020).

International Search Report and Written Opinion for PCT Application No. PCT/US2019/062005, dated Feb. 28, 2020.

Design U.S. Appl. No. 29/690,042, filed May 3, 2019.

India Serial No. of registration 328653-001-0001, "Respiratory Bag," published Feb. 26, 2021, 1 page.

International Search Report and Written Opinion for PCT Application No. PCT/US2021/024260, dated Dec. 2, 2021, 18 pages.

International Search Report and Written Opinion for PCT Application No. PCT/US2021/051149, dated Mar. 18, 2022, 16 pages.

* cited by examiner

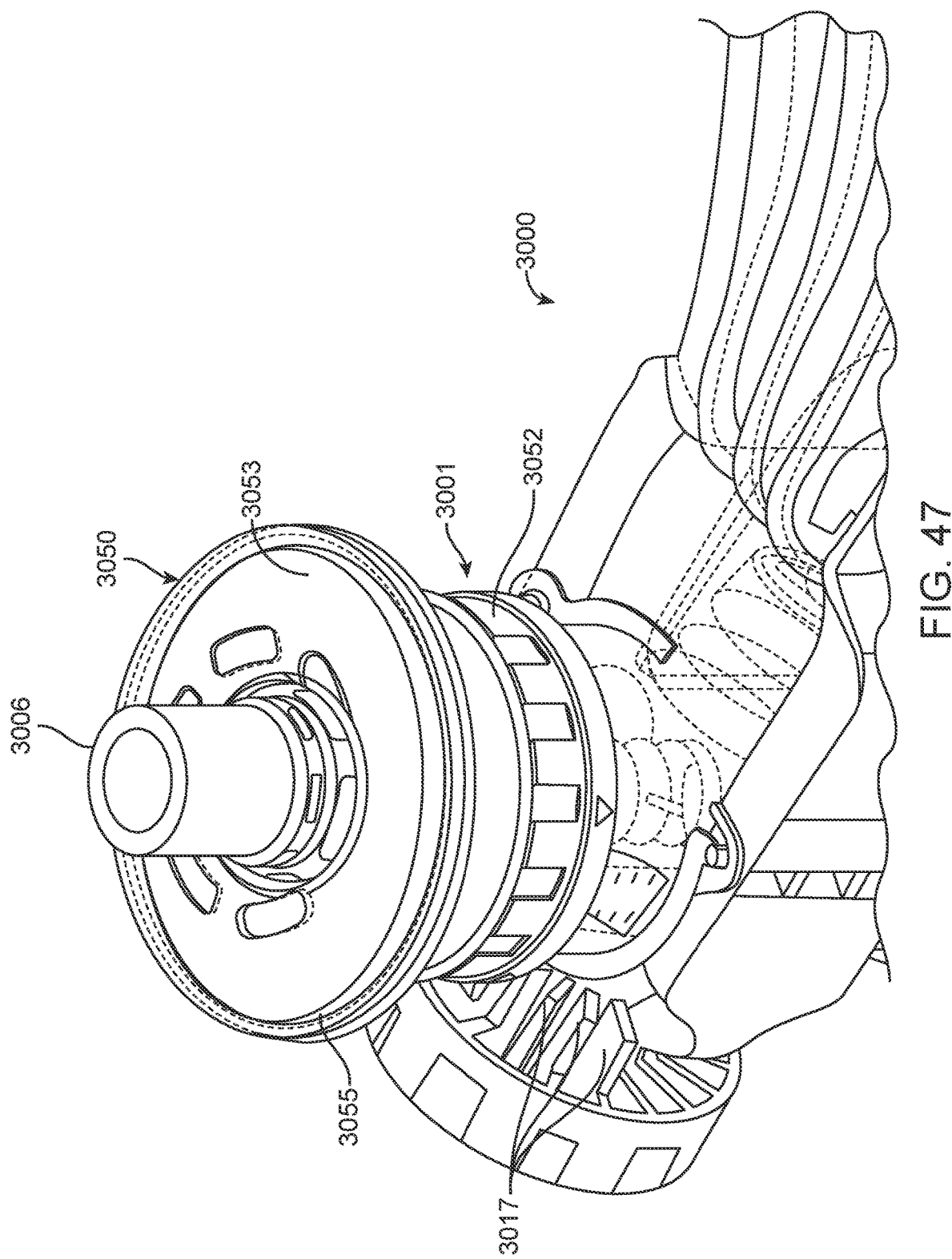

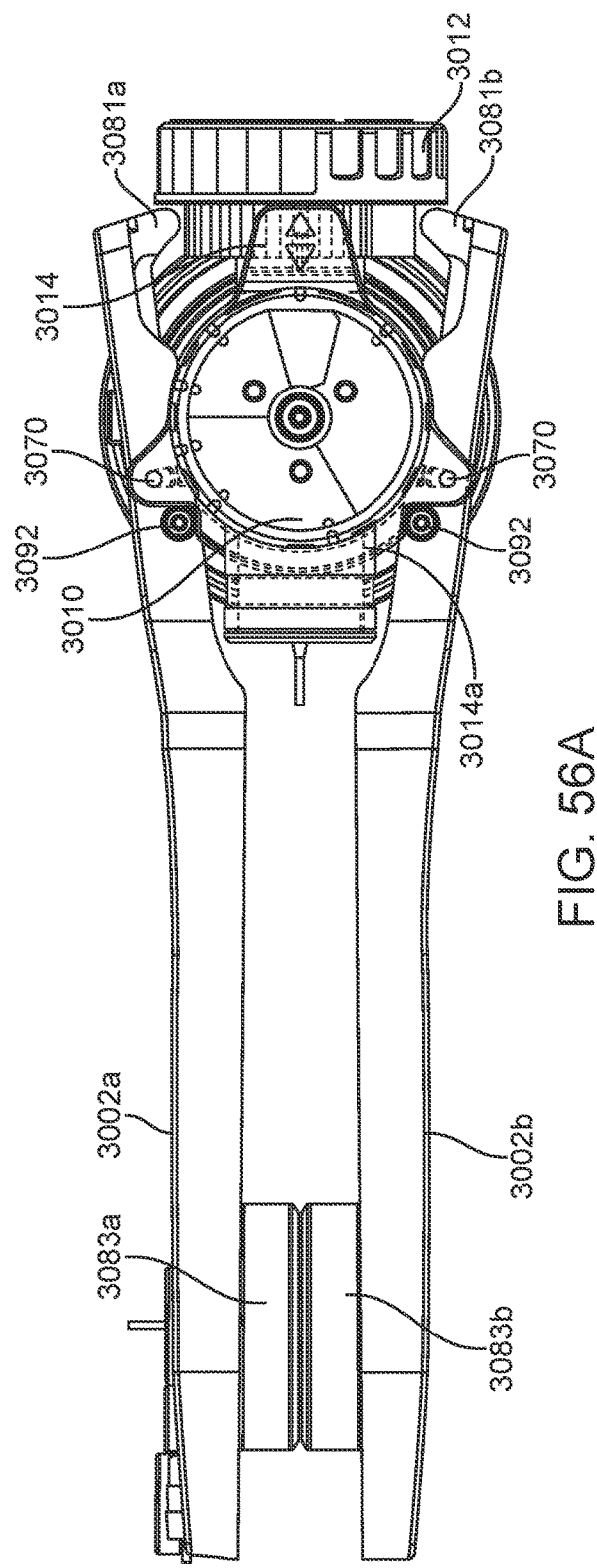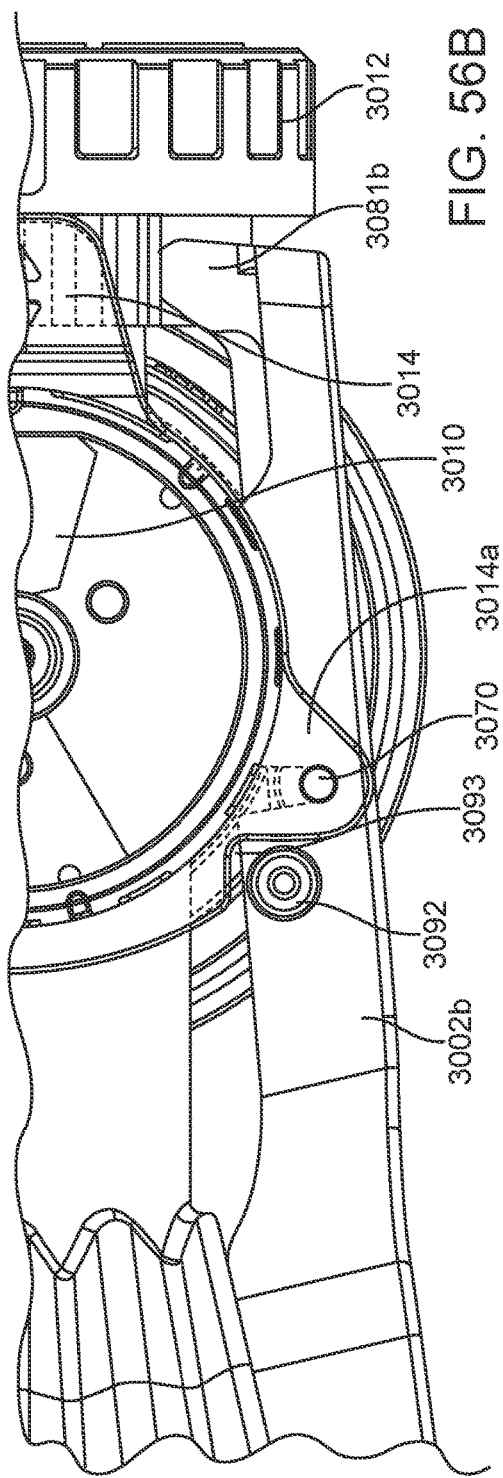

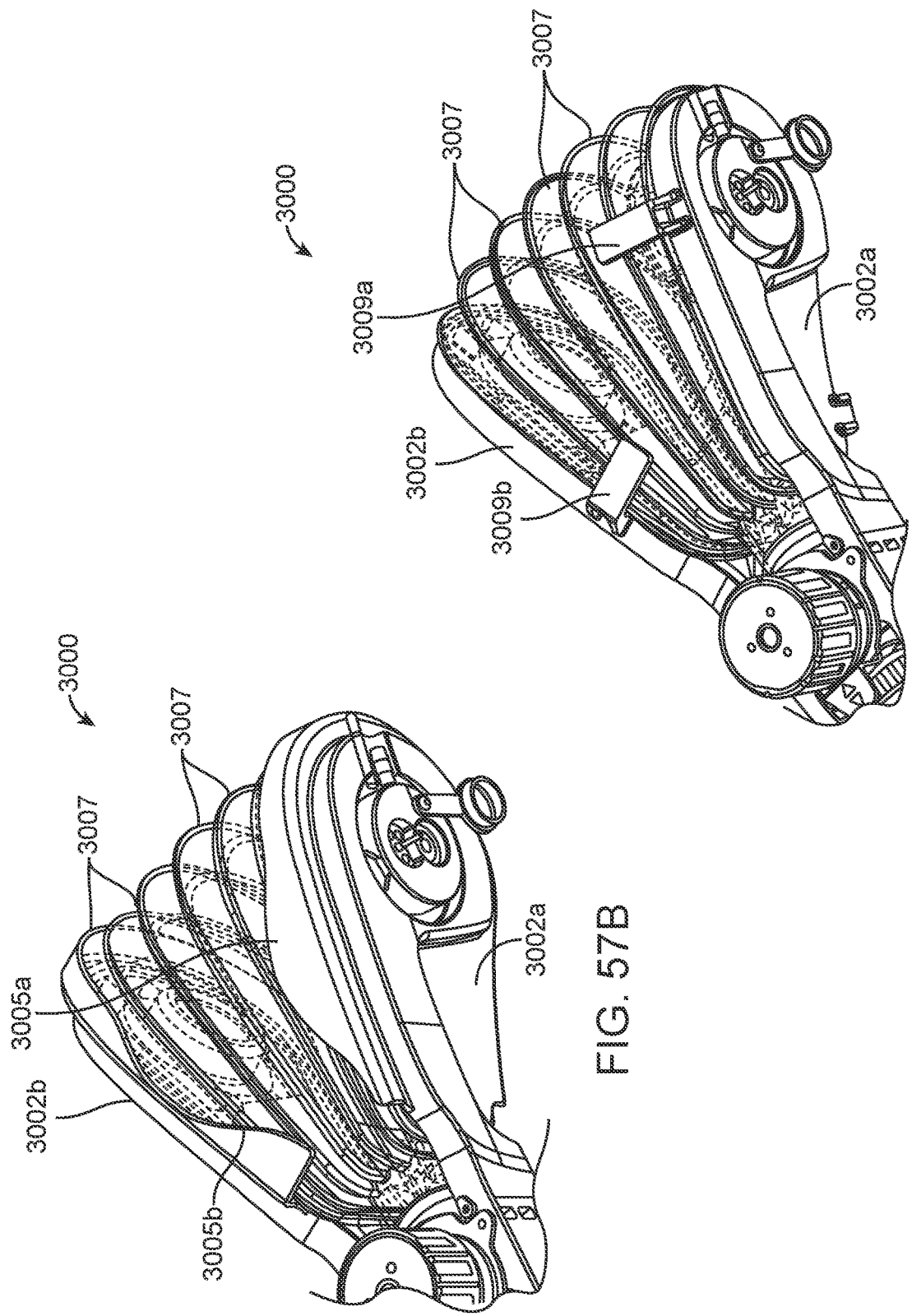

BAG AND VALVE FOR ADVANCED RESPIRATORY SUPPORT

CROSS-REFERENCE TO RELATED APPLICATIONS

This application claims the benefit of U.S. Provisional Patent Application No. 63/251,373, filed Oct. 1, 2021, entitled, "BAG AND VALVE FOR ADVANCED RESPIRATORY SUPPORT." The disclosure of this priority application is hereby incorporated by reference in its entirety into the present application.

TECHNICAL FIELD

The present disclosure relates generally to a bag-valve-mask or resuscitator used to ventilate patients in a field setting.

BACKGROUND

A manual resuscitator, or a bag-valve-mask (BVM), is a device used to temporarily push air into the lungs of a patient who is unconscious or otherwise unable to breathe on their own. These devices are found in hospitals and in ambulances throughout the country and in most developed parts of the world.

BVMs have existed for many years. Numerous modifications and enhancements have been made to BVMs over the years, these include enhanced 2-way valves, the addition of a high-pressure relieving "pop-off" valve, and the attachment of an oxygen reservoir to the bag to increase the percent of oxygen content of air flowing into the self-inflating bag portion of the device.

Self-inflating or self-expanding bags are bulky. They typically hold over a liter of air (in an adult model) even when not in use. Two-way valves are also bulky, and make use of a rigid plastic construct that is most commonly shaped in a 90-degree angle. The mask is similarly bulky and typically employs a rigid plastic triangular-shaped device with a soft rubber balloon about a perimeter that interfaces with and forms a seal around the mouth and nose of a victim. Each of these components is bulky in its own right and together, these form a device that is too large and obtuse to be carried in public by individuals who are trained to use them. Thus, when an emergency arises in most non-clinical settings, a BVM is not typically available until after an ambulance has arrived.

Efforts have been made in the past to reduce the overall space occupied by these devices. This includes an entirely collapsible bag with a flexible hollow body that can be stowed into a container. In attempts to make the device smaller, thinner materials have been used. This results in bag-valve-masks that are suitable for one-time use, due to the device losing functionality after its use. Therefore, BVMs are typically only available in a hospital setting or similar clinical location.

In addition to their bulk, traditional BVMs are prone to cause hyperventilation. A condition in which a patient is given too much air. This can result in death. Traditional BVMs cause hyperventilation because they inflate too rapidly, leading lifesavers to give breaths more frequently than is recommended.

Finally, traditional BVMs are only capable of delivering a fixed tidal volume with or without a fixed pressure relief point depending on the size of the BVM (adult, pediatric, or neonatal).

SUMMARY

In general terms, this disclosure is directed towards a respiratory device having an expandable bag with a valve housing and a patient breathing interface. The respiratory device allows a user to provide respiratory support to a patient.

In certain aspects the present disclosure is directed to a respiratory device is includes an expandable bag and a rigid valve housing. The expandable bag has an air inlet valve as well as a first and second sides that are bounded, respectively, by first and second rigid side panels. Each of the first and second rigid side panels includes a biasing member projection. The rigid valve housing is in fluid communication with the expandable bag. The rigid valve housing includes an adjustable tidal volume control device that interfaces with the biasing member projection of each of the first and second rigid side panels to set one of a plurality of predetermined tidal volumes for the expandable bag in an uncompressed or compressed configuration. The rigid valve housing additionally includes a patient breather interface connection member that is couplable.

In certain aspects, the adjustable tidal volume control presents a first surface of varying depth and an opposing second surface of corresponding varying depth to respectively interface with the biasing member projection of each of the first and second rigid side panels to set one of a plurality of predetermined tidal volumes. In certain aspects the adjustable tidal volume control is mounted to a body portion of the rigid valve housing.

In certain aspects, the respiratory device additionally includes an adjustable Peak Inspiratory Pressure (PIP) mechanism that is maintained within the body portion and an adjustable PIP control device that is independently mounted to the body portion. The adjustable PIP control device adjusts the PIP mechanism to provide one of a plurality predetermined peak inspiratory pressure values.

In certain aspects, the respiratory device additionally or alternatively includes a two-way valve maintained within the body portion of the rigid valve housing that allows air to move from the expandable bag in first direction through a first portion of the two-way valve and that directs an in an opposing direction through a second portion of the two-way valve to create Positive End Expiratory Pressure (PEEP).

In certain aspects, the adjustable tidal volume control device is labeled with indicia that corresponds to established standards used to determine volumes of air needed for a patient based on the length, weight, and/or age. In certain aspects, the adjustable PIP control device is labeled with indicia that corresponds to established PIP standards.

In certain aspects, the respiratory device further includes first and second hinge pins that hingedly secure the first and second rigid side panels, respectively, to the rigid valve housing. In certain aspects, the biasing member projection of each of the first and second rigid side panels is positioned forward of the respective hinge pin.

In certain aspects, each of the first and second rigid side panels includes an expandable bag distortion prevent feature comprising at least one of: (a) contoured edges; and (b) tabs. In certain aspects, each of the first and second rigid side panels includes a stop feature that prevents over-compression of the respiratory device. The stop feature comprises at least one of: (a) a projecting external stop that interfaces with a ring positioned about the rigid valve housing; (b) an internal stop extending from an interior surface of the respective rigid side panel, the internal stop of the first and second rigid side panel opposing one another and contacting one another upon full compression of the respiratory device; (c) a contour edge extending outward from an upper and/or lower surface of the respective rigid side panel, the contour edge of the first and second rigid side panel opposing one another and contacting one another upon full compression of the respiratory device; and (d) a tab extending outward from an upper and/or lower surface of the respective rigid side panel, a portion of the tab of a respective one of the rigid side panels interfacing with a portion of the other of the rigid side panels.

In certain aspects, the respiratory device additionally includes a compressed gas inlet port in fluid communication with the expandable bag. In certain aspects, the respiratory device includes an inflation adjustment dial to adjust a size of an aperture through which a compressed gas and/or ambient air communicates with the expandable bag. In certain aspects, the respiratory device additionally includes an exhaust valve and a blocking cap; the blocking cap is moveable between a position where the exhaust valve is blocked and a position where the exhaust valve is unblocked. In certain aspects, the respiratory device provides Continuous Positive Airway Pressure (CPAP) upon both: (a) compressed gas being supplied to the respiratory device via the compressed gas inlet port; and (b) the adjustable PEEP control device being engaged.

In certain aspects, each of the first and second rigid side panels includes a textured ergonomic recess for single-handed operation of the respiratory device.

In certain aspects, the respiratory device further includes a filter body secured to the rigid valve housing with the filter body including a bio/viral filter that filters patient exhalations exiting the respiratory device. In certain aspects, the filter body is secured to at least one of: (a) the rigid valve housing; and (b) the PEEP control device. In certain aspects, the filter body includes an exhalation port that is couplable to an end-tidal $CO_2$ monitor. In certain aspects the bio/viral filter generates its own PEEP. In certain aspects, the respiratory device includes a seal intermediate the main body of the rigid valve housing and the adjustable PEEP control device.

In certain aspects, the respiratory device further includes a removable PEEP lock that is removably secured to the main body of the rigid valve housing. The PEEP lock maintains a PEEP of zero and prevents adjustment of the PEEP control device.

In certain aspects, the present disclosure is directed to a valve housing portion for use in providing respiratory support to a patient. The valve housing portion includes a body portion that is connectable to a patient breathing interface as well as an adjustable PIP mechanism within the body portion and a two-way valve within the body portion that allows air to move from the expandable bag in a first direction through a first portion of the two-way valve and that directs in an opposing direction through a second portion of the two-way valve to create PEEP. The valve housing portion additionally includes a first, second, and third adjustable control devices. The first adjustable control device is mounted to the body portion and adjusts the PIP mechanism to provide one of a plurality of predetermined peak inspiratory pressures. The second adjustable control device is mounted to the body portion and adjusts a tidal volume of the expandable bag to provide a predetermined tidal volume. The third adjustable control device is mounted to the body portion and adjust the two-way valve to provide a predetermined PEEP. The first, second, and third adjustable control devices are mounted independently of one another.

In certain aspects, the valve housing portion additionally includes a filter body that is secured to the valve housing. In certain aspects the filter body includes a bio/viral filter that filters patient exhalations. In certain aspects, the filter body includes an exhalation port that is couplable to an end-tidal $CO_2$ monitor.

In certain aspects, the first adjustable control device is labeled with indicia that corresponds to established PIP standards. In certain aspects the second adjustable control device is labeled with indicia that corresponds to established standards used to determine volumes of air needed for a patient based on their length, weight, and/or age.

In certain aspects, the second adjustable control device includes two identical sets of a plurality of cogs of varying depth that provide the adjustment of the second adjustable control device. In certain aspects, the second adjustable control device includes two identical ramped surfaces of varying depth that provide the adjust of the second adjustable control device.

In certain aspects, the valve housing portion additionally includes a removable PEEP lock that is removably secured to the body portion of the valve housing portion; the PEEP lock maintains a PEEP of zero and prevents adjustment of the third adjustable control device.

In certain aspects, the valve housing portion additionally include a single control device indicator to indicate a set position of both the first adjustable control device and the second adjustable control device.

BRIEF DESCRIPTION OF THE DRAWINGS

The inventive aspects of the present disclosure can be more easily understood, and further advantages and uses thereof can be more readily apparent, when considered in view of the detailed description and the following figures in which:

FIG. 47 illustrates a bottom perspective view of a filter body coupled to the expandable bag device of FIG. 46A.

FIGS. 56A-56B illustrate a top plan view of the expandable bag device of FIG. 46A including projecting external stops in a fully compressed position and a non-fully compressed position, respectively.

FIGS. 57A-57C illustrate a lower perspective view of the expandable bag device of FIG. 46A with each side incorporating contoured edges, an upper perspective view of the expandable bag device of FIG. 46A with each side incorporating contoured edges, and an upper perspective view of the expandable bag device of FIG. 46A with each side incorporating tabs, respectively.

DETAILED DESCRIPTION

Figure 1:
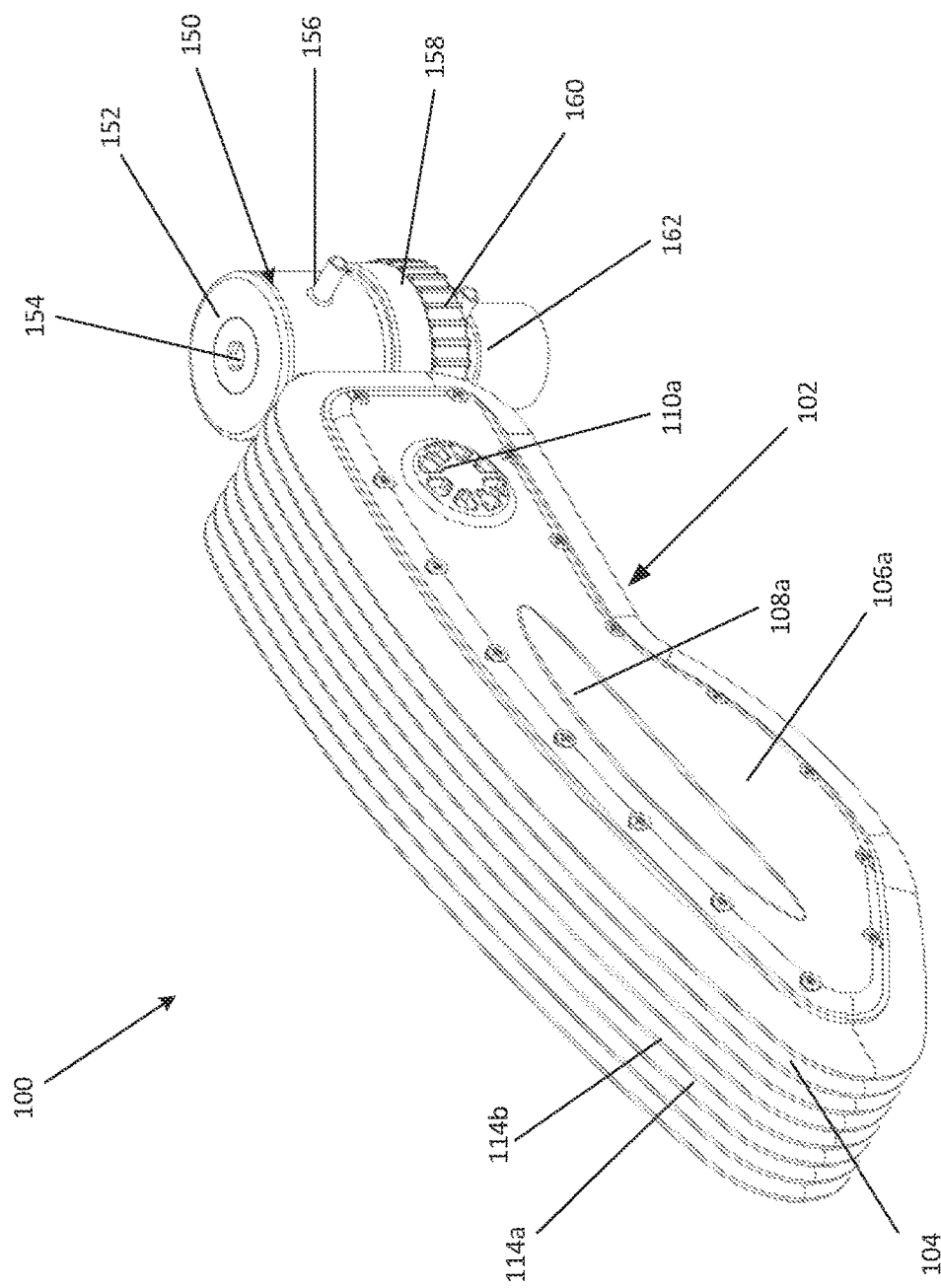
FIG. 1 illustrates an example embodiment of an expandable bag having features that are examples of inventive aspects in accordance with the present disclosure.

The figures and descriptions provided herein may have been simplified to illustrate aspects that are relevant for a clear understanding of the herein described devices, systems, and methods, while eliminating, for the purpose of clarity, other aspects that may be found in typical devices, systems, and methods. Those of ordinary skill may recognize that other elements and/or operations may be desirable and/or necessary to implement the devices, systems, and methods described herein. Because such elements and operations are well known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Generally, bag-valve-masks (BVM) are comprised of three key components: a self-inflating bag, a two-way valve, and a mask. The bag is designed to expand, fill and retain a volume of air. This volume constitutes the next "breath" that a patient is to receive. When the bag is compressed by a lifesaver's hand (herein referred to as the user), the breath is pushed through a valve and down into the mask portion of the device. The mask is kept in contact with the patient's face and directs the breath downward and into the mouth or nasal passage of the patient and into their lungs. When the bag compression is released, the bag expands and a new volume of "fresh" air is drawn into the bag while the original breath of "used" air exits the patient and is released into the ambient air via the two-way valve.

The disclosure is directed generally to a respiratory device for providing respiratory support to a patient that includes an expandable bag and a rigid valve housing portion. The expandable bag includes an air intake valve, an adjustable predetermined tidal volume and a hinge configured to maintain the expandable bag in a predetermined tidal volume in an uncompressed configuration. The rigid valve housing portion is in fluid communication with the expandable bag and includes a body portion, an adjustable peak inspiratory pressure (PIP) mechanism within the body portion, a two-way valve within the body portion that allows air to move from the expandable bag in a first direction through a first portion of the two-way valve and that directs air in an opposing direction through a second portion to create positive end-expiratory pressure (PEEP), first, second and third adjustable dials to adjust a PIP value, a tidal volume and a PEEP value, respectively, and a patient breathing interface.

FIG. 1 illustrates an example embodiment of an expandable bag device 100. The expandable bag device 100 includes an expandable bag portion 102 and connection member 150. The expandable bag device 100 may be attached to any type and size of mask or other patient breathing interface device, such as an endotracheal tube or laryngeal mask airway. The expandable bag portion 102 includes an expandable bag 104, a first side panel 106a, second side panel (not shown), a first handle portion 108a, a second handle portion (not shown), and at least one air intake valve 110.

In an example embodiment, the expandable bag 104 has an accordion-like design, comprising a plurality of folds 114a, 114b, such as a bellow, or other similar mechanism. The plurality of folds 114 allows the expandable bag 104 to expand and contract. This allows the expandable bag 104 is occupy minimal space when not in use. The expandable bag 104 can be made from a variety of materials such as flexible plastics. The expandable bag 104 includes a side panel 106 that is stiffer than the expandable bag 104 to allow a user to hold the side panel 106a to compress the expandable bag 104. The side panel 106a is made from a plastic that has a rigidity greater than the expandable bag 104. The side panel 106a also comprises a handle portion 108a. The handle portion 108a may optionally be raised or depressed from the side panel 106a to provide a surface for a user's fingers to grip and/or grab when compressing the expandable bag 104.

The rigidity of the side panel 106a allows a user to press against it in order to compress the expandable bag 104. This allows a user to compress the expandable bag portion 102 fully, as when a user compresses the side panels 106a, the side panel 106a compresses the entire length of the expandable bag 104.

The side panels 106 may also be configured to be easily held in a user's hand. In an example, the side panels 106 may each include an angled plate that makes it easier for the user to hold in one hand while inflating and deflating the bag even if the user's grip is relaxed on the expandable bag 104. Additionally or alternatively, the side panels 106 may include a grip material, such as rubber that makes it easily to hold. In yet another embodiment, the side panels 106 include a recess or legs that a user can grip with their hand. In yet another embodiment the side panels 106 could include a strap (not shown) to help the user maintain contact with the sides of the device.

The first side panel 106a and expandable bag 104 also include a first air intake valve 110a. The first air intake valve 110a extends through the first side panel 106a and into the expandable bag 104. The first air intake valve 110a provides the expandable bag 104 with ambient air intake to re-inflate the expandable bag 104. In an embodiment, each side panel 106 may comprise an air intake valve 110. In an alternative embodiment, the first side panel 106a includes the first air intake valve 110a.

The expandable bag 104 is a self-inflating bag, in which the expandable bag 104 takes on an expanded configuration without any external input from the environment. The interior of the expandable bag 104 includes a spring, which is described in more detail below.

The expandable bag portion 102 is connected to a connection member 150. The connection member 150 includes a pressure relief valve 154 located at the top 152 of the connection member 150, a dial 158, and a mask connection member 162. In an embodiment, the pressure relief valve 154 is a one-way valve that only lets air flow from inside the connection member 150 to the external environment.

The dial 158 controls the positive end expiratory pressure (PEEP) valve, which is the controlled resistance of the exhaled airflow. The dial 158 controls the location of side panels of an internal valve, such as a barrel valve (shown in FIGS. 13-17). When the dial 158 is turned up, the side panels move closer together, so it is harder for the patient to exhale against. The dial 158 can have different values such as from 0 to 20 mmHg. Alternatively, a push button (shown in FIG. 20) may be used to control PEEP.

The connection member 150 also includes two optional external pressure gauge connection members 156, 160. The optional external pressure gauge connection members 156, 160 can be used to indicate the internal pressure levels of different components of the expandable bag device 100. The external pressure gauge connection member 156, 160 can be used to measure the pressure of a patient's lungs upon inspiration (PIP—peak inspiratory pressure). The external pressure gauge connection member 156, 160 can be used to measure the pressure of the patient's lungs during exhalation (PEEP). In other embodiments, these two valves are not present, or are capable of being closed.

The connection member 150 is made from a stiff material that allows a user to hold the expandable bag device 100 in one hand. A user is able to compress the expandable bag portion 102 with one hand, while maintaining a seal of a mask on a patient's face with the same hand. The stiffness of the connection member 150 allows for single-handed use of the expandable bag device 100.

Figure 2:
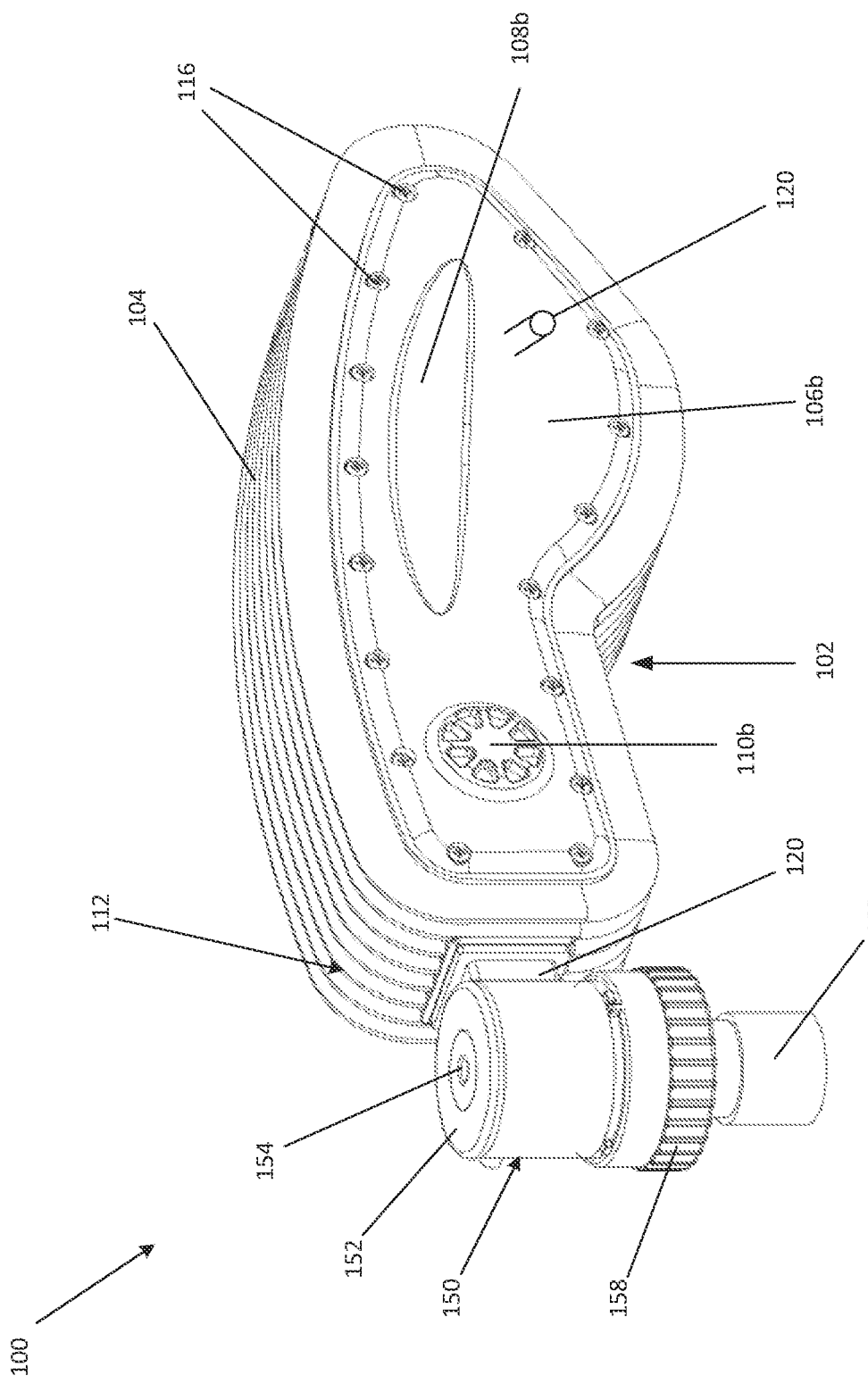
FIG. 2 illustrates a perspective view of the back side of the expandable bag of FIG. 1.

FIG. 2 illustrates a rear view of the expandable bag device 100. As shown, the expandable bag portion 102 includes a second side panel 106b having a second handle portion 108b, and a second air intake valve 110b. The second side panel 106b having a second handle portion 108b and the second air intake valve 110b are the same as the first side panel 106a, the first handle portion 108a, and the first air intake valve 110a shown in FIG. 1, and the descriptions of which are omitted for the sake of brevity. The first side panel 106a and the second side panel 106b sandwich the expandable bag 104.

A plurality of attachment points 116 are located along each side panel 106 to attach each side panel 106 to the expandable bag 104. Various types of attachment mechanisms may be used to attach each side panel 106 to the expandable bag 104, such as adhesives or mechanical connections.

Still referring to FIG. 2, the expandable bag 104 is attached to the connection member 150 via the bag connection member 120. The connection member 150 may be fixedly connected to the expandable bag portion 102, or alternatively, may be removable. In a removable embodiment, an attachment mechanism may be selected from a snap fit, friction fit, or other similar mechanism.

In an example embodiment, the connection member 150 includes an "over-breathing" valve (not shown). As shown in more detail at FIG. 17, the over-breathing valve allows a patient to breathe on their own, even without the expandable bag 104 providing the air. For example, if a patient has a mask on, and the patient can or begins to breathe on their own, the over-breathing valve allows the patient to breathe.

The expandable bag device 100 is shaped such that it takes up minimal space during storage. When the expandable bag device 100 is not being used, a mask (not shown) is detachable from the mask connection member 162, and can be stored next to the expandable bag portion 102. In order to take up minimal space, the expandable bag portion 102 has a shape that allows the mask portion to abut against it, such as having the expandable bag portion 102 having a rounded concave shape. Still further, the expandable bag device 100 is designed so the expandable bag portion 102 is compressible and does not hold any air when not in use.

The expandable bag device 100 is configured to be used by a user to provide respiratory support to a patient. In use, the expandable bag device 100 is connected to a mask (not shown) at the mask connection member 162, which provides air to a patient in need. The expandable bag device 100 is biasable at the articulation point 112, by a user. The articulation point 112 maintains the expandable bag 104 in an open or expanded configuration (shown in more detail below at FIGS. 11-12). When a user compresses the side panels 106a, 106b, the expandable bag 104 compresses, which forces air through the bag connection member 120 (discussed in more detail below), through the connection member 150 and into a mask (not shown). Alternatively, the connection member 150 may be connected to a different patient breathing interface, such as an endotracheal tube, an end-tidal $CO_2$ connector, or a laryngeal mask airway.

In an embodiment, the articulation point 112 is a spring located within the expandable bag 104. The articulation point 112 may be made from a material such as metal, fiberglass, carbon fiber, plastic, or any other structural material that will bias the expandable bag 104 in an inflated or expanded configuration. The articulation point 112 has a strength great enough to keep the bag open when not subject to external forces, but weak enough that a user can squeeze the side panels 106, which bias the articulation point 112 with one hand. Still further, the articulation point 112 is designed with a material that does not allow the expandable bag 104 to open too quickly. For example, the articulation point 112 comprises a hinge that is configured to inflate the expandable bag 104 in 5-6 seconds; however, other time periods may be utilized.

The expandable bag device 100 is configured such that when a user compresses the side panels 106a, 106b, the entire expandable bag 104 is compressed. This allows the expandable bag 104 to have a size that is the volume of air needed, without having to be oversized. This also allows the expandable bag 104 to be as compact as possible.

When a user desires to provide subsequent "breaths," the user relaxes the compression on the side panels 106a, 106b of the expandable bag 104, which allows the expandable bag 104 to expand into the expanded configuration. The air intake valves 110 allows air to move from an external environment to the inside of the expandable bag 104.

In another embodiment, the expandable bag portion 102 further comprises an oxygen port 121 which can be connected to a source of oxygen (not shown). In use, an oxygen port 121 can instill a predetermined volume of pure oxygen in the expandable bag portion 102. When the expandable bag portion 102 is expanded, it can pull in ambient air from the periphery to blend with the oxygen from an oxygen source which is coupled to the expandable bag portion 102 by the oxygen port 121.

The oxygen port 121 may further include an indicator (not shown) that indicates to the user that oxygen is flowing into the expandable bag 104. An example indicator may be a flap, a spinner, or a valve that moves due to the flow of oxygen, and the user is able to see the movement of the indicator. In such an example, the indicator may be translucent and the indicator may be colored. In another example, the indicator may have a noise-making device that whistles when oxygen is flowing through the indicator into the expandable bag 104.

Figure 3:
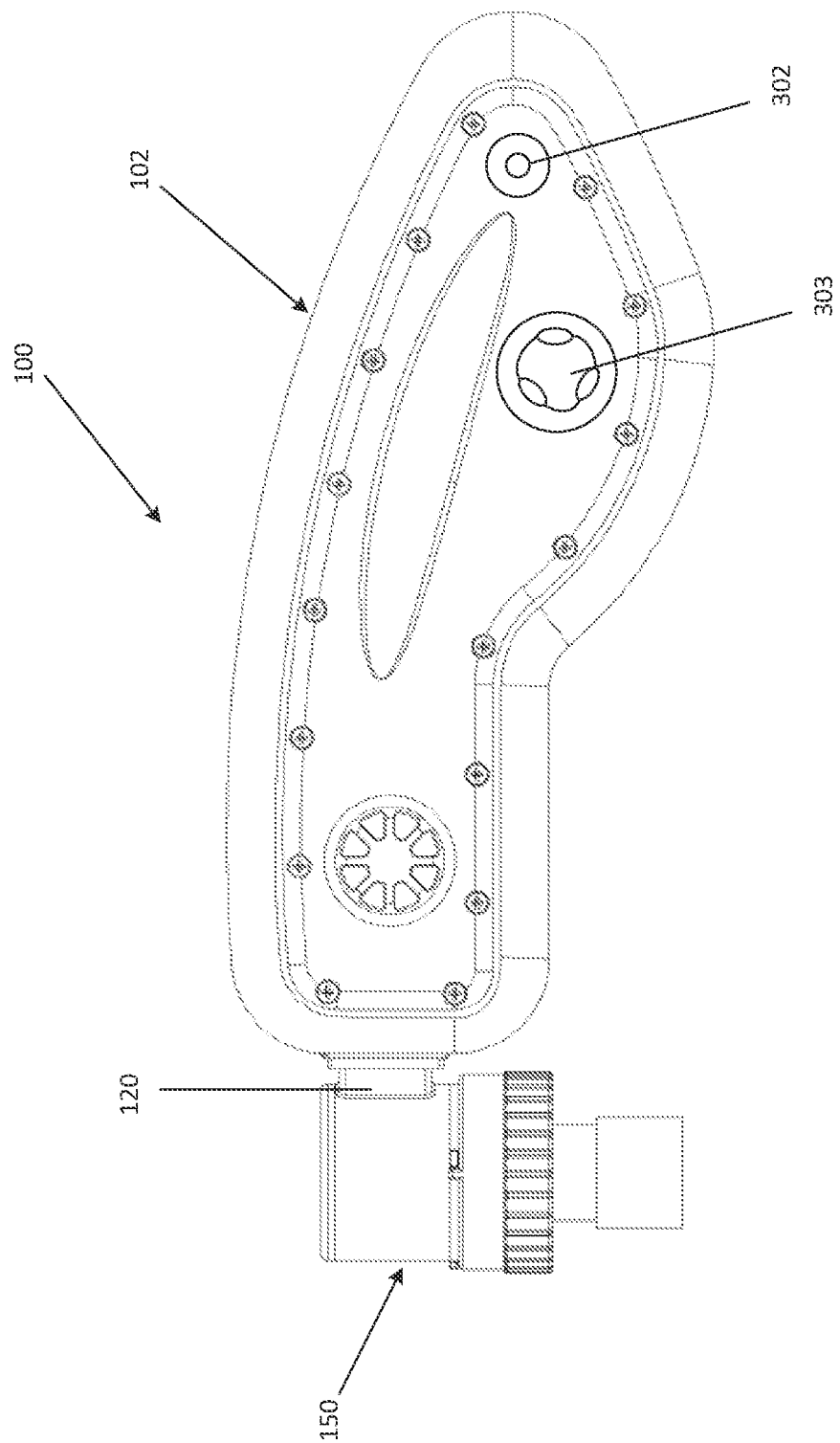
FIG. 3 illustrates a first side view of the expandable bag.

FIG. 3 illustrates a side view of the expandable bag device 100. The bag connection member 120 connects the expandable bag portion 102 to the connection member 150. The bag connection member 120 includes a lumen, and may or may not include a valve. In an embodiment comprising a valve, the valve is a one-way valve that only allows air to move from the expandable bag portion 102 to the connection member 150.

In an example embodiment, the expandable bag portion 102 also includes a buckle 302. The buckle 302 allows a strap (not shown) to be connected to a first side panel 106a and a second side panel 106b. The length of the strap can determine how much the expandable bag 104 can expand. For example, a strap with a first length connected to each of the buckles 302 restricts the expandable bag 104 from opening more than a first predetermined fill volume. A strap with a second length can restrict the expandable bag 104 from opening more than a second predetermined fill volume. This allows the expandable bag device 100 to be used on patients with different sizes of lungs. For example, a short strap may be required for a neonatal patient and a long strap for a pediatric patient. No strap may be required for an adult patient.

In an alternative embodiment, a single strap may include multiple buckles at predetermined lengths, so a single strap may be used for different predetermined fill volumes. The strap can include indicia that indicates which buckle is to be used with each type of patient.

The straps (not shown) may include indicia on each that conveys pertinent information for the resuscitation of each patient size. For example, the shorter strap for older pediatric patients might remind a user to give 15 compressions for 2 rescue breaths when cardiopulmonary resuscitation is given by the user.

In yet another embodiment, a dial or push button mechanism 303 may be used to control the tidal volume. The push button mechanism 303 controls how large the expandable bag portion 102 is able to expand. For example, the push button mechanism 303 may include three different predetermined volumes, such as a tidal volume for a neonatal patient, a second tidal volume for a pediatric patient, and a third tidal volume for an adult patient. This allows the expandable bag device 100 to be used on patients with different sizes of lungs.

Figure 4:
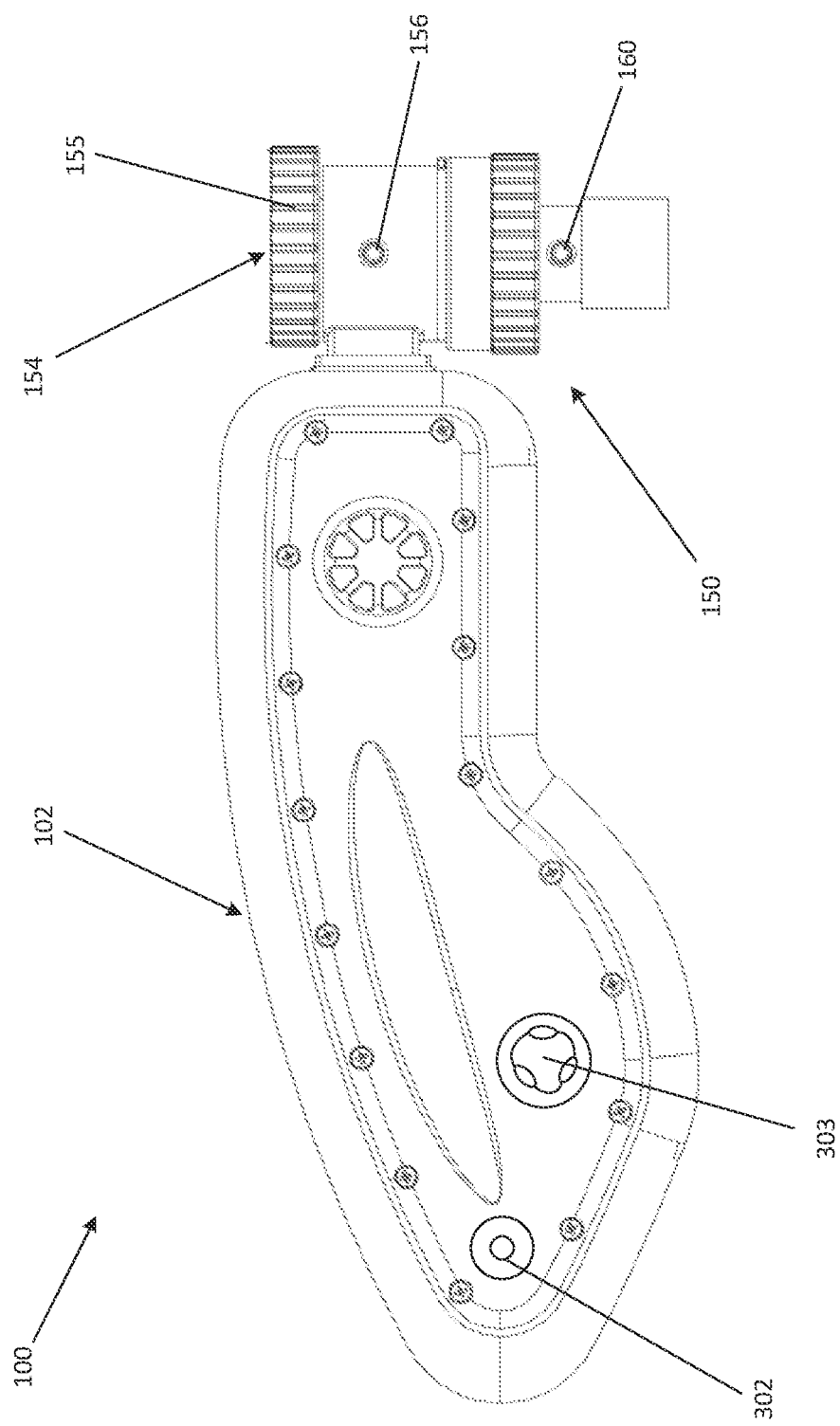
FIG. 4 illustrates a second side view of the expandable bag.

FIG. 4 illustrates an opposing side view of the expandable bag device 100. In an example embodiment, the connection member 150 includes a first external pressure gauge connection member 156 and a second external pressure gauge connection member 160. As described above, these external pressure gauge connection members 156, 160 allow a user to attach a pressure gauge to determine the pressure provided or received at each of the external pressure gauge connection members 156, 160. The opposing side also includes a buckle 302, the details of which are omitted for brevity.

In an embodiment, the pressure relief valve 154 includes a dial 155 that allows the pressure at which the pressure relief valve 154 vents air to be adjustable. In an embodiment, the pressure relief valve 154 is configured to vent air at a pressure of 40 cm water. In another embodiment, the pressure at which the pressure relief valve 154 vents air is adjustable. An adjustable pressure relief valve 154 may be controllable the dial 155 or other similar mechanism.

Figure 5:
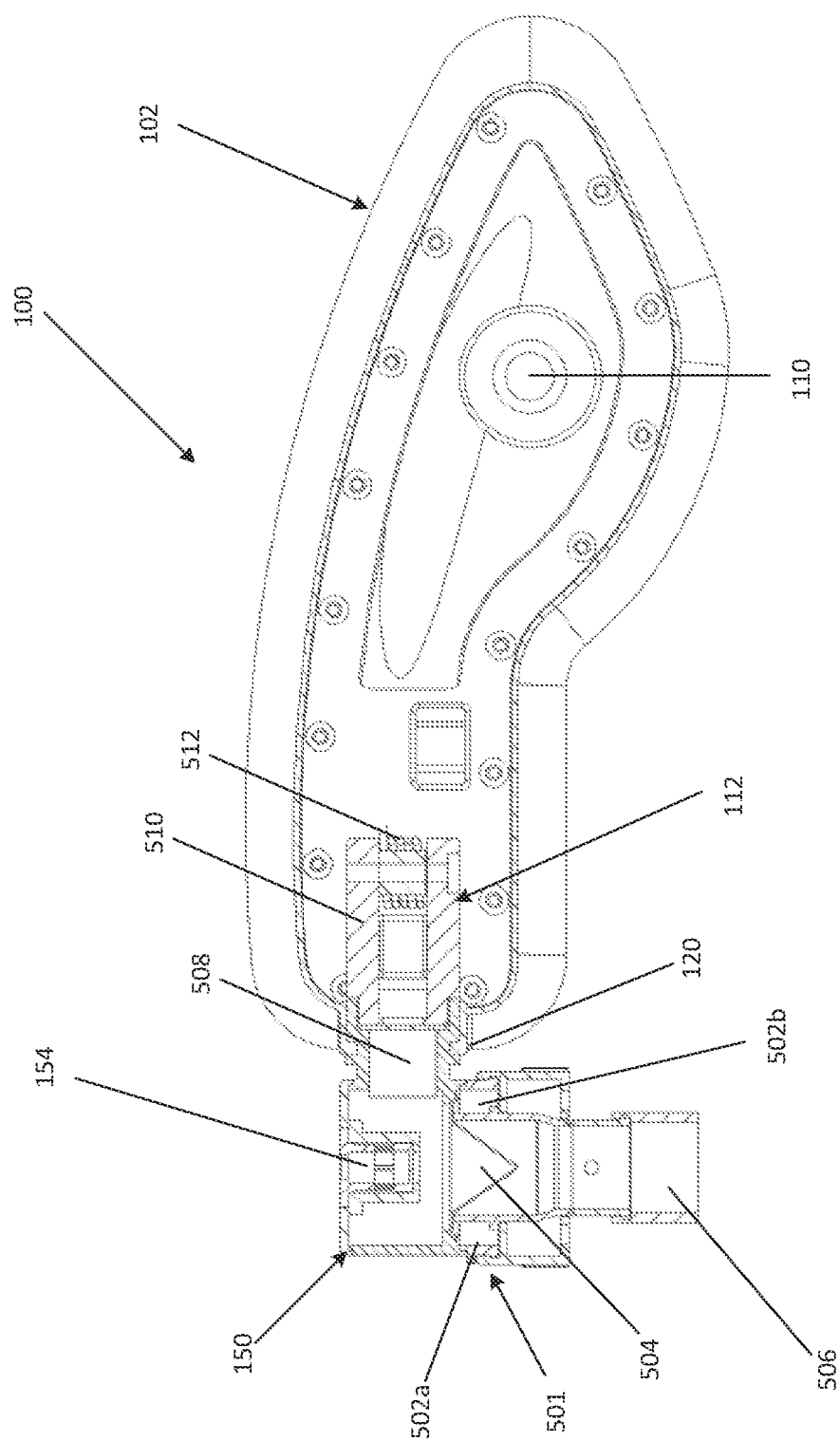
FIG. 5 illustrates a vertical cross-sectional view of the expandable bag of FIG. 1.

FIG. 5 illustrates a vertical cross-sectional view of the expandable bag device 100. The connection member 150 includes the pressure relief valve 154 located at the top of the connection member 150, a PEEP valve 501, and a two-way valve a located above a mask connection lumen 506. The two-way valve 504 may be a duckbilled valve.

The pressure relief valve 154 may be a ball-and-spring valve that relieves excess pressure. Alternatively, the pressure relief valve 154 may be a pop-off valve, a stiffened duck-billed or other type of valve. The pressure relief valve 154 is a one-way valve, so air only moves from the inside of the connection member 150 to the external environment.

The PEEP valve 501 may be comprises of two separate valves, each located lateral to the two-way valve 504. In an example embodiment, the PEEP valve 501 includes two barrel valves 502. For example, a first side of the barrel valve 502a is located on a first side of the two-way valve 504 and a second side of the barrel valve 502b is located on a second side of the two-way valve 504. This is shown in more detail at FIGS. 13-16. As described above, the PEEP valve 501 is controlled by the dial 158.

The two-way valve 504 allows air to move from the connection member 150 through the mask connection lumen 506 into a mask (not shown) for a patient to breathe. This is shown in more detail at FIGS. 13-16.

In an alternative embodiment, the PEEP valve 501 may be a different type of valve, such as a torsion valve or a compression valve. Other types of valves include duckbill, diaphragm, spool, butterfly, needle, ball, gate, poppet, plug, and flapper.

The expandable bag device 100 is biasable at the articulation point 112. The expandable bag portion 102 includes a biasing member 512 connected to front side and back side of the expandable bag 104 at connection point 510. The biasing member 512 may be a spring, or other type of member that allows the bag to articulate at the articulation point 112. The biasing member 512 has a strength such that it does not cause the expandable bag 104 to open too quickly when in use. Other types of biasing members include but are not limited to torsion, compression, extension, bow, leaf, conical, flat, and disk/cup members.

Also shown is the air intake valve 110 of the expandable bag 104. The air intake valve 110 allows air from the external environment to fill the expandable bag 104. The air intake valve 110 may further include an indicator (not shown) that indicates to the user that the expandable bag 104 is inflating and when the expandable bag 104 has completed inflating. An example indicator may have a noise-making device that whistles when the expandable bag 104 is inflating and stops making noise when the expandable bag 104 is full. For example, the indicator may be made from a flexible material, such as a thin plastic or thin rubber.

Figure 6:
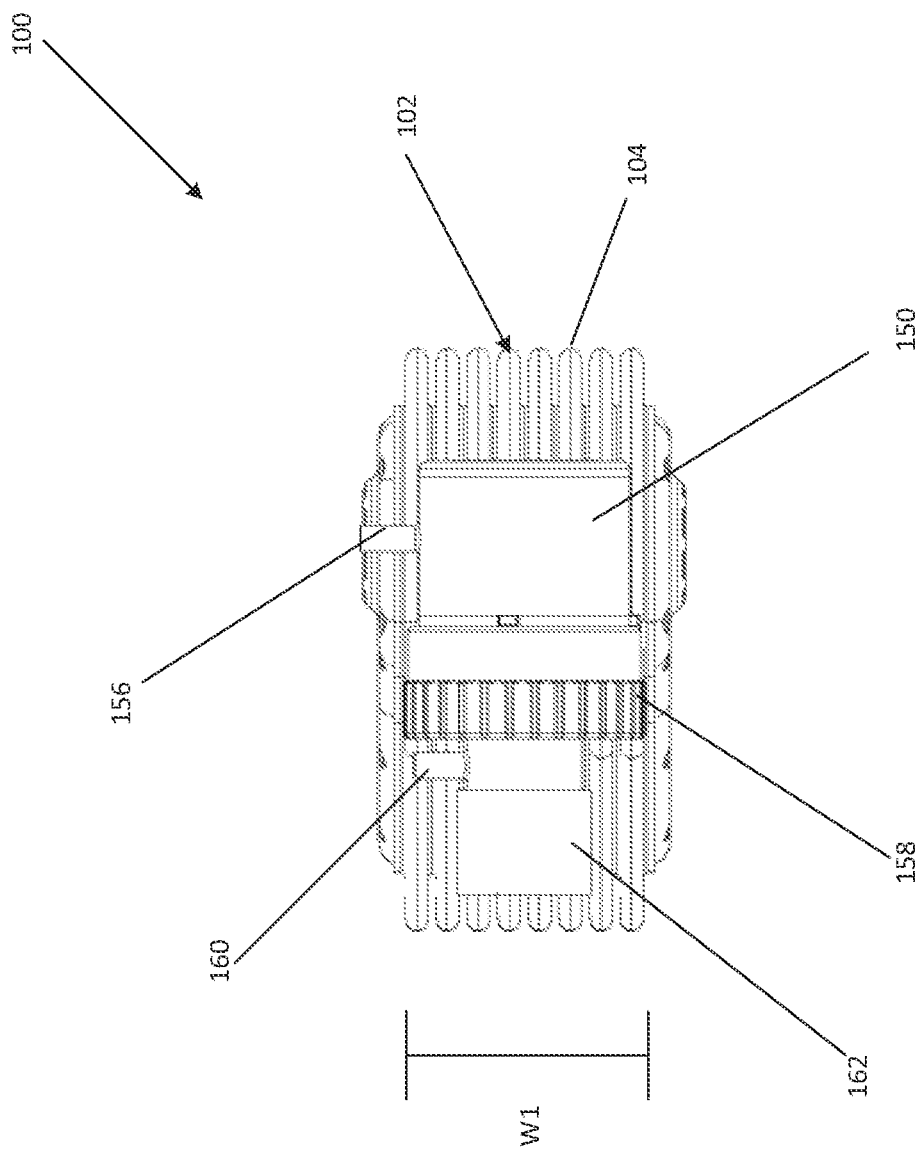
FIG. 6 illustrates a third side view of the expandable bag.

FIG. 6 illustrates a view of the connection member 150 with the expandable bag portion 102 located behind it. As shown, the expandable bag 104 of the expandable bag portion 102 is compressed. In a compressed configuration, the expandable bag 104 has a width of a first end that is the same as a width of an opposing end. For example, the width $w_1$ of the expandable bag portion 102 may be from about 2 cm to about 15 cm.

Figure 7:
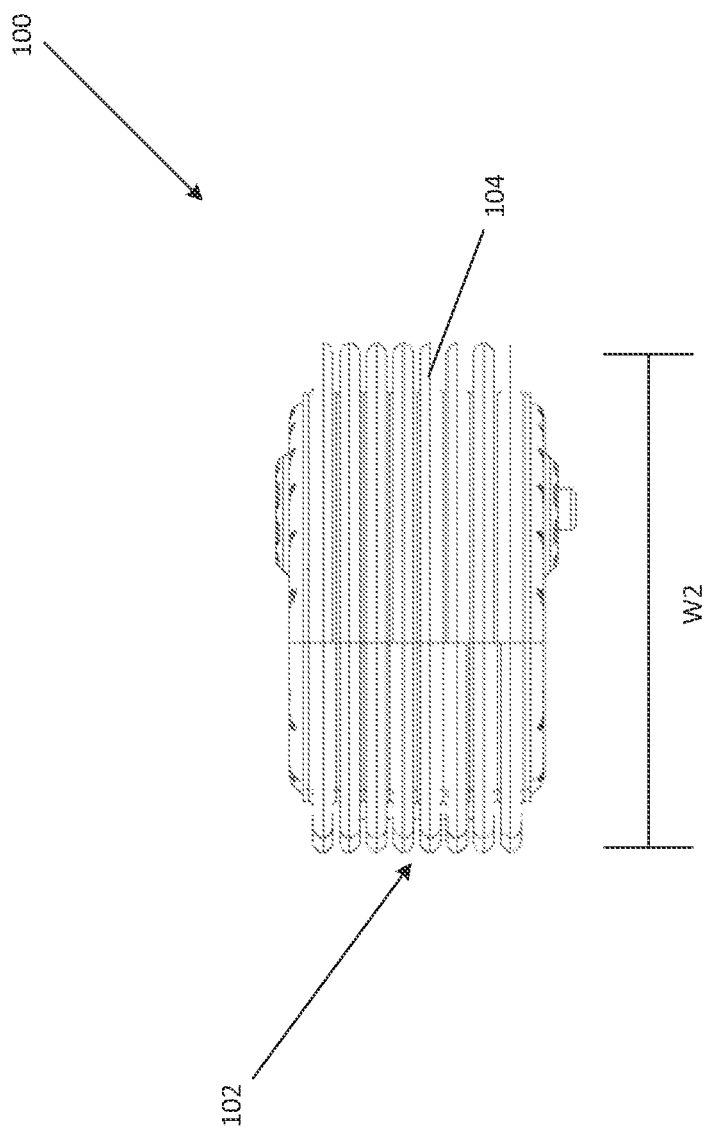
FIG. 7 illustrates a fourth side view of the expandable bag.

FIG. 7 illustrates another view of the expandable bag portion 102 in a compressed configuration. In an embodiment, a second width $w_2$ of the expandable bag portion 102 may be from about 4 cm to about 30 cm.

Figure 8:
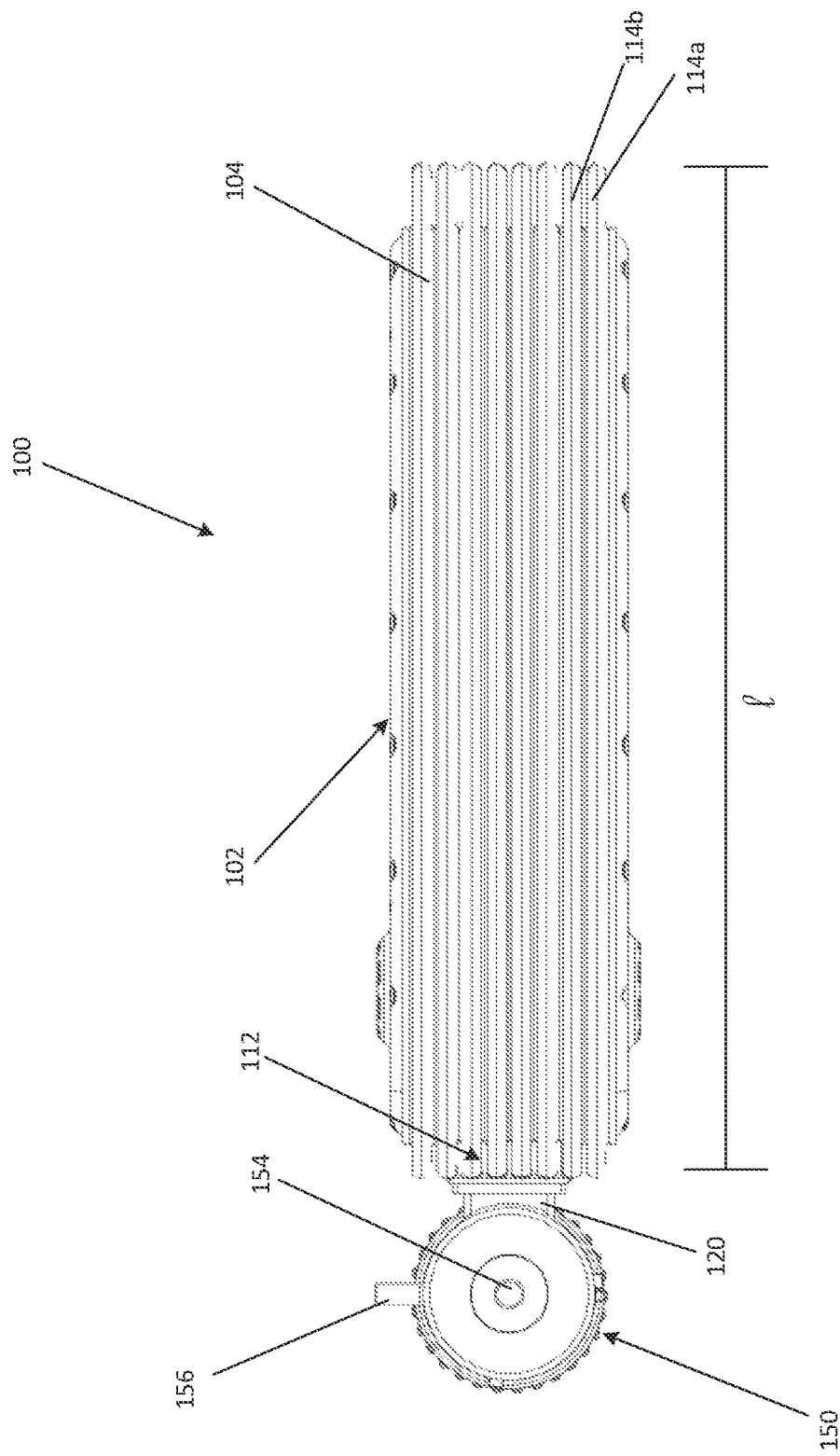
FIG. 8 illustrates a top view of the expandable bag.

FIG. 8 illustrates a top view of the expandable bag device 100. The expandable bag 104 has an accordion-type shape including a plurality of folds 114a, 114b. The plurality of folds 114 enables the expandable bag 104 to expand to a maximum capacity. A maximum capacity may be one fluid liter. In alternative embodiments, the maximum capacity may be more, such as 1.5 fluid leaders, or less, such as 0.5 fluid leaders. The length l of the expandable bag portion 102 may be from about 5 cm to about 50 cm.

The expandable bag 104 includes the articulation point 112 at an end connected to the connection member 150. The opposing end of the expandable bag 104 expands when articulation point 112 is in a biased configuration.

The top portion of the connection member 150 comprises the pressure relief valve 154. As discussed above, the pressure relief valve 154 allows air to flow from the connection member 150 to the external environment in the event that excessive pressures are applied to a patient's lungs.

Figure 9:
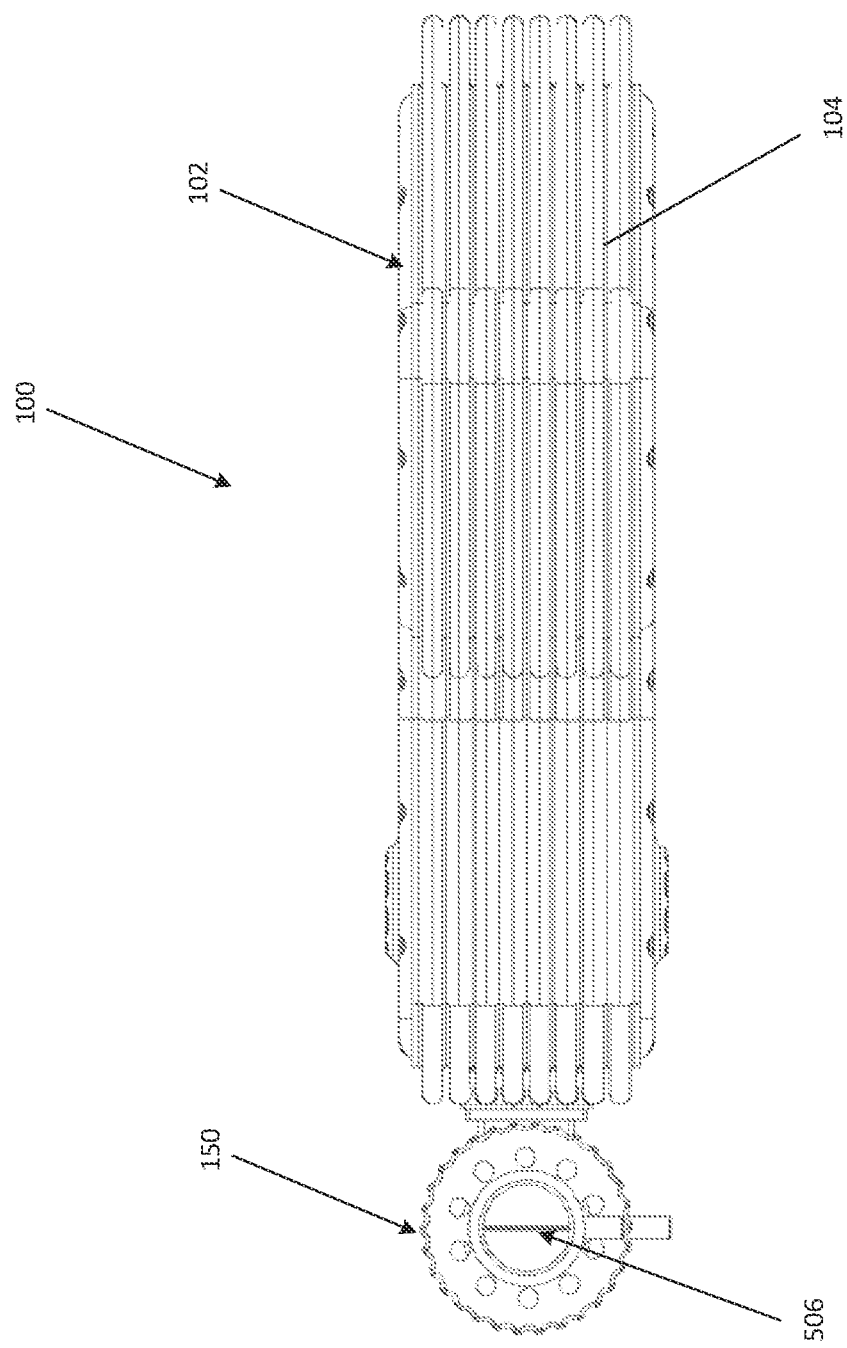
FIG. 9 illustrates a bottom view of the expandable bag.

FIG. 9 illustrates a bottom view of the expandable bag device 100. The connection member 150 includes the mask connection lumen 506, which allows the connection member 150 to connect to a mask or other patient breathing interface unit (not shown).

Figure 10:
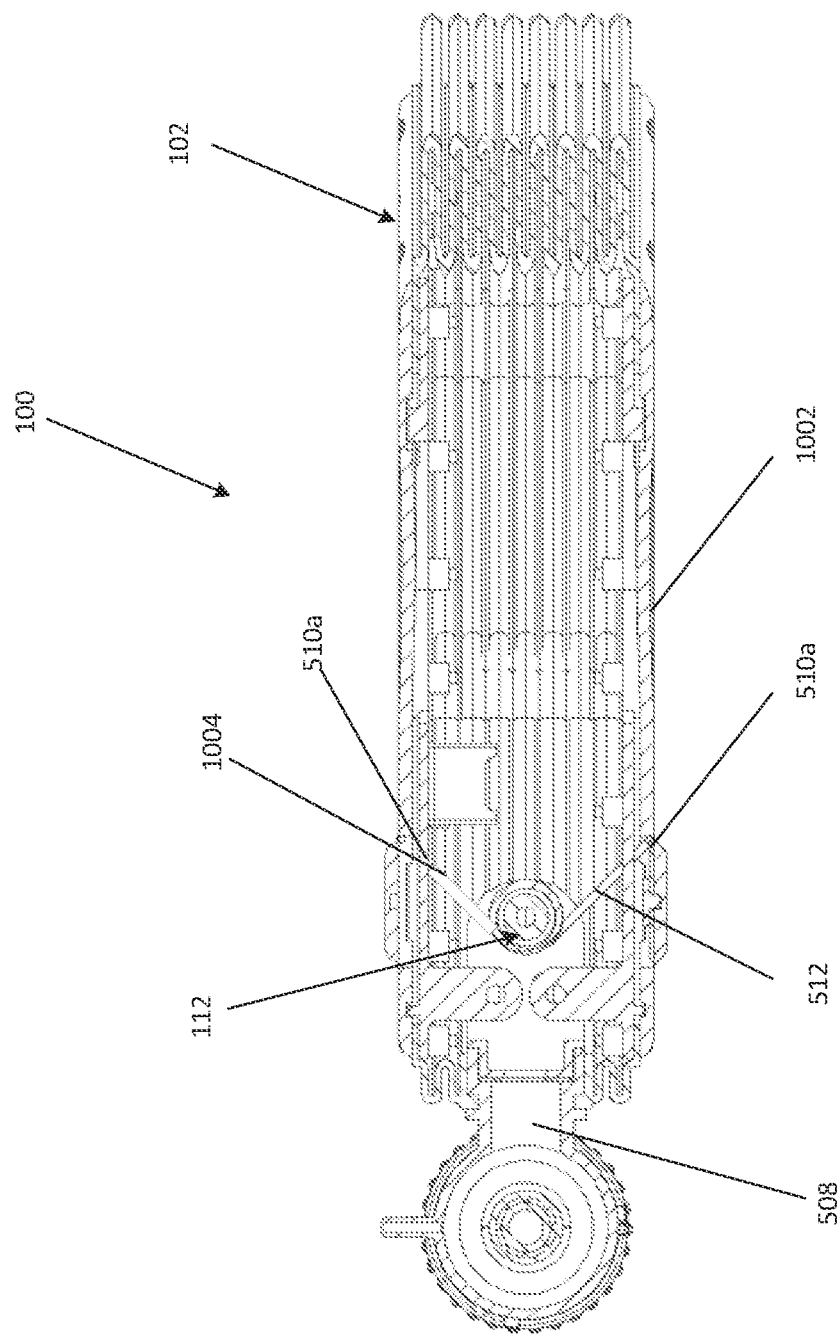
FIG. 10 illustrates a horizontal cross-sectional view of the expandable bag.

FIG. 10 illustrates a horizontal cross-sectional view of the expandable bag device 100. Articulation point 112 is located at a first end of the expandable bag portion 102. The articulation point 112 is configured to maintain an open expanded configuration, until at which time pressure is applied externally to the expandable bag portion 102 to collapse the expandable bag 104 by a user. The biasing member 512 is connected to front side 1002 and back side 1004 of the expandable bag 104 at connection point 510a, 510b. The biasing member 512 may be a spring, or other type of member that allows the bag to articulate at the articulation point 112. Other types of biasing members include but are not limited to torsion, compression, extension, bow, leaf, conical, flat, and disk/cup members.

Figure 11:
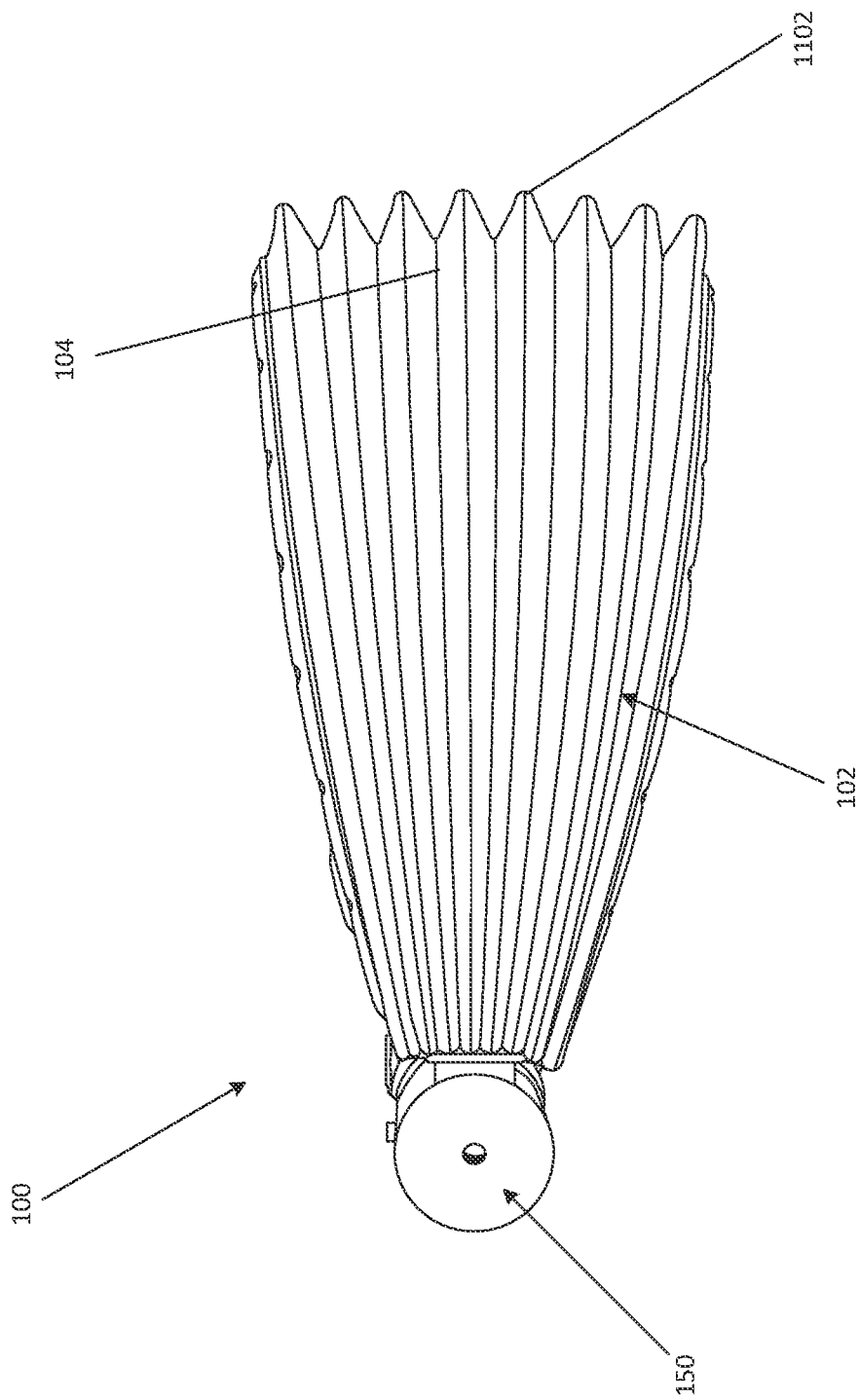
FIG. 11 illustrates a top view of the expandable bag in an expanded configuration.

FIG. 11 illustrates a top view of the expandable bag device 100 in an expanded configuration. As shown, the expandable bag portion 102 has a generally triangular-shape when in an expanded configuration. The bag could assume other shapes such as spherical, ovoid, square, rectangular, or other polygonal shape. The end 1102 of the expandable bag portion 102 opposite the connection member 150 is expanded, allowing the expandable bag 104 to fill with air. The biasing member (not shown) opens the expandable bag to a predetermined fluid volume.

Figure 12:
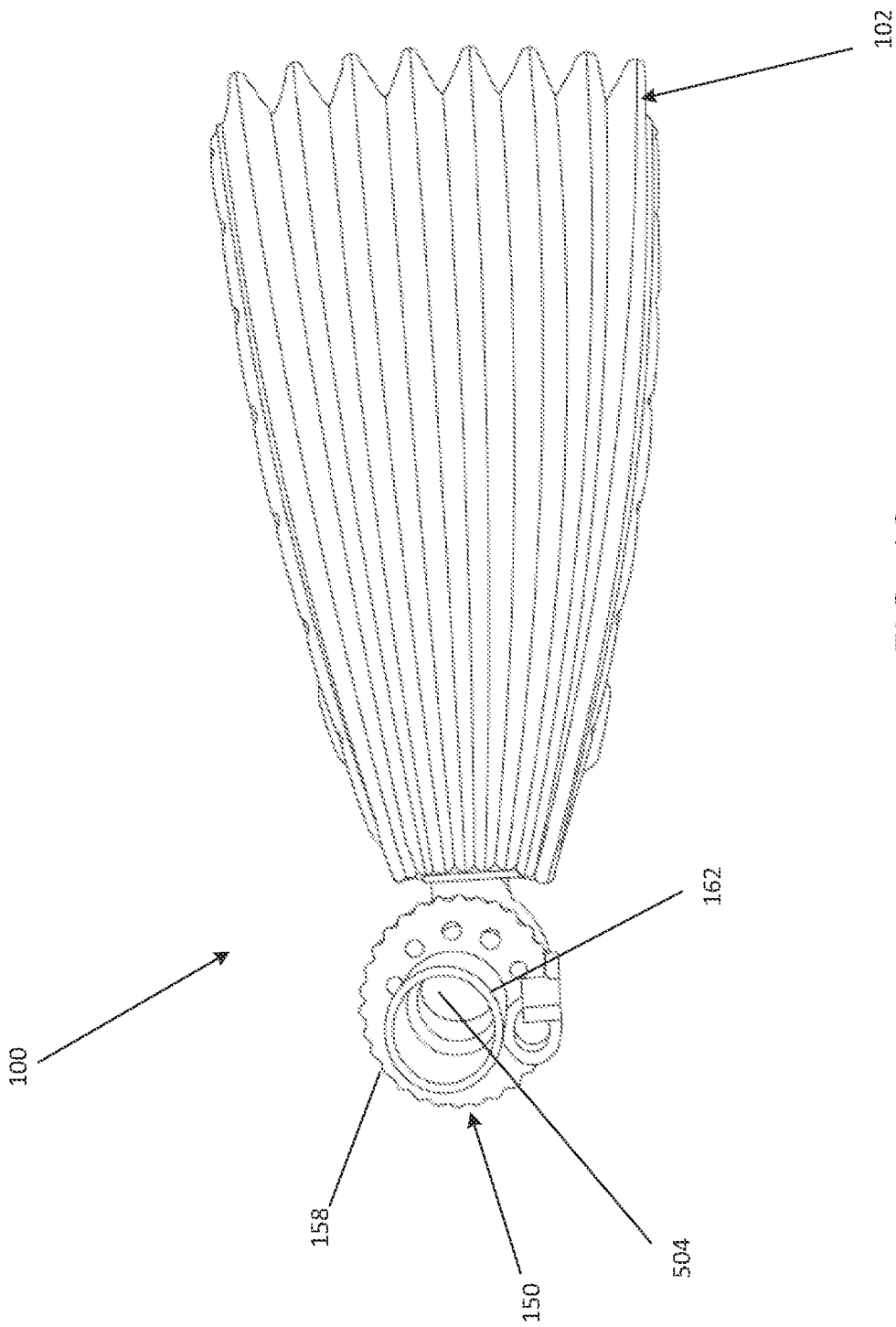
FIG. 12 illustrates a bottom view of the expandable bag in an expanded configuration.

FIG. 12 illustrates the expandable bag device 100 from a bottom viewpoint, in an expanded configuration. The connection member 150 includes a mask connection member 162 and the two-way valve 504 located within the mask connection lumen 506.

Figure 13:
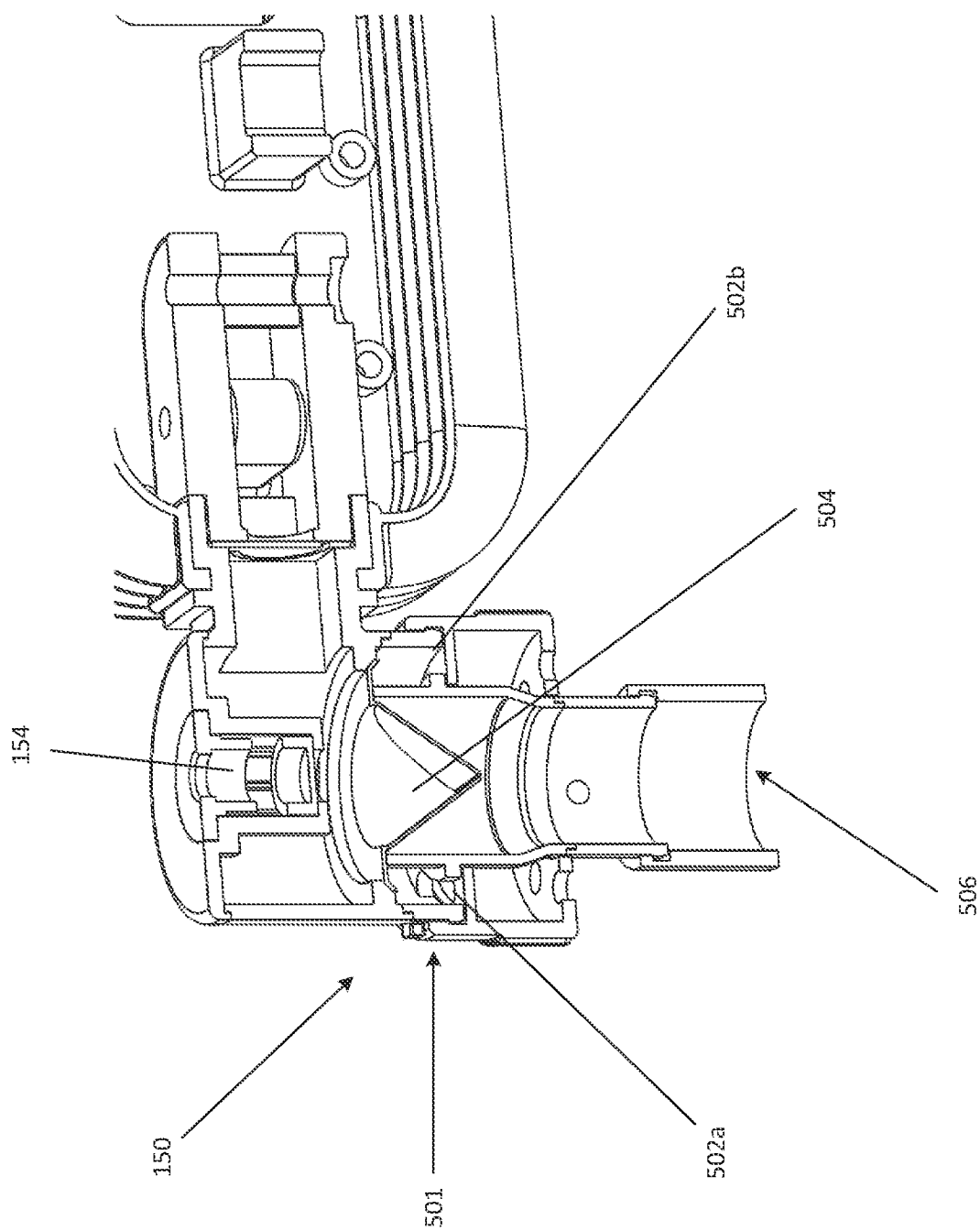
FIG. 13 illustrates a cross-sectional view of the two-way valve portion.

FIGS. 13-16 illustrate a cross-sectional view of the connection member 150. In particular, FIG. 13 shows the connection member 150 that includes the two-way valve 504 located centrally in the mask connection lumen 506. The two-way valve 504 includes two flaps that meet each other in a center of the mask connection lumen 506. The connection member 150 also includes the PEEP valve 501, which includes at least one barrel valve 502 located laterally to the two-way valve 504. For example, a first barrel valve 502a is located on a first side of the two-way valve 504, and a second barrel valve 502b is located on an opposing side of the duckbilled valve.

The PEEP valve 501 is controlled by a dial (not shown) and can be adjusted to a predetermined expiratory pressure amount. The PEEP valve 501 maintains the predetermined pressure in the lungs of the patient. The two-way valve 504 allow air from the expandable bag 104 to be provided to the patient and forces exhaled air to be expelled through the PEEP valve 501.

Figure 14:
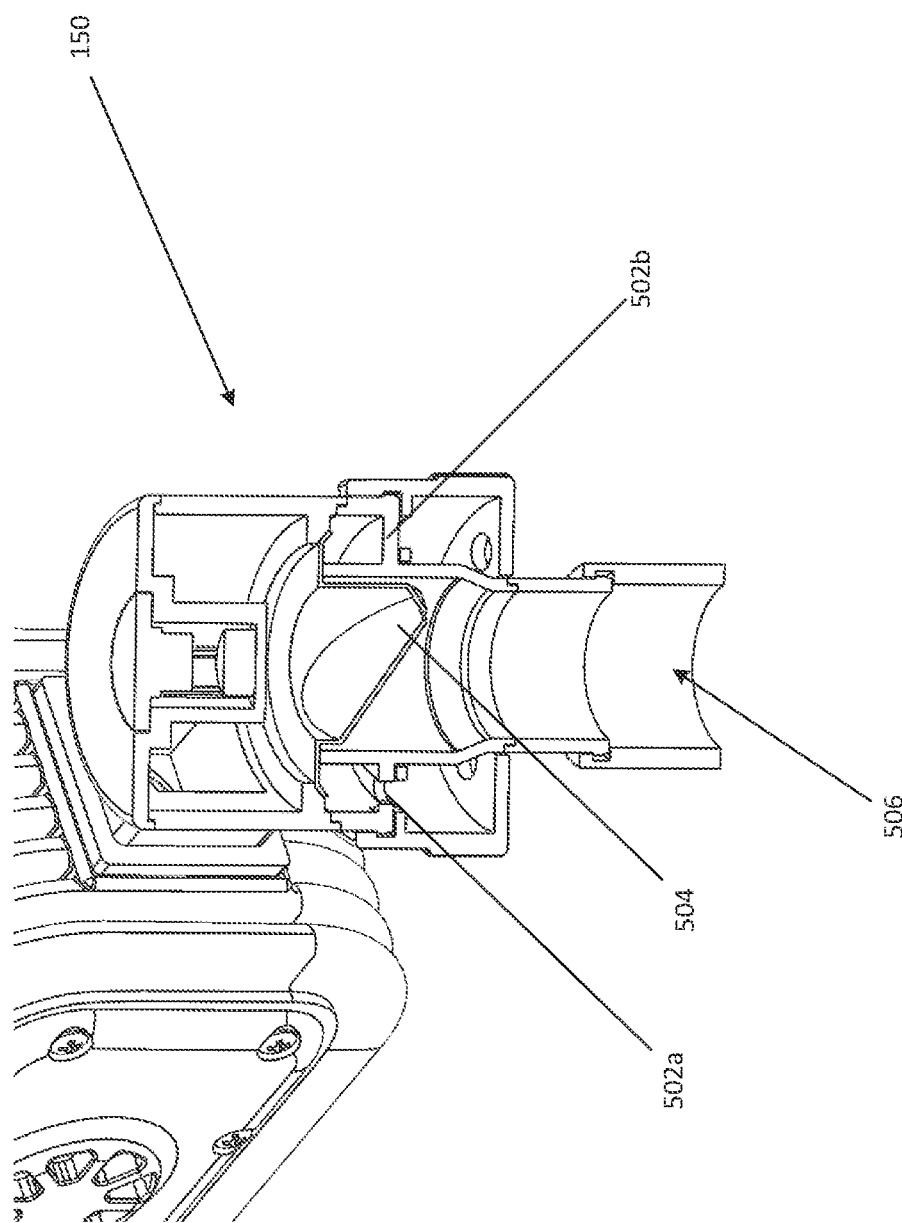
FIG. 14 illustrates a cross-sectional view of another embodiment of the two-way valve portion.

FIG. 14 illustrates an alternative embodiment of a two-way valve 504. For example the duckbilled valve includes only a single flap, where the single flap meets a side edge of the valve.

Figure 15:
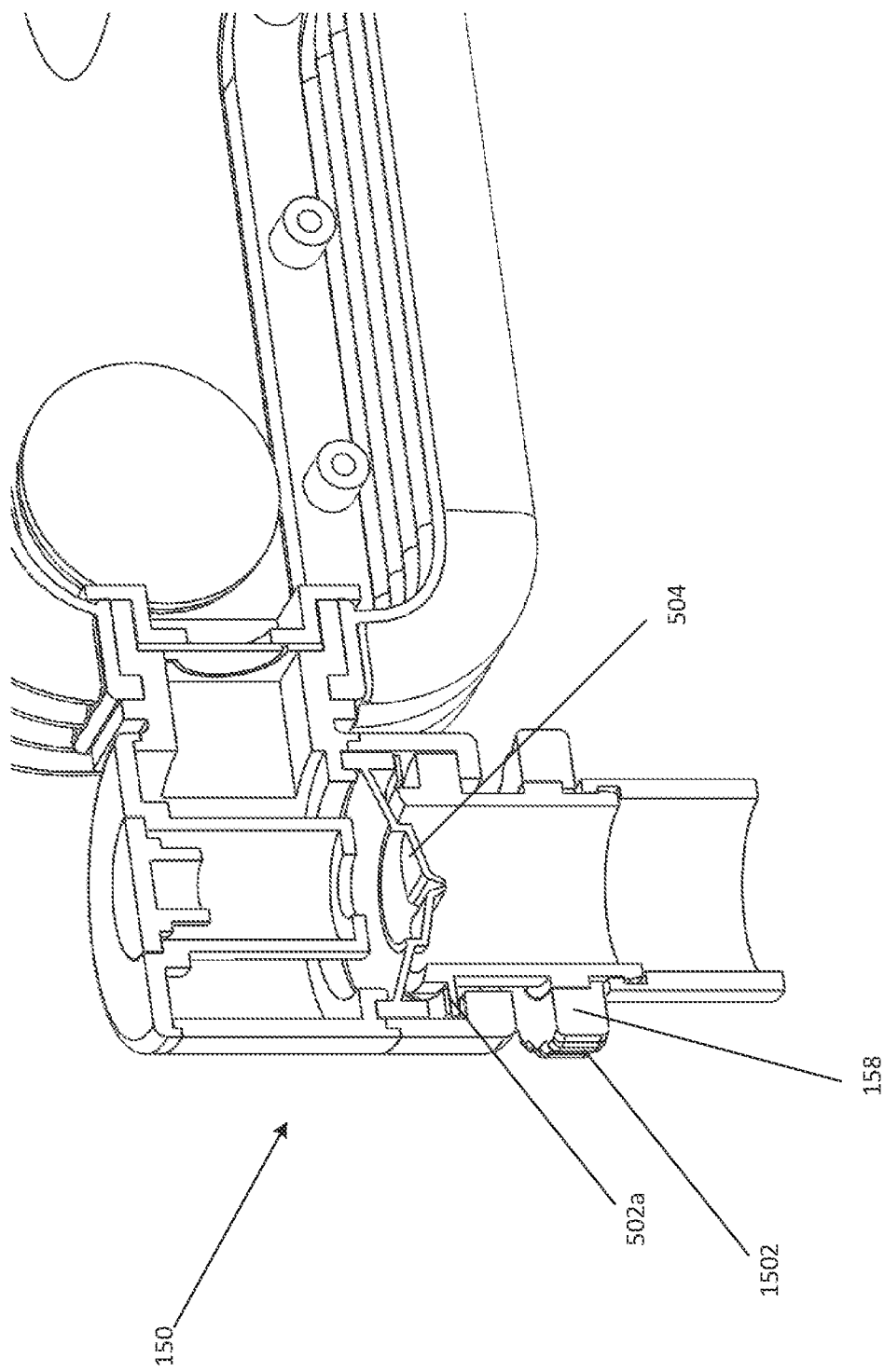
FIG. 15 illustrates a cross-sectional view of another embodiment of the two-way valve portion.
Figure 16:
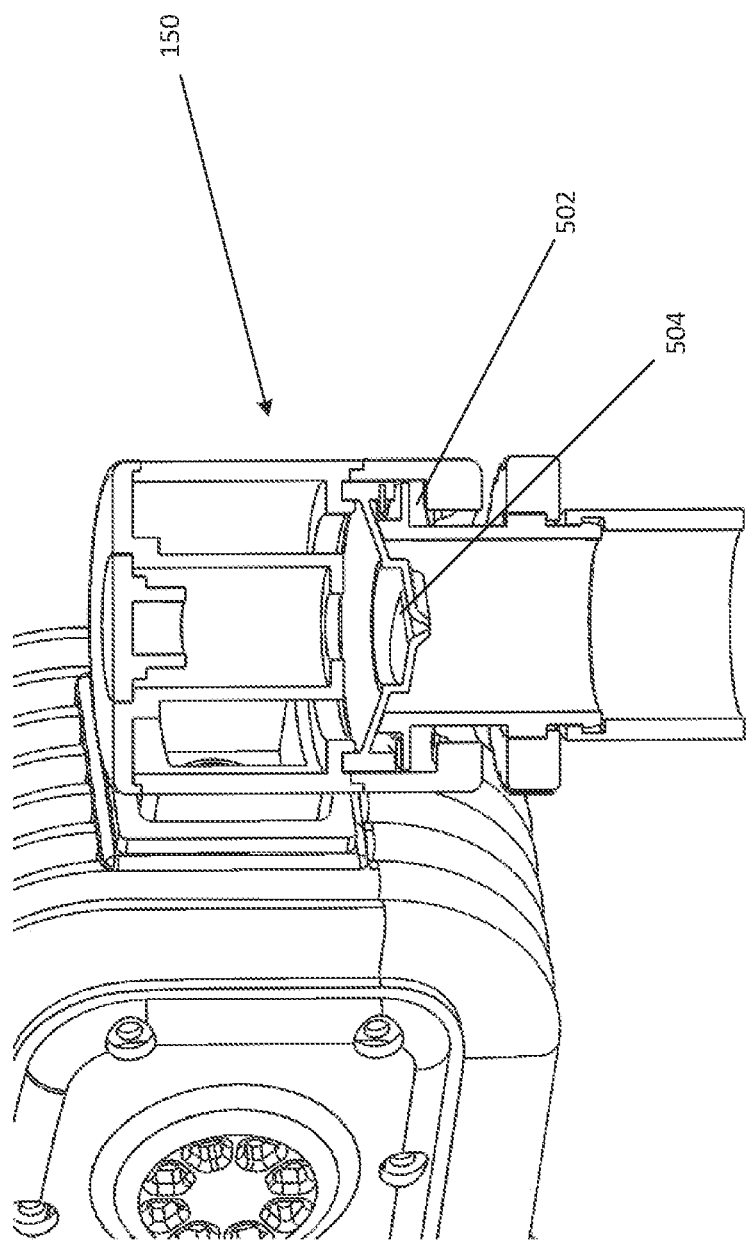
FIG. 16 illustrates a cross-sectional view of another embodiment of the two-way valve portion.

FIGS. 15-16 also illustrate an alternative embodiment of a two-way valve 504 and a groove mechanism 1502 of a dial 158. The two-way valve 504 includes two flaps that meet in a middle portion, wherein the flaps have a small articulation before joining together.

Figure 17:
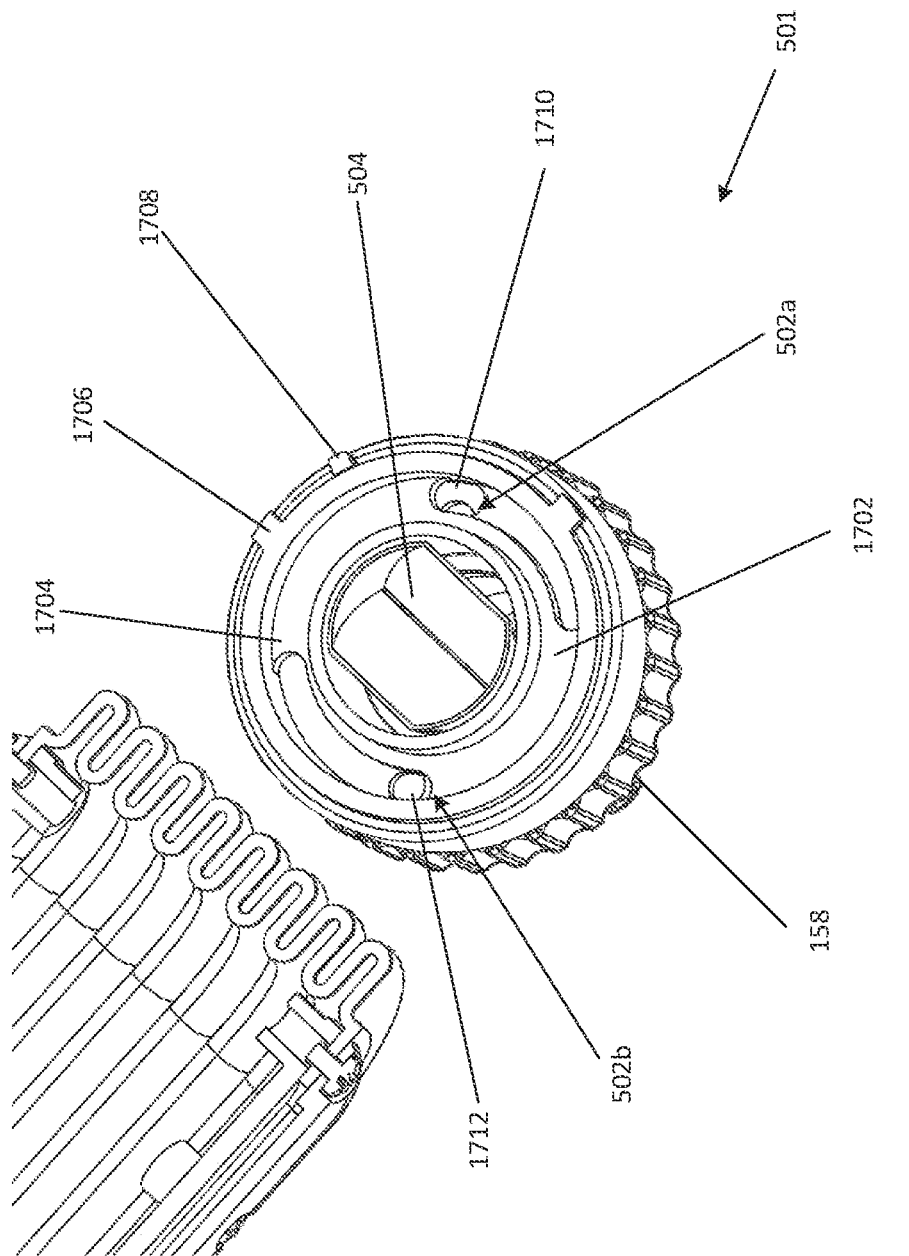
FIG. 17 illustrates a top cross-section view of the barrel-valve embodiment of the integrated PEEP valve.

FIG. 17 illustrates a top down cutaway view of the two-way valve 504 and the barrel valves 502a, 502b. The dial 158 controls the size of the barrel valves 502a, 502b. A user can rotate the dial 158 in a first direction to increase the size of the barrel valves 502, and can rotate the dial 158 in an opposing direction to decrease the size of the barrel valves 502.

The dial 158 is used to adjust the relative positions of cutouts 1702, 1704. When the dial 158 is turned fully in one direction, for example when fully turned clockwise, the cutouts 1702, 1704 do not overlap, which restricts the flow of exhaled air from the patient into the periphery. When the dial 158 is turned fully in the other direction, for example fully counterclockwise, the cutouts 1702, 1704 overlap, allowing exhaled air to readily vent into the periphery through the holes 1710, 1712 of the barrel valve 502b, 502b. The dial 158 can be set to an infinite number of positions between fully open, counterclockwise, and fully closed, clockwise allowing for infinite adjustments of PEEP.

Figure 18:
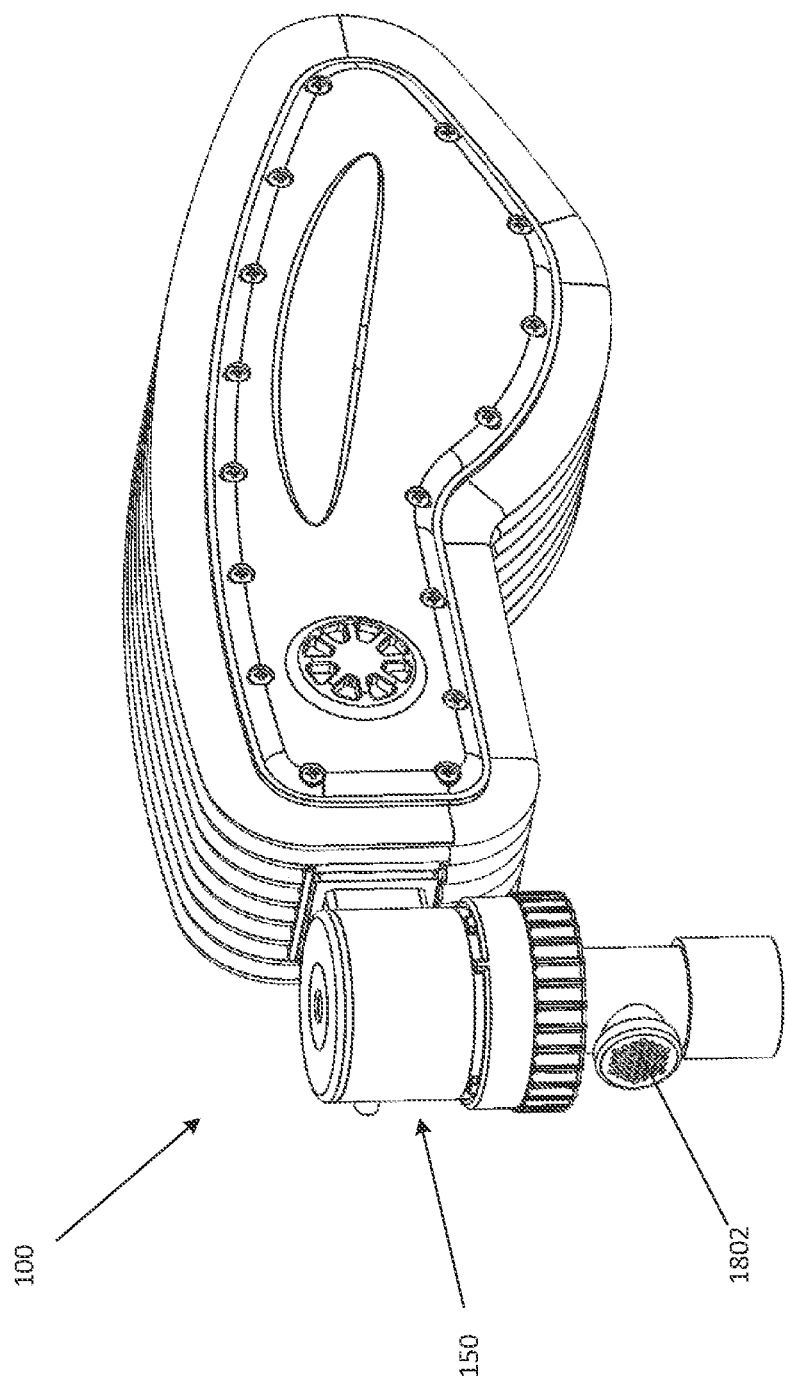
FIG. 18 illustrates a perspective view of an over breathing valve.

FIG. 18 illustrates an example expandable bag device 100 having an over breathing valve 1802 on the connection member 150. The over breathing valve 1802 is a one-way valve that allows a patient to inhale on their own, without the use of the air provided by the expandable bag portion 102. The over breathing valve 1802 may be a diaphragm valve, or any other type of one-way valve commonly known in the art. Exhalation from the patient, or positive pressure from the expandable bag portion 102, would effectively close over breathing valve 1802 during operation.

Inside the over breathing valve 1802 may be an additional valve unit (not shown). The additional valve unit may be duck billed in shape or other potential embodiments. This valve allows the patient to inspire air from the periphery independent of whether or not the user is compressing the expandable bag portion 102 to deliver air to the patient. When the user compresses the expandable bag portion 102, the over breathing valve 1802 closes to prevent loss of inspiratory air from the bag to the periphery.

Figure 19:
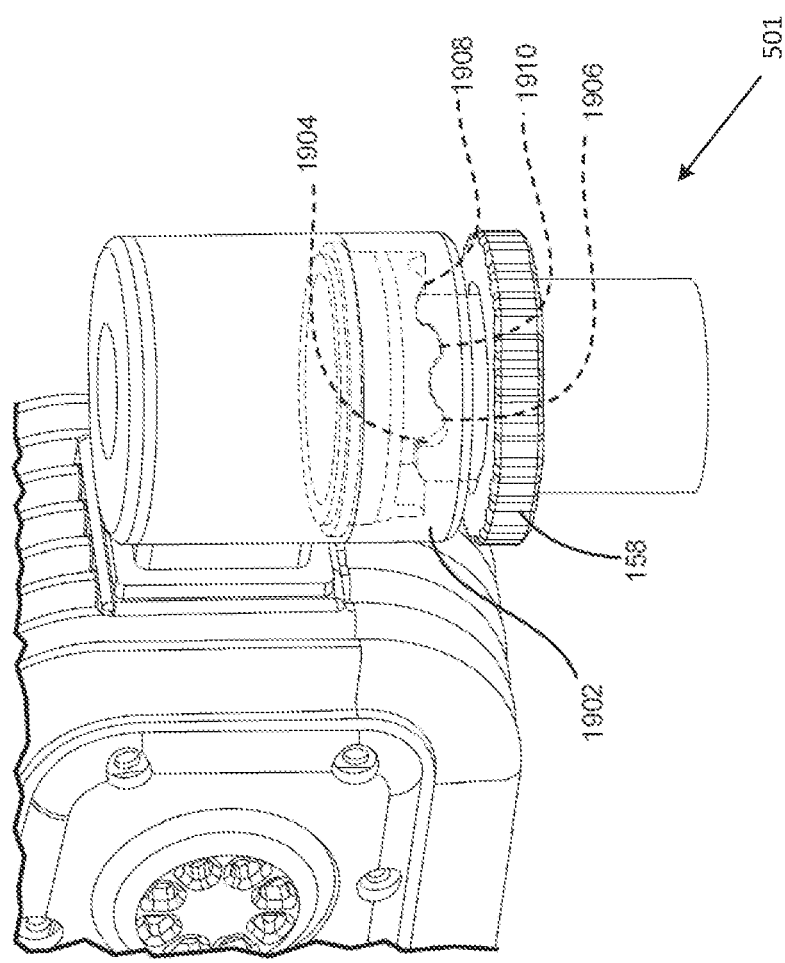
FIG. 19 illustrates an alternative view of a groove and track embodiment of an integrated PEEP valve.

FIG. 19 illustrates an alternative embodiment of a PEEP valve 501. The PEEP valve 501 includes a groove and track embodiment and a dial 158. The dial 158 is used to raise a lifting piece 1902 against a duckbilled-type valve. This is done by moving the relative position of lifting piece 1902 within the groove 1904. In this embodiment there are three potential positions of the lifting piece within the groove: a low position 1906, an intermediate position 1910, and a high position 1908. When the lifting piece 1902 is located in the low position 1906, the lifting piece 1902 is in its lower-most and least restrictive position against the duckbilled valve. This allows for ready exhalation from the patient and generates no PEEP. When the lifting piece 1902 is located in the intermediate position 1910, the lifting piece 1902 is lifted slightly against the duckbilled valve. This requires additional exhaled force in order to vent to the periphery and generates low PEEP. When the lifting piece 1902 is located in the high position 1908, the lifting piece 1902 is lifted tightly against the duckbilled valve. This requires substantial exhaled force in order to vent to the periphery and generates high PEEP. Additional positions within the groove 1904 could be added for additional adjustment of PEEP.

Figure 20:
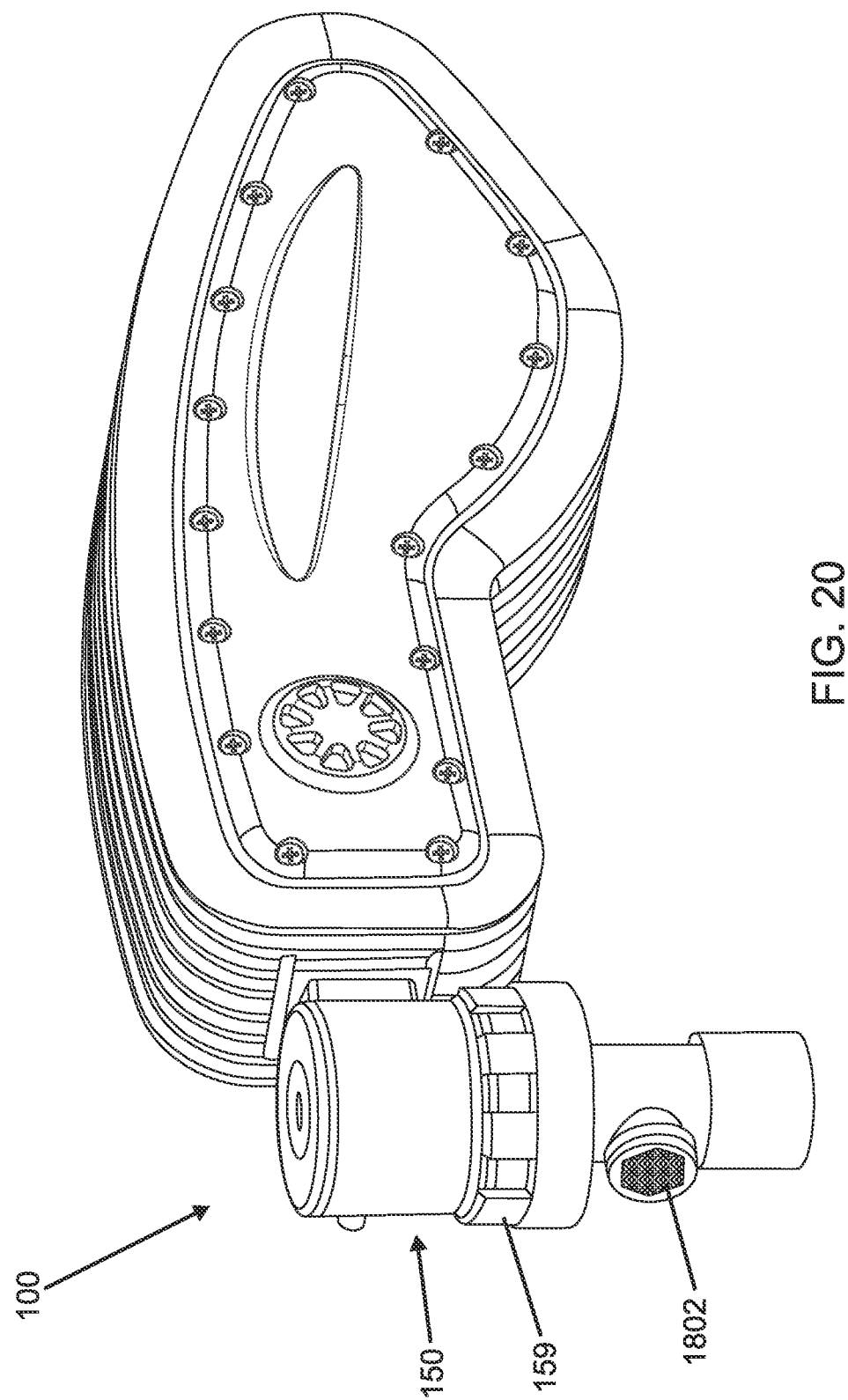
FIG. 20 illustrates an alternative embodiment of a PEEP controller.

FIG. 20 illustrates another embodiment of a PEEP controlling device. A push-button mechanism 159 is used to control the PEEP valve. The push-button mechanism 159 controls the PEEP valve, which is the controlled resistance of the exhaled airflow. The push-button mechanism 159 controls the location of side panels of an internal valve, such as a barrel valve (shown in FIGS. 13-17). When the push-button mechanism 159 is completed pushed to one end, the side panels move closer together, so it is harder for the patient to exhale against. When the push-button mechanism 159 is completed pushed to the alternative end, the side panels move farther apart, so it is easier for the patient to exhale against. The push-button mechanism 159 can have different values such as from 0 to 20 mmHg.

The push-button mechanism 159 may include a plurality of selectable buttons, each selectable button corresponds to a pre-determined value. A user is able to select the button that corresponds to the desired PEEP value.

In an alternative embodiment, the PEEP controlling mechanism, in the form of a push-button mechanism 159, may generate PEEP by applying a plunger (not shown) that applies pressure against the upper aspect of the two-way valve 504. This plunger restricts lifting of the two-way valve 504 resisting exhalation and generating PEEP.

Figure 21:
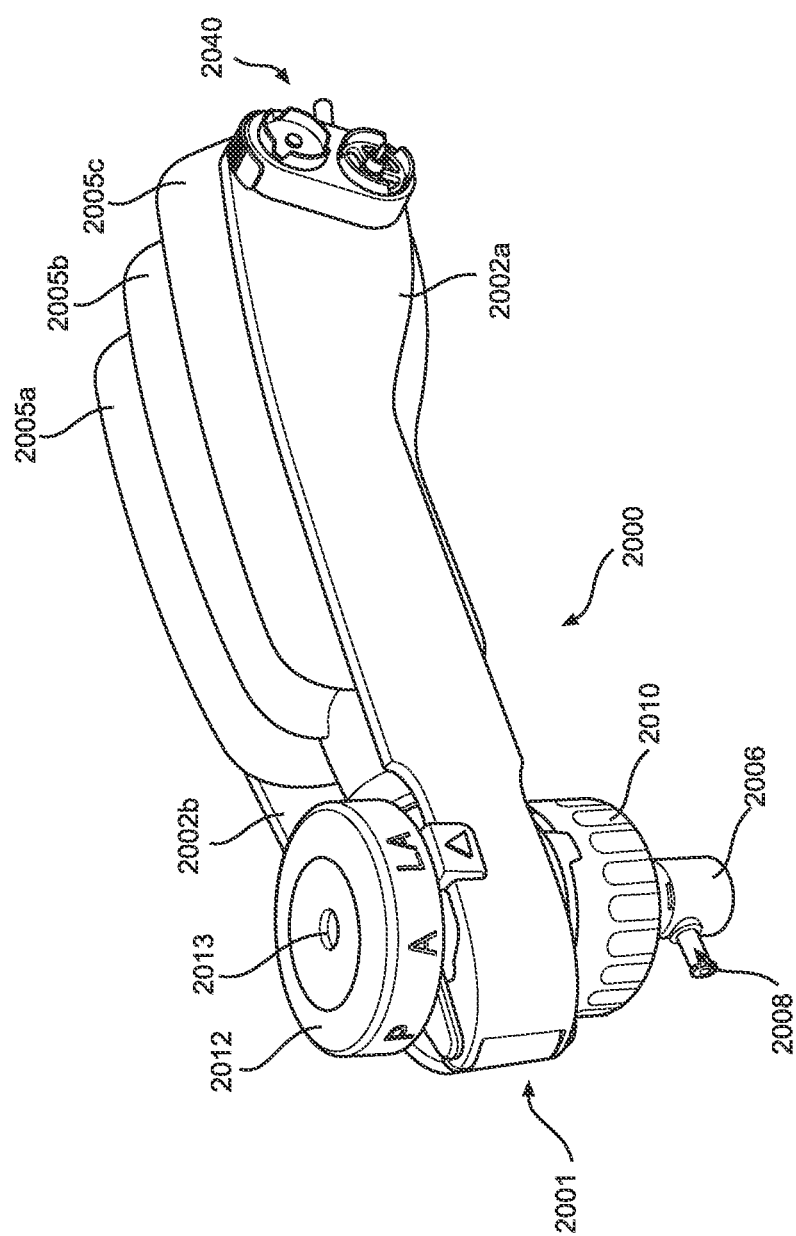
FIG. 21 shows the expandable bag device including an expandable bag.

FIGS. 21-44 illustrate an alternative embodiment of an expandable bag device 2000. FIG. 21 shows the expandable bag device 2000 including an expandable bag 2004 located between a first side panel 2002a and a second side panel 2002b. The expandable bag device 2000 also includes a valve housing member 2001 extending from a first end of the first and second side panels 2002a, 2002b. The valve housing member 2001 may be attached to any type and size of mask or other patient breathing interface device, such as an endotracheal tube or laryngeal mask airway.

The first side panel 2002a and the expandable bag 2004 also includes an air intake mechanism 2040. The air intake mechanism 2040 includes at least one aperture that extends through the first side panel 2002a and into the expandable bag 2004. In an alternative embodiment, the air intake mechanism 2040 is located on the second side panel 2002b, and still further an air intake mechanism 2040 may be located on both the first side panel 2002a and the second side panel 2002b. The air intake mechanism 2040 is described in more detail below, for example at FIGS. 37 and 40.

In an example embodiment, the expandable bag 2004 has an accordion-like design, comprising a plurality of folds 2005a, 2005b, 2005c, such as a bellow, or other similar mechanism. The plurality of folds 2005a, 2005b, 2005c allows the expandable bag 2004 to expand and contract while filling with air, but also being able to occupy a minimal amount of space when not in use. The expandable bag device 2000 includes a first side panel 2002a and a second side panel 2002b that are stiffer than the expandable bag 2004 to allow a user to hold the side panels 2002a, 2002b to compress the expandable bag 2004.

The rigidity of the side panels 2002a, 2002b allow a user to compress the expandable bag 2004, and this combined with the rigidity of the valve housing portion 2001 allows a user to compress the expandable bag 2004 fully and with a single hand while also maintaining a seal with a patient breathing interface around a patient's mouth with the same hand. As described in more detail below, the expandable bag device 2000 allows for single-handed use by a user.

The expandable bag 2004 is a self-inflating bag, in which the expandable bag 2004 takes on an expanded configuration without any external input from the environment. The expandable bag device 2001 includes a spring (not shown) that pushes the side panels 2002a, 2002b away from each other to increase the volume of the expandable bag 2004. The maximum volume of the expandable bag 2004 is controlled by a tidal volume controller within a control dial 2012, as described in more detail below.

The expandable bag device 2000 includes a valve housing member 2001, which is made from a rigid material. The valve housing member 2001 connects the expandable bag 2004 to a patient breathing interface. The valve housing member 2001 includes a pressure relief opening 2013 capped by a control dial 2012. The valve housing member 2001 also includes at least, a PEEP dial 2010, a port 2008, and a mask connection member 2006.

The pressure relief opening 2013 is located at the top of the valve housing member 2001 and is a one-way valve that only lets air flow from inside the valve housing member 2001 to the external environment when the pressure within the valve housing member 2001 is above a predetermined level. This opening 2013 in alternative embodiments may be moved to another location within the valve housing member.

The control dial 2012 simultaneously controls the tidal volume of the expandable bag 2004 and the peak inspiratory pressures that the patient's lungs will experience. In other words, the control dial 2012 restricts how far the first and second side panels 2002a, 2002b of the expandable bag 2004 expand, which determines the volume of air being administered to the patient and the PIP that the patient's lungs will experience. The control dial 2012 includes a plurality of predetermined settings, including for example, large adult, adult, pediatric, and infant. Each of these settings provides an appropriate tidal volume, which is dependent on the size of the patient. As shown in the figure, an indicia, such as "LA," "A," "P," and "I" are used so a user can select the appropriate tidal volume size for the patient. An adult patient generally requires about 500 mL to about 750 mL of a volume of air, a pediatric patient generally requires about 150 mL to about 500 mL of a volume of air, and an infant patient generally requires about 30 mL to about 150 mL of a volume of air.

In order for a user to change the setting of the control dial 2012, the user must press down on the control dial 2012 and simultaneously rotate the control dial 2012 to adjust it to a desired setting. This safety feature prevents a user from accidentally turning the control dial 2012 to an inappropriate volume for the patient. In alternative embodiments, other safety mechanisms are contemplated, such as the use of a latch, or requiring the user to pull upward on the control dial before rotating, or another locking mechanism to prevent an inadvertent adjustment of the tidal volume.

The control dial 2012 includes at least one hollow portion that mates with a tab (not shown) of the first side panel 2002a and another tab on the second side panel 2002b to restrict the width at which the first and second side panels 2002a, 2002b open By doing so, when a user then compresses the expandable bag 2004 from this restricted width to a fully closed position, the volume of air delivered will be consistent and known within a small degree of variance. In an alternative embodiment, the control dial 2012 can permit the first and second side panels 2002a and 2002b to open fully while instead restricting how much the first and second side panels 2002a, 2002b close. The mechanism of control of the control dial 2012 is described in more detail below.

As shown in the figures, the control dial 2012 is located on a top portion of the valve housing member 2001. However, in other embodiments, the control dial 2012 may be located on a vertical side panel or other location of the valve housing member 2001.

Figure 34:
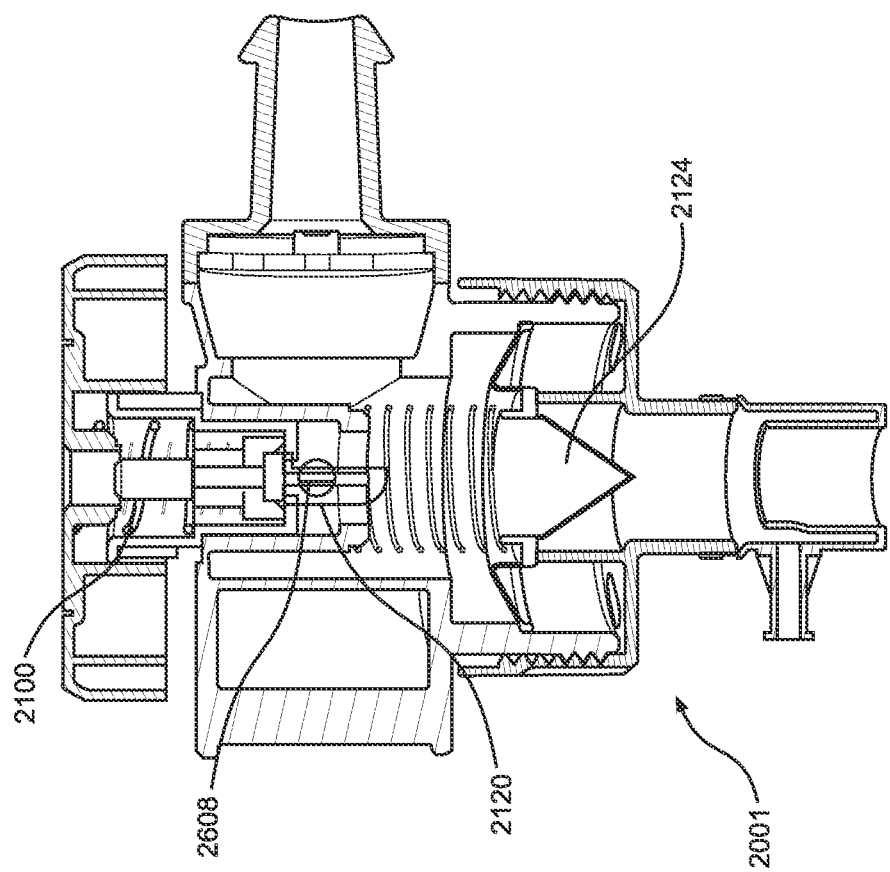
FIG. 34 shows the location of the PIP override tab when viewed through the valve housing member.
Figure 35:
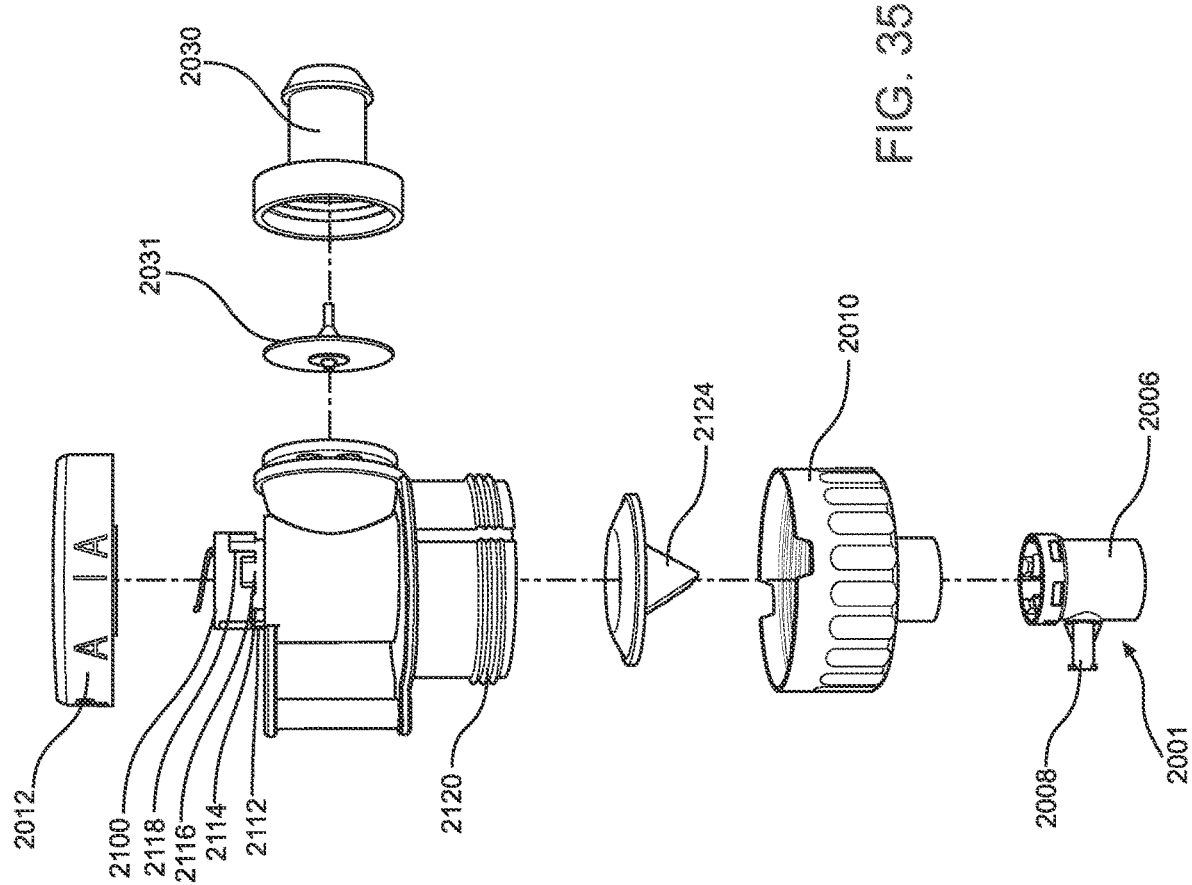
FIG. 35 illustrates an exploded view of the valve housing member.

In addition to controlling tidal volume, the control dial 2012 can also adjust a length of a spring of an internal PIP valve (shown in more detail at FIGS. 34-35). Adjustment of this spring makes it possible to apply a variable amount of downward pressure on the upper aspect of the PIP valve (not shown). When the PIP valve is fully restricted, it will not allow venting of excess pressure (simulating the infinite peak pressure valve that is sometimes needed for large adults). Thus an adjustment of PIP can modify the pressure at which excess pressure is vented from inside the valve housing member 2001 to the periphery.

As the control dial 2012 is rotated to a smaller patient setting, the control dial 2012 will adjust the length of a pop-off spring mechanism and allow the PIP valve to exhaust at lower pressures (a multiplicity depending on chosen settings). In an embodiment, the PIP values are infinite for a large adult, meaning there is no pressure release, 60 cm $H_2O$ for a small adult, and 40 cm $H_2O$ for a child or infant; however other values for relief pressures or sizes or grouping of patients are possible. The control dial 2012 allows for simultaneous adjustment of both tidal volume and PIP to a setting that is desired and appropriate for a given size of patient. In an alternative embodiment the adjustment of tidal volume and PIP may be decoupled.

The PEEP dial 2010 controls an ability of the two-way valve (not shown) to move vertically within the valve housing member 2001. When the PEEP dial 2010 is turned, it changes the pressure required for the patient to exhale. The PEEP dial 2010 can have different values such as from 0 to 20 cm H₂O in slidable increments that may be selectable on the PEEP dial 2010. Alternatively, the PEEP dial 2010 may be adjustable in discrete increments, such as increments of 5 cm H₂O or less.

The port 2008 may be used for a plurality of connections, including for example a medication injection device and end-tidal CO₂ detector. The port 2008 is located between the two-way valve and the mask connection member 2006. This allows for monitoring of CO₂ release from the patient during resuscitation or for the administration of medication directly to a patient's airway, without having to go through one of the valves of the valve housing member 2001.

The valve housing member 2001 is made from a rigid material, and in combination with a rigidity of the first side panel 2002a and the second side panel 2002b allows a user to hold the expandable bag device 2000 in one hand. A user is able to compress the expandable bag 2004 with one hand, while maintaining a seal of a mask on a patient's face with the same hand. The stiffness of the valve housing member 2001 and the first and second side panels 2002a, 2002b allows for single-handed use of the expandable bag device 2000.

Figure 22:
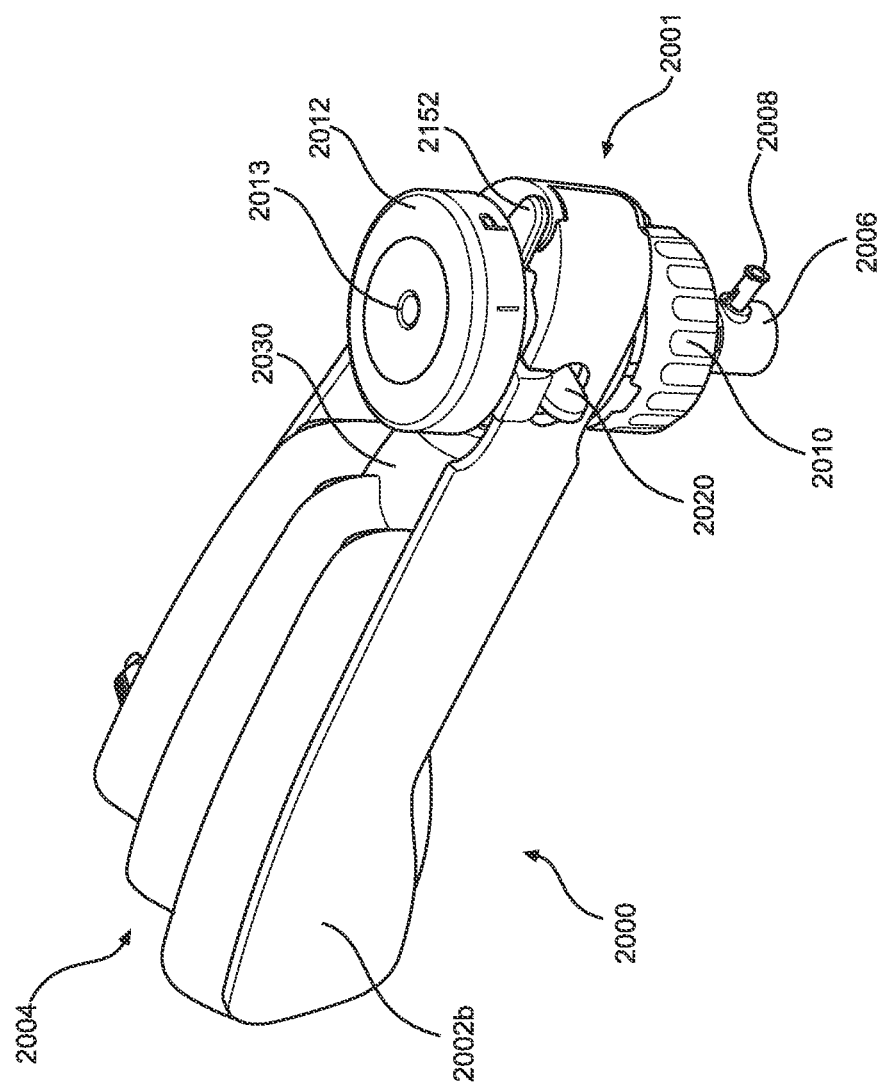
FIG. 22 illustrates a rear view of the expandable bag device.

FIG. 22 illustrates a alternative view of the expandable bag device 2000. The expandable bag 2004 is attached to the valve housing member 2001 via a bag connection member 2030 that allows air to flow from the expandable bag 2004 through the valve housing member 2001 and to the patient. The valve housing member 2001 is connected to the first and second side panels 2002a, 2002b.

The expandable bag device 2000 is designed so the compression of the expandable bag 2004 by the first and second side panels 2002a, 2002b, occurs along a plane that is parallel to the plane of a mask on a patient. Still further, the plane that the expandable bag 2004 compresses along is normal or perpendicular to the mask connection member 2006. In other words, in an expanded configuration, the expandable bag 2004 is larger at an end opposite the valve housing member 2001 than an end adjacent the valve housing member 2001.

Also shown is a PIP override tab 2020. The PIP override tab 2020 has two configurations. In a first configuration, the PIP override tab 2020 is in an override state, where no air is allowed to vent through the PIP valve, simulating an infinite PIP value. In a second configuration, when the PIP override tab 2020 is rotated such as 90° or 180°, the PIP override tab 2020 is not in an override state, where air is allowed to vent through the pressure relief opening 2013. The side panel 2002b is shaped so as to hang slightly over the PIP override tab 2020 when the expandable bag 2004 is in an expanded state. In this embodiment, a user must first fully compress the bag in order to rotate the PIP override tab 2020 into a locked or unlocked position. This serves as a safety mechanism to prevent unintentional manipulation of the PIP override tab 2020.

Figure 23:
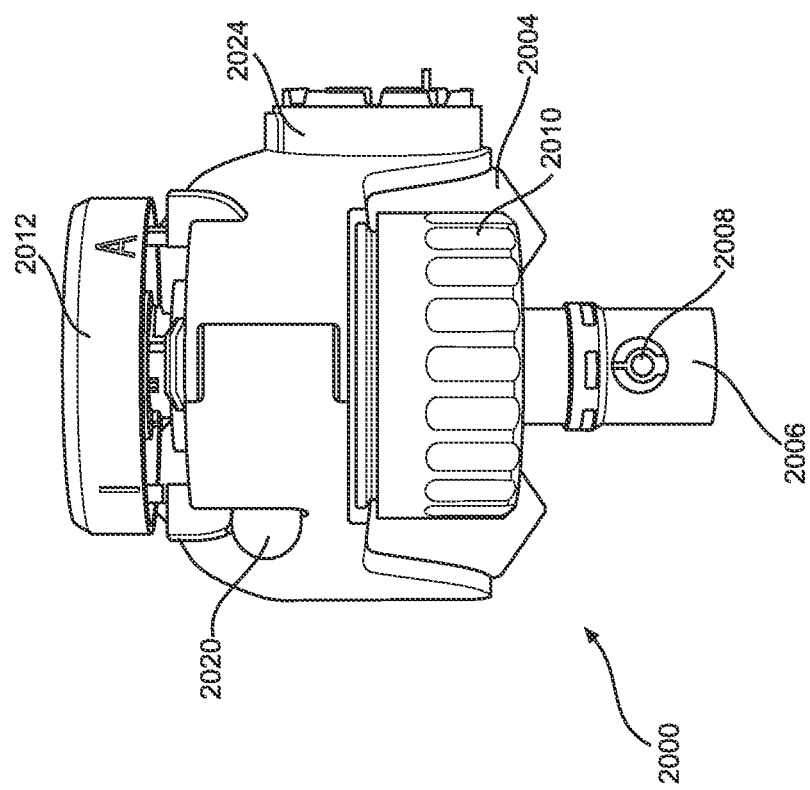
FIG. 23 illustrates an example embodiment of the valve housing member.

FIG. 23 illustrates an example embodiment of the valve housing member 2001. The valve housing member 2001 includes the control dial 2012 at a first end, such as the top of the valve housing member 2001 when oriented on a patient in use, a mask connection member 2006 at a bottom end, and the PIP override tab 2020, a manometer port (not shown), the PEEP dial 2010, and the medication port or end-tidal CO₂ connection port 2008 located therebetween.

A manometer port (not shown) can be used to indicate the internal pressure levels of the expandable bag device 2000. In this embodiment the manometer port 2022 extends from the middle portion of the valve housing member 2001, however in other embodiments, the manometer port 2022 may extend from any other portion of the valve housing member 2001 or the bag connection member 2030.

The control dial 2012 surrounds an internal mechanism (not shown) that is capable of simultaneously controlling tidal volume and PIP. The internal mechanism of the control dial 2012 is shown in more detail at FIGS. 30, 32, and 34. The control dial 2012 includes settings identified by indicia to indicate which type of patient the expandable bag device 2000 is being used for. For example, "I" indicates infant use, "P" indicates pediatric use, and "A" indicates adult use. In an embodiment, the control dial 2012 may include additional settings, such as a large adult. The control dial 2012 provides for different tidal volumes and PIP within a given patient size class.

As shown in FIG. 23, the expandable bag 2004 is in an expanded configuration. An end of the expandable bag 2004 located away from the valve housing member 2001 has a width that is greater than a width of the expandable bag 2004 located near the valve housing member 2001.

The mask connection member 2006 extends from a second end of the valve housing member 2001 and is capable of connecting to a mask or other patient interfacing device, such as an endotracheal tube or laryngeal mask airway.

Figure 24:
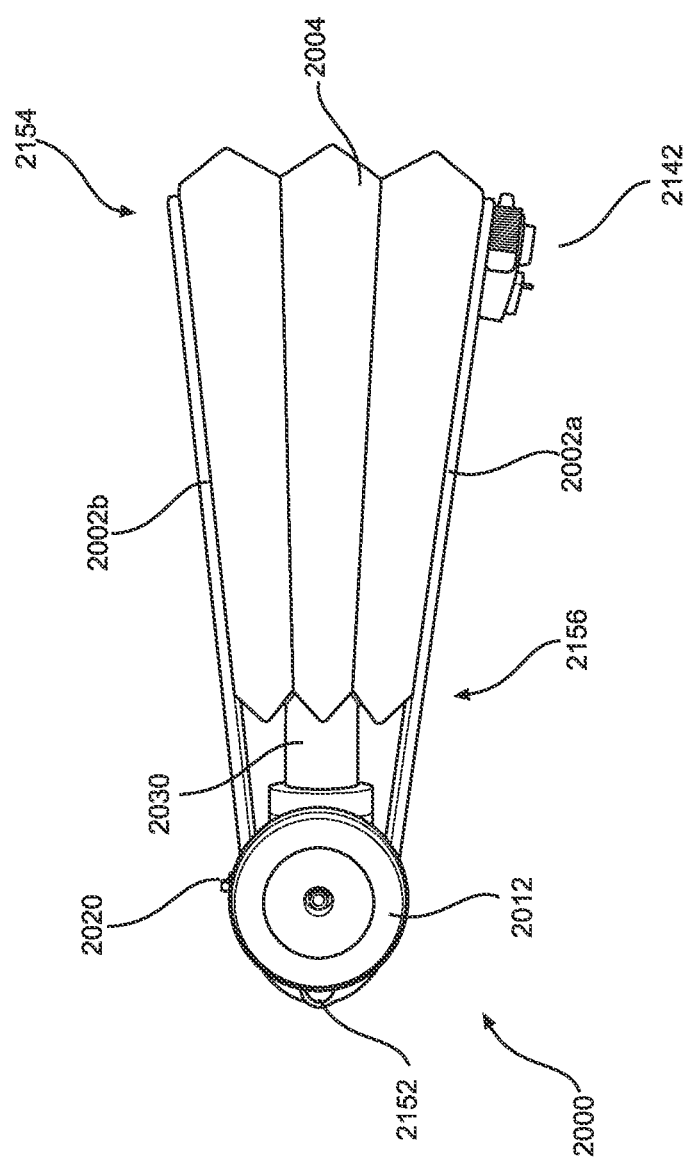
FIG. 24 illustrates a top view of the expandable bag device in an expanded configuration.

FIG. 24 illustrates a top view of the expandable bag device 2000 in an expanded configuration. As shown, the expandable bag 2004 has a generally triangular-shape when in the expanded configuration. The bag could assume other shapes such as spherical, ovoid, square, rectangular, or another polygonal shape. An end 2154 of the expandable bag 2004 opposite the valve housing member 2001 expands more than an end 2156 adjacent the valve housing member 2001.

A bag connection member 2030 is shown, which provides fluid communication between the expandable bag 2004 and the valve housing member 2001 to provide air to a patient. The bag connection member 2030 can also include a valve 2031 that prevents back flow of air from the valve housing member 2001 to the expandable bag 2004.

The valve housing member 2001 may also include a light 2152. To aid the user in preventing hyperventilation, or more specifically from inducing hyperventilation, the valve housing member 2001 includes a battery-powered, blinking light 2152. The light 2152 works in conjunction with the control dial 2012, blinking at a cadence specific to the tidal volume and PIP chosen on the control (infant, pediatric, adult, large adult) to indicate to the user the rate that is appropriate to deliver air to the patient. Additionally, the duration of the light blink indicates the time that it should take for the user to deliver air to the patient.

The light 2152 may blink at different speeds for different sizes of patients. For example, the light 2152 may blink every 1-2 seconds for an infant, 2-3 seconds for an infant or pediatric patient, and 5-6 seconds for an adult. However, other time periods are contemplated. The blinking light indicates to a user how often to compress the expandable bag 2004.

The light 2152 can be attached to the control dial 2012 via a conductive band that receives an input depending on what size of patient is selected on the control dial 2012. The light 2152 can determine the cadence at which the light 2152 blinks to display the appropriate timing for the user to squeeze the bag and give air to the patient. The light 2152 may also blink for a duration of time, such as 1 second, which corresponds to how long a user should take to fully compress the expandable bag 2004.

In an embodiment, the light 2152 can blink in a first color when the expandable bag device 2000 is being used properly by the user. When a user is not using the expandable bag device 2000 properly, the light 2152 can blink in a different color. For example, when the expandable bag 2004 is being compressed at a correct speed and correct duration, the light 2152 blinks with a green color. If the expandable bag 2004 is being compressed too quickly or too slow, the light 2152 may blink a red color.

The light 2152 may also be associated with a sound, such as an alarm or metronome. If the expandable bag 2004 is being compressed too quickly or too slow, in addition to or instead of a red colored blinking light, an alarm may sound. Still further, only a sound may be utilized to indicate the correct cadence, rate, compression time, or signal errors or provide other feedback to the user.

The light 2152 may be an LED or other type of light powered by a battery, such as a rechargeable battery or a non-rechargeable battery, or powered by a mechanical charging system utilizing the compression of the expandable bag 2004 to power the light 2152.

Figure 25:
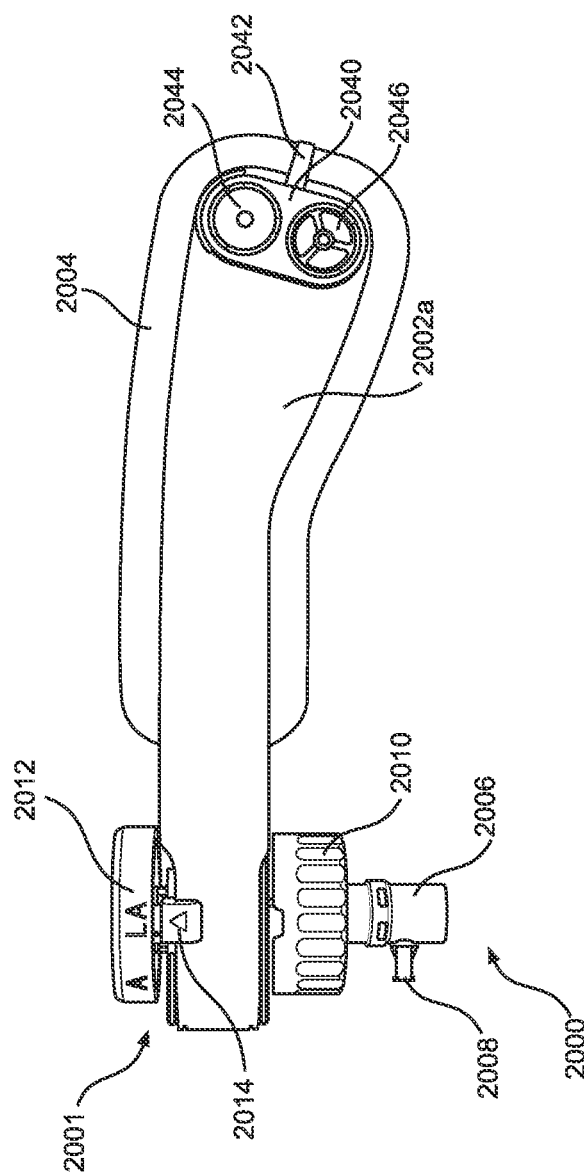
FIG. 25 illustrates an alternative side view of the expandable bag device.

FIG. 25 illustrates an alternative side view of the expandable bag device 2000. As discussed above, the expandable bag device 2000 includes an expandable bag 2004 connected to a valve housing member 2001. The expandable bag device 2000 is shown in a compressed embodiment, where the expandable bag device 2000 takes up minimal space.

The first side panel 2002a also includes an air intake mechanism 2040. The air intake mechanism 2040 includes an oxygen exhaust valve 2044, an ambient air inlet valve 2046, and an oxygen inlet port 2042. The air intake mechanism 2040 allows air to flow into the expandable bag 2004.

The air intake mechanism 2040 includes the oxygen inlet port 2042, the oxygen exhaust valve 2044, an air inlet valve 2046, an expandable bag inlet valve (not shown), and a hyperventilation override slide (not shown).

In use, supplementary oxygen may be provided to the expandable bag 2004 via the oxygen inlet port 2042. The air intake mechanism 2040 includes a check valve system that allows the user to add supplementary oxygen to the ambient air within the expandable bag 2004 at a controlled rate by only letting a specified volume of oxygen into the expandable bag 2004 over time, while excess oxygen is exhausted through an oxygen exhaust valve 2044 to the periphery. This system regulates the rate at which oxygen and ambient air are allowed into the expandable bag regardless of the rate at which oxygen is set to flow into the oxygen inlet port 2042 such as at 10 L/min, 15 L/min, etc.

In a further embodiment, an auditory indicator may provide a first sound while the expandable bag 2004 is inflating, and a second sound when the expandable bag has reached maximum volume.

Figure 26:
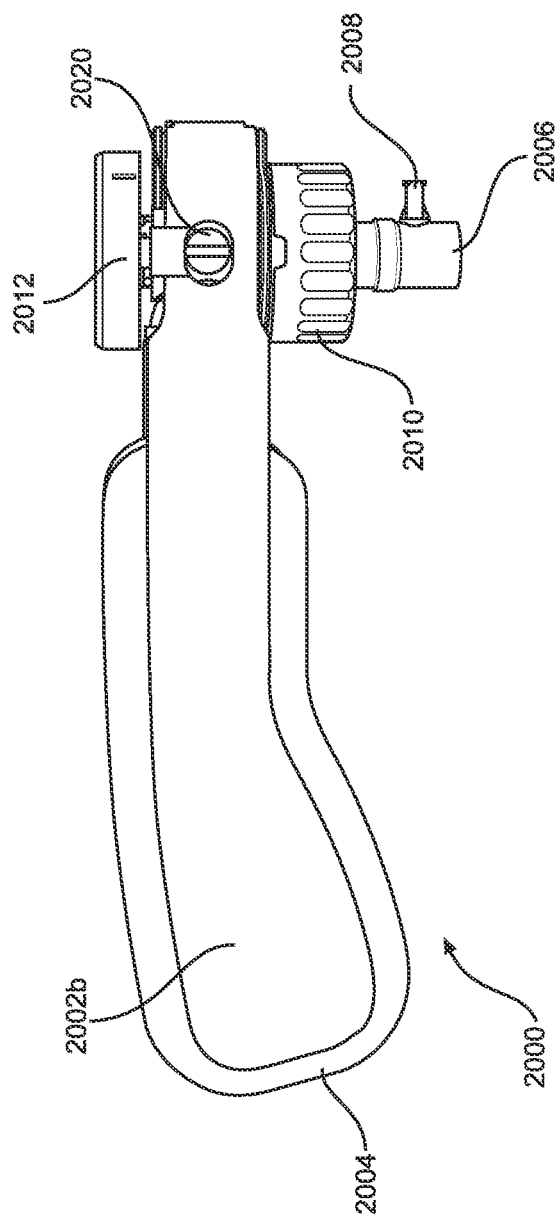
FIG. 26 shows another side view of the expandable bag device.

FIG. 26 shows another side view of the expandable bag device 2000. The expandable bag device 2000 is shown in a compressed embodiment, where the expandable bag device 2000 takes up minimal space. Further, the second side panel 2002b does not include an air intake mechanism 2040. However, in other embodiments, the second side panel 2002b may include the air intake mechanism 2040 or a duplicate or alternative air intake mechanism.

Figure 27:
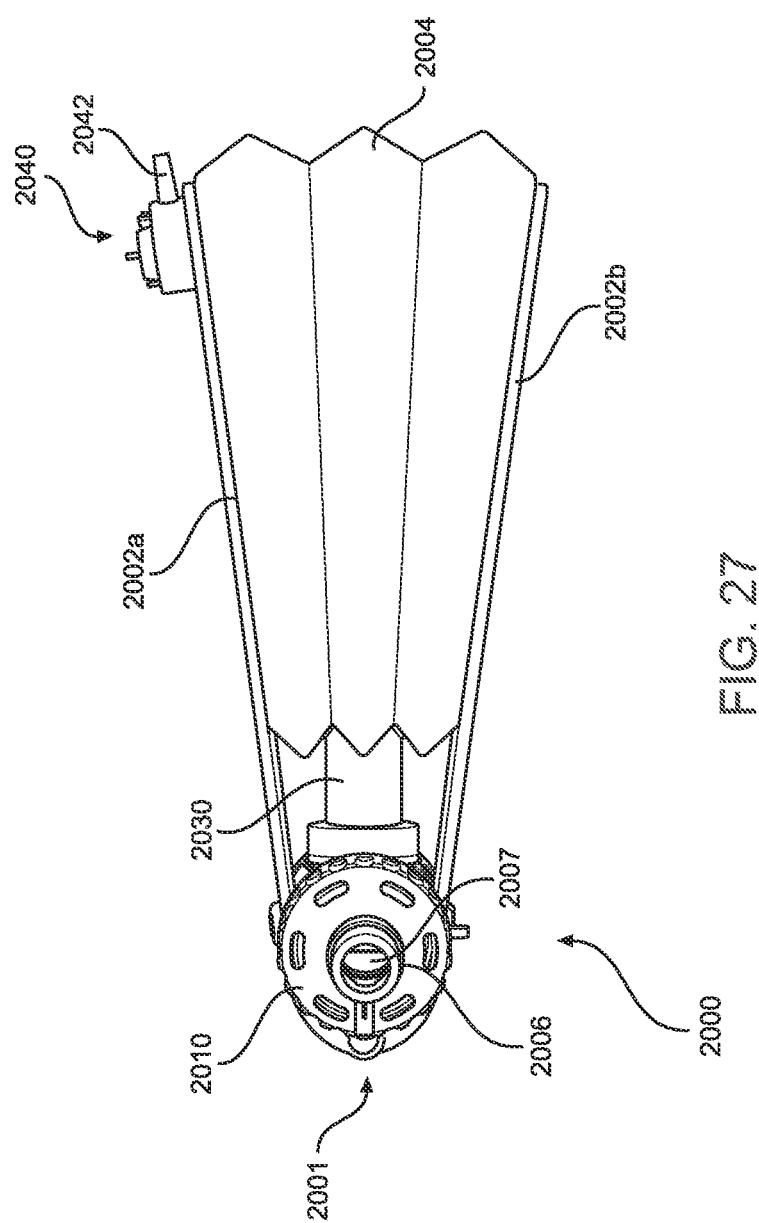
FIG. 27 illustrates a bottom view of the expandable bag in an expanded configuration.

FIG. 27 illustrates a bottom view of the expandable bag device 2000 in an expanded configuration. The valve housing member 2001 is connected to the expandable bag 2004 via the bag connection member 2030, which includes a one-way valve (not shown) that allows air to flow from the expandable bag 2004 to the valve housing member 2001. Also shown is a mask connection lumen 2007 within the mask connection member 2006, which is in fluid communication with the expandable bag 2004 via the bag connection member 2030 to deliver air to a patient through a mask or other patient interface device (not shown).

Figure 28:
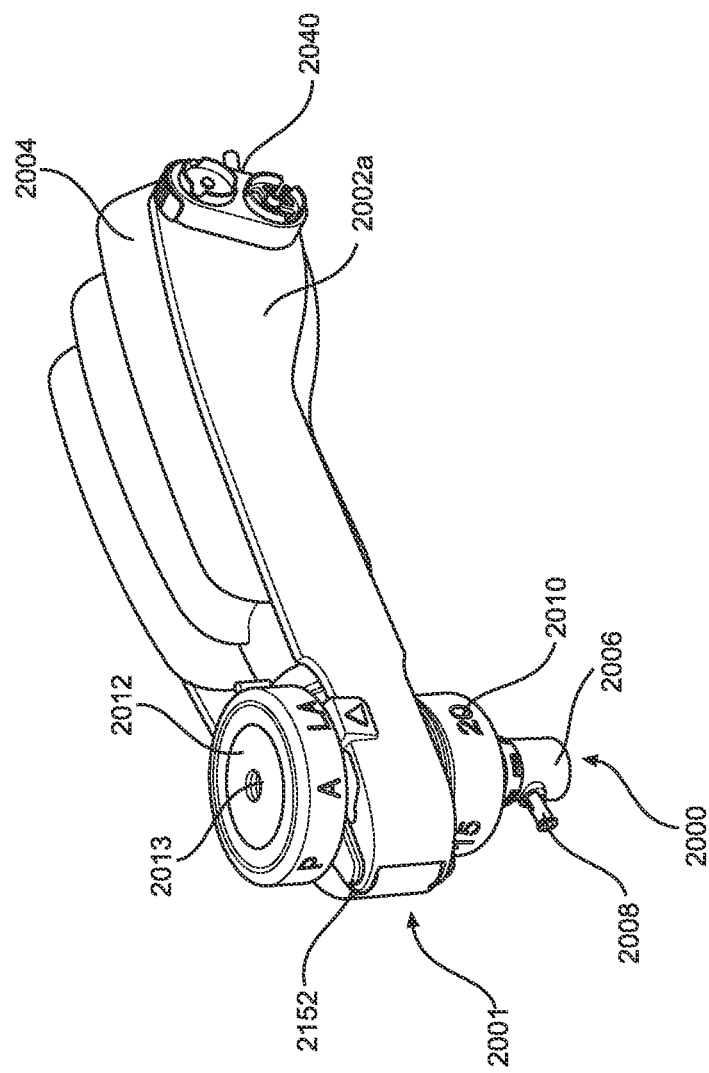
FIG. 28 shows another view of the expandable bag device.

FIG. 28 shows another view of the expandable bag device 2000. As described above, the expandable bag device 2000 includes the valve housing member 2001 in fluid communication with the expandable bag 2004. The air intake mechanism 2040 is located on a first side panel 2002a.

Figure 29:
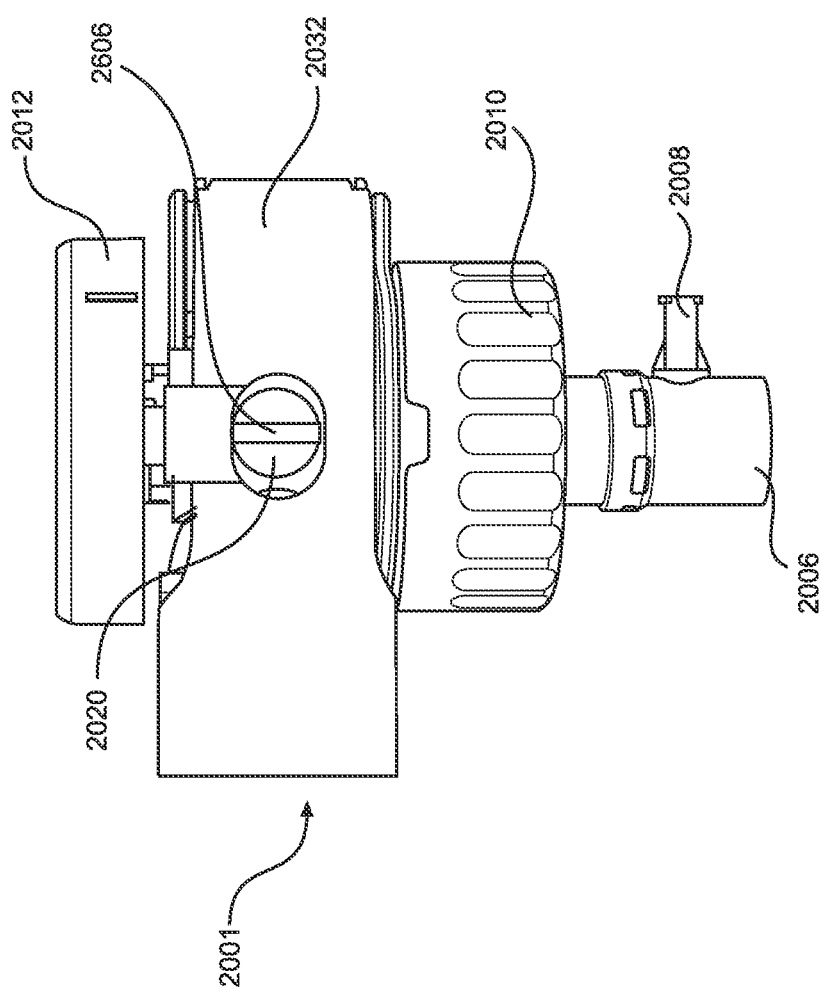
FIG. 29 illustrates an isolated view of the valve housing member.

FIG. 29 illustrates an isolated view of the valve housing member 2001. The valve housing member 2001 is shown in a use orientation. A mask connection member 2006 is located at a bottom end of the valve housing member 2001, and the control dial 2012 is located at a top end of the valve housing member 2001.

A body 2032 of the valve housing member 2001 is located below the control dial 2012, and houses at least the light (not shown) and the PIP override tab 2020. Below the body 2032 is the PEEP dial 2010. A port 2008 is located near the mask connection member 2006, although its exact location may be anywhere along the path of the air coming from the expandable bag (not shown) and below the two-way valve. In an embodiment, the port 2008 may be a medication port, which allows direct administration to a patient without having to administer the medication through any of the valves.

The PIP override tab 2020 has a tab 2606 that is pointing along a plane perpendicular to the expandable bag (not shown). The tab 2606 can be rotated by a user to point along a plane that extends perpendicular to the valve housing member 2001, which creates an infinite PIP valve.

Figure 30:
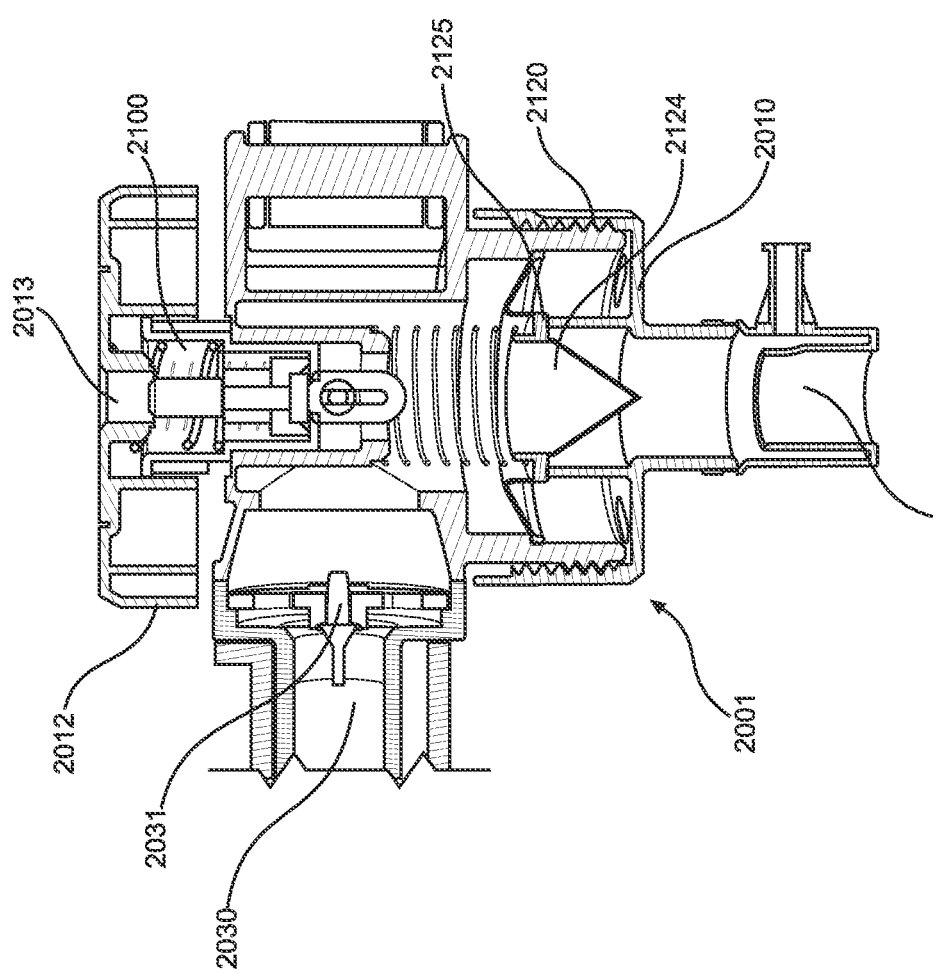
FIG. 30 illustrates a cutaway view of the valve housing member.

FIG. 30 illustrates a cutaway view of the valve housing member 2001. In particular, the cutaway view of the valve housing member 2001 illustrates a two-way valve 2124 located centrally in the mask connection lumen 2007. The two-way valve 2124 functions to deliver air from the expandable bag (not shown) to the patient, while also providing a PEEP functionality.

In an embodiment, the two-way valve 2124 is a duckbilled valve that includes two flaps that meet each other in a center of the mask connection lumen 2007 and pointing in a direction towards a mask (not shown). In another embodiment, the two-way valve 2124 is an umbrella valve that is secured within the mask connection lumen 2007.

The desired PEEP value is controlled by the PEEP dial 2010 and can be adjusted to a predetermined PEEP value as desired by the user. The two-way valve 2124 in combination with a lifting piece 2125 creates PEEP to maintain predetermined pressure in the lungs of the patient. The two-way valve 2124 allows air from the expandable bag 2004 to be provided to the patient and forces exhaled air to lift the two-way valve 2124 off of the lifting piece 2125.

The PEEP dial 2010 controls the PEEP value via an internal thread 2120. For example, rotating the PEEP dial 2010 increases or decreases the tension of a lifting piece 2125 against the two-way valve 2124, which effectively changes the force required for a patient to exhale air through the PEEP valve. No tension between the lifting piece 2125 results in no generation of PEEP. Low tension at the connection of the lifting piece 2125 and the two-way valve 2124 results in a low PEEP value, while higher tension between the lifting piece 2125 and the two-way valve 2124 results in a higher PEEP value. The PEEP valve and mechanism is shown in more detail at FIG. 35.

At higher breath pressures coming from the patient, the pressure will surmount the PEEP value, but as the breath pressures decrease, the two-way valve 2124 returns to its resting position against the lifting piece 2125, which forces the pressure to be maintained within the patient's lungs. This allows for easier administration of subsequent breaths into the patient, thus more efficient and effective bagging.

Also shown is the PIP control mechanism 2100, which is also controlled by the control dial 2012. By adjusting the control dial 2012, the pressure at which air vents to the periphery is changed and the tidal volume provided by the expandable bag 2004 is changed. The adjustment of the control dial 2012 modifies the pressure at which excess pressure is vented from inside the expandable bag device 2000 to the periphery.

When the PIP value is fully restricted, it will not allow venting of excess pressure (simulating the infinite peak pressure valve that is sometimes needed for certain clinical scenarios). As the control dial 2012 is rotated and then released to the various patient settings, the height of the control dial 2012 will be restricted by the use of inverted wells 2112, 2114, 2116, 2118. The relative height of these inverted wells 2112, 2114, 2116, 2118 will adjust the length of the pop-off spring 2119 and allow the pop-off valve to exhaust at a variety of pressures. Predetermined PIP values are infinite for a large adult, 60 cm $H_2O$ for a small adult, and 40 cm $H_2O$ for a child or infant; however, other values are possible.

The PIP control mechanism 2100 includes at least four settings, or inverted wells 2112, 2114, 2116, 2118, which correspond to the predetermined PIP values. When the control dial 2012 is turned, a desired setting is selected. In an embodiment, a first inverted well 2112 has a short length, and corresponds to a PIP value of 60 cm of $H_2O$ for adults. A second inverted well 2114 has a medium length, and corresponds to a PIP value of 40 cm of $H_2O$ for pediatric patients. A third inverted well 2116 has a long length, and corresponds to a PIP value of 40 cm of $H_2O$ for infants. A fourth inverted well 2118 has a shortest length and corresponds to an infinite PIP value.

The PIP control mechanism 2100 includes four inverted wells, where each inverted well corresponds to the inverted wells 2112, 2114, 2116, 2118. The control dial 2012 also includes a spring which requires a predetermined amount of force to turn the control dial 2012. In an alternative embodiment the same mechanism could be achieved using right-side-up wells. This would particularly apply in an embodiment wherein the control dial 2012 is pulled upward and rotated to adjust instead of being depressed and rotated to adjust.

The two-way valve 2124 also provides additional functionally, by restricting a flow of fluids back into the valve housing member 2001. For example, if a patient vomits, the two-way valve 2124 prevents fluid from entering the valve housing member 2001 and directs it out of the valve housing member 2001, similar to the direction air flows as a result of the PEEP setting.

Figure 31:
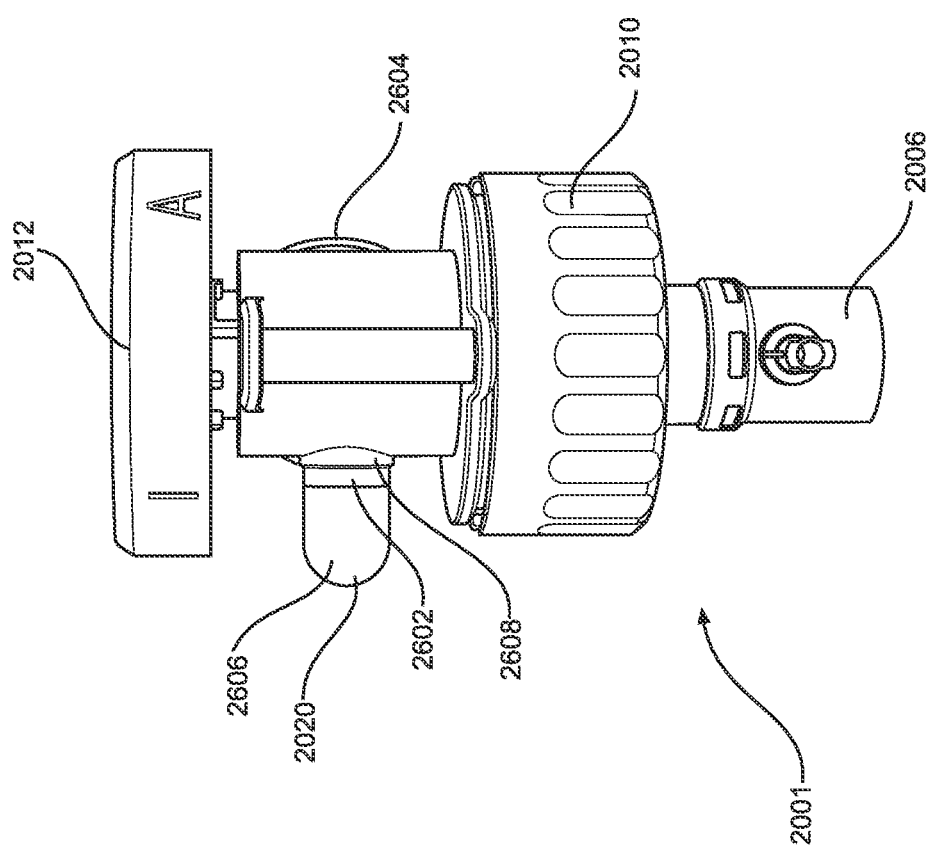
FIG. 31 illustrates a view of the valve housing member highlighting the PIP override tab.

FIG. 31 illustrates a view of the valve housing member 2001 highlighting the PIP override tab 2020. When a user activates the PIP override tab 2020, the PIP valve will not activate and thus at no pressure will air vent through the pressure relief opening. The PIP override tab 2020 extends out from a center of the valve housing member 2001. In a first embodiment, when the PIP override tab 2020 is in an override state, the tab 2606 is pointed towards the expandable bag 2004. In a second embodiment, when the PIP override tab 2020 is not in an override state, the tab 2606 is pointed in a direction opposite the expandable bag 2004, such as in line with the mask connection member 2006. However, the direction of the tab 2606 corresponding to the first or second embodiment should not be seen as limiting, as other directions are possible.

The user is able to rotate the PIP override tab 2020 as desired, for example from the first embodiment to the second embodiment, and back, if needed. The PIP override tab 2020 has a tab 2606, and an extension portion 2602 connecting to a concentric spring mechanism 2604. An end 2608 of the extension portion 2602 has a semicircular or other shape that mates with a corresponding shape of the PIP valve (not shown).

In an embodiment, the PIP override tab 2020 and semi-circular mating portion do not form concentric semicircles and do not interact allowing air to vent from the top of the device at the desired pressure. When the PIP override tab 2020 is in the override state, a cutout in the extension portion 2602 and the semicircle portion of the PIP override tab 2020 interact and become concentric. The semicircular mating portion is now locked in position, closing off the pressure relief opening at the top of the valve housing member 2001, and not allowing air to vent out (or setting the PIP valve to an infinite pressure). In an embodiment the PIP override tab may be external to the valve housing member 2001 and function by being lifted and applying downward force on the upper aspect of the control dial 2012 to compress the spring over the rod 2602 and prevent venting of excess pressures.

Figure 32:
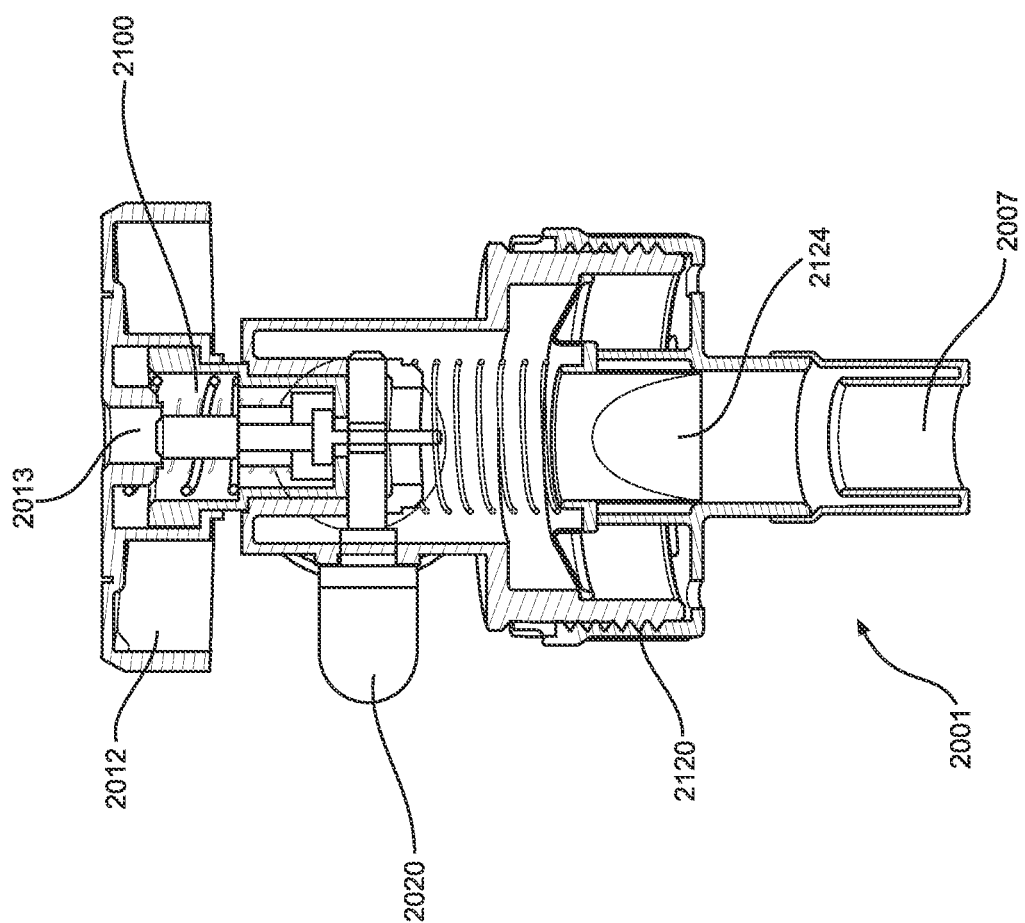
FIG. 32 illustrates a cutaway view of the valve housing member.

FIG. 32 illustrates a cutaway view of the valve housing member 2001 with a different style of two-way valve 2124. The valve housing member 2001 also includes the control dial 2012, which controls the tidal volume of the expandable bag (not shown) and the PIP inverted wells 2112, 2114, 2116, 2118. Further shown is the internal threads 2120 which dictates the amount that the two-way valve 2124 is allowed to move, and provides PEEP.

Figure 33:
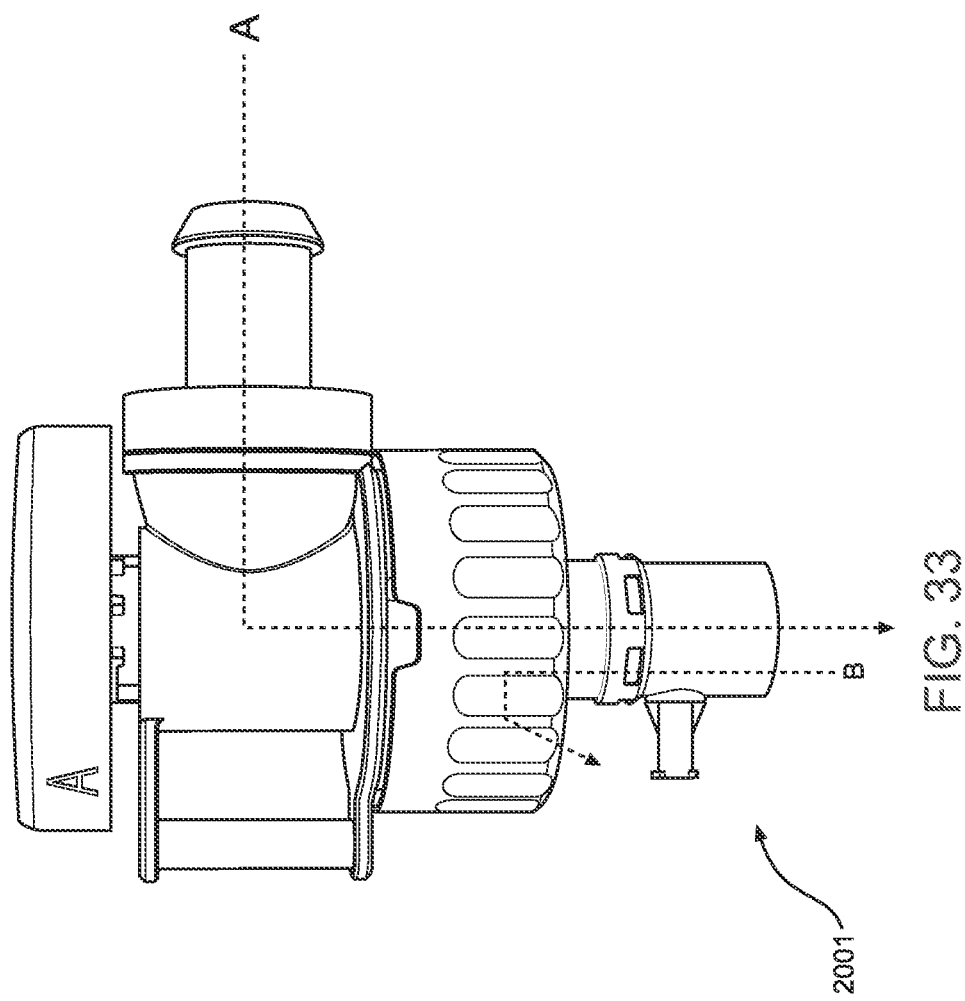
FIG. 33 illustrates a partial cutaway view of the valve housing member.

FIG. 33 illustrates the valve housing member 2001 and indicating a direction that air flows. Air flow follows the path A from the inflatable bag (not shown) through the bag connection member 2030, into the valve housing member 2001, through the mask connection member 2006, and eventually to the patient through a mask (not shown).

Upon expiration, the patient exhales, and the air follows path B. The exhaled air moves back through the mask connection member 2006 and out through an opening created by moving the two-way valve within the valve housing member 2001.

FIG. 34 shows the location of the PIP override tab 2020, when viewed through the valve housing member 2001. As described above, the PIP override tab 2020 has a tab (not shown), a rod (not shown) connecting to a concentric spring mechanism (not shown). An end 2608 of the rod has a circular shape that mates with a corresponding shape of the PIP mechanism (not shown).

FIG. 35 illustrates an exploded view of the valve housing member 2001. The control dial 2012 is located at an end of the valve housing member 2001; however, the exact location of the control dial 2012 is variable. As the control dial 2012 rotates it communicates with one of the inverted wells 2112, 2114, 2116, 2118, which correspond to a predetermined PIP value. A spring (not shown) maintains the control dial 2012 in the correct position, such that to turn the control dial 2012 the strength of the spring must be overcome.

The control dial 2012 also controls the tidal volume provided by the expandable bag. The control dial 2012 includes a tidal volume controller that communicates with the first side panel 2002*a* and the second side panel 2002*b* to control the width at which the panels are allowed to expand. In a first configuration, a tidal volume controller has an octagonal shape (four pairs of settings) that restrict the width that the first side panel 2002*a* and the second side panel 2002*b* are allowed to expand. A hinge located with the expandable bag 2004 forces the first side panel 2002*a* and the second side panel 2002*b* to open, and the tidal volume controller determines how much the first side panel 2002*a* and the second side panel 202*b* are allowed to open.

In an alternative configuration, the tidal volume controller restricts the width that the first side panel 2002*a* and the second side panel 2002*b* are allowed to close relative to each other. The hinge located with the expandable bag 204 forces the first side panel 2002*a* and the second side panel 2002*b* to open, and the tidal volume controller determines how much the first side panel 2002*a* and the second side panel 2002*b* are allowed to close when being compressed by a user.

The bag connection member 2030 includes a valve 2031 that only allows air to from the expandable bag to the valve housing member 2001. The valve 2031 prevents any backflow of air from the valve housing member 2001 into the expandable bag. In an embodiment, the valve 2031 is an umbrella valve.

The two-way valve 2124 allows air to flow to the patient from the valve housing member 2001 in a first direction and forces exhaled air from the patient to exhaust into the periphery. As shown, the PEEP dial 2010 is located within an internal thread 2120, and the extent to which the lifting piece 2125 is allowed to move vertically within the valve housing member 2001 is dictated by the location of the PEEP dial 2010 along the internal thread 2120. In an embodiment as shown, the two-way valve 2124 is a duck-billed valve, and in alternative embodiments, the two-way valve 2124 may be an umbrella valve.

The PEEP dial 2010 surrounds the location of the two-way valve 2124. The PEEP dial 2010 is capable of being turned by a user to a desired PEEP value, which corresponds to amount of tension between the lifting piece 2125 and the two-way valve 2124. The force required by exhaled air to move the two-way valve 2124 off of the lifting piece 2125 corresponds to the PEEP value selected.

Figure 36:
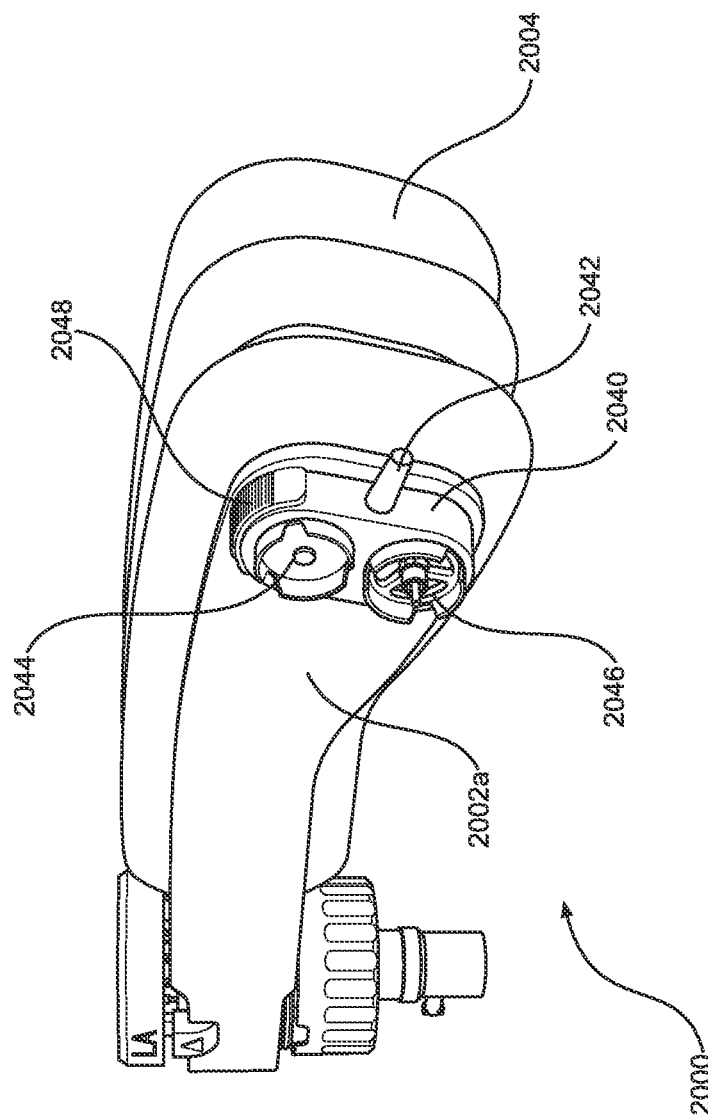
FIG. 36 shows the expandable bag device with the expandable bag in an expanded configuration.

The two-way valve 2124 also prevents backflow of fluids into the valve housing member 2001. The two-way valve 2124 prevents fluid from entering the valve housing member 2001 and directs fluid out of the valve housing member 2001, similar to the direction air flows as a result of the PEEP setting FIG. 36 shows the expandable bag device 2000 with the expandable bag 2004 in an expanded configuration. The first side panel 2002*a* includes the air intake mechanism 2040. The air intake mechanism 2040 includes an oxygen inlet port 2042, an oxygen exhaust valve 2044, an air inlet valve 2046, a bellows inlet valve (not shown), and a hyperventilation override slide 2048.

The oxygen inlet port 2042 is capable of connecting to an oxygen source, to provide oxygen to the expandable bag. The oxygen exhaust valve 2044 vents excess oxygen from the air intake mechanism 2040 to the periphery when the pressure within the air intake mechanism 2040 is too high. The air inlet valve 2046 allows ambient air to enter the air intake mechanism 2040, and ultimately into the expandable bag 2004 via one or more adjustable apertures (not shown).

Figure 37:
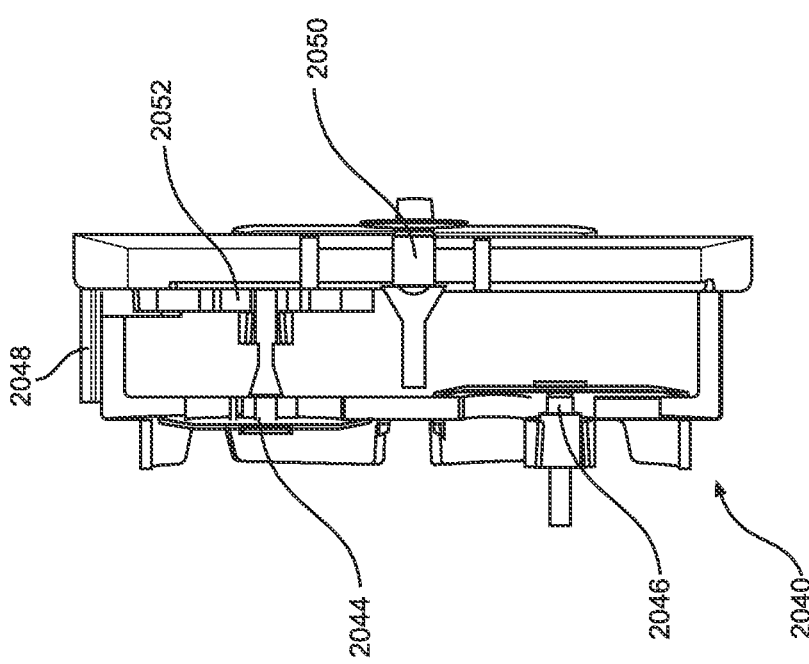
FIG. 37 illustrates a cutout side view of the air intake mechanism.

FIG. 37 illustrates a cutout side view of the air intake mechanism 2040. An inlet pressure valve 2050 allows external air to enter the inflatable bag from the interior of the air intake mechanism 2040. The inlet pressure valve 2050 is an umbrella valve. The air may be external ambient air or a combination of ambient air and oxygen. Ambient air enters the air intake mechanism 2040 through an air inlet valve 2046, and oxygen enters the air intake mechanism 2040 through an oxygen inlet port (not shown). The air inlet valve 2046 is also an umbrella valve.

The air intake mechanism 2040 includes the oxygen inlet port (not shown) to control the proportion of oxygen entering the inflatable bag. In use, oxygen flows into the air intake mechanism 2040 at a rate specified on the oxygen tank, which is usually between 10-15 L/min. The pressure from the oxygen inlet port 2042, combined with the atmospheric pressure, creates a pressure differential between the air intake mechanism 2040 and the expandable bag 2004. Oxygenated air will fill the expandable bag 2004 if the pressure is above that of the inlet pressure valve 2050 and less than the oxygen exhaust valve 2044.

In an embodiment, the flow rate from the oxygen tank is high (for example 10-15 L/min) and the cracking pressure for the oxygen exhaust valve 2044 is kept low to limit the pressure differential created by oxygen flowing into the air intake mechanism 2040.

The air intake mechanism 2040 allows the expandable bag 2004 to fill with oxygen at a consistent flow rate no matter the flow rate from the oxygen tank. The air intake mechanism 2040 also provides for a consistent inflation rate for the expandable bag 2004, no matter the source of the air (straight ambient air, pure oxygen, or a mixture of ambient air and oxygen).

In a further embodiment, the air intake mechanism 2040 includes the override slide 2048. The override slide 2048 may be a sliding wheel, a cinch threading mechanism, two sliding plates, or a push button mechanism. The override slide 2048 may be used to allow for hyperventilation by controlling the size of the plurality of adjustable apertures (not shown) that allow air to enter the expandable bag 2004. In an embodiment, the override slide 2048 aligns an aperture on side panel 2002*a* with a corresponding aperture on the override slide 2048. This slide may be a barrel valve or other mechanism which allows for one or more aperture sizes and thus one or more inflation rates of the expandable bag 2004 between a fully restricted (slow) rate and a fully open (fast) rate.

Figure 38:
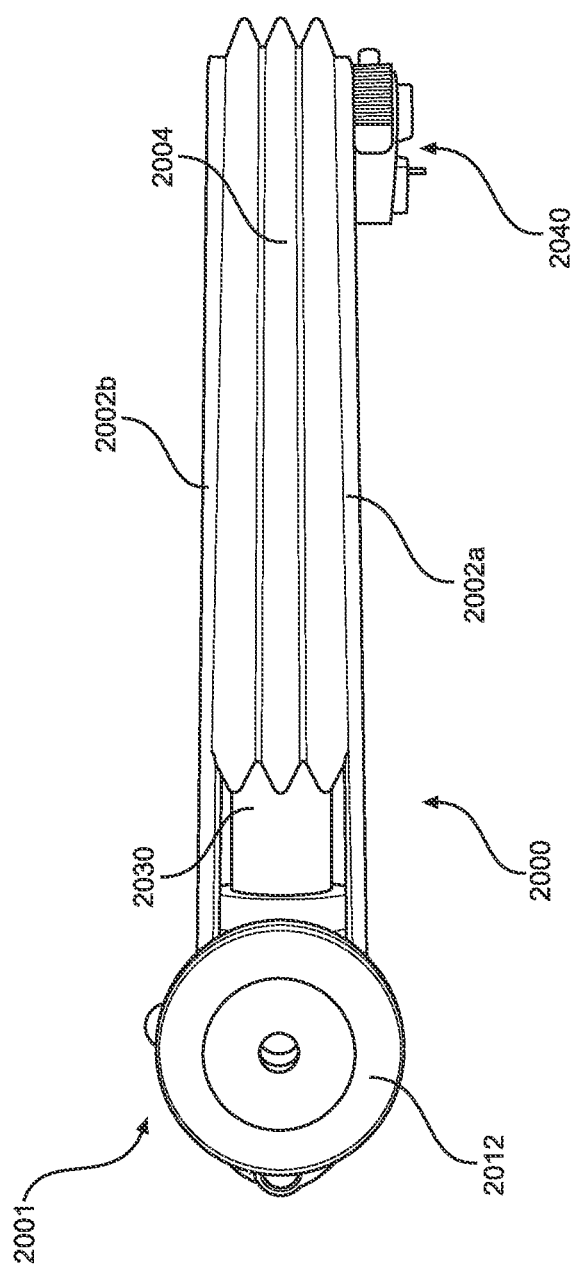
FIG. 38 illustrates a top view of the expandable bag device in a compressed configuration.

FIG. 38 illustrates a top view of the expandable bag device 2000 in a compressed configuration. The first side panel 2002*a* and the second side panel 2002*b* are generally parallel to each other, with the expandable bag 2004 located there between.

Figure 39:
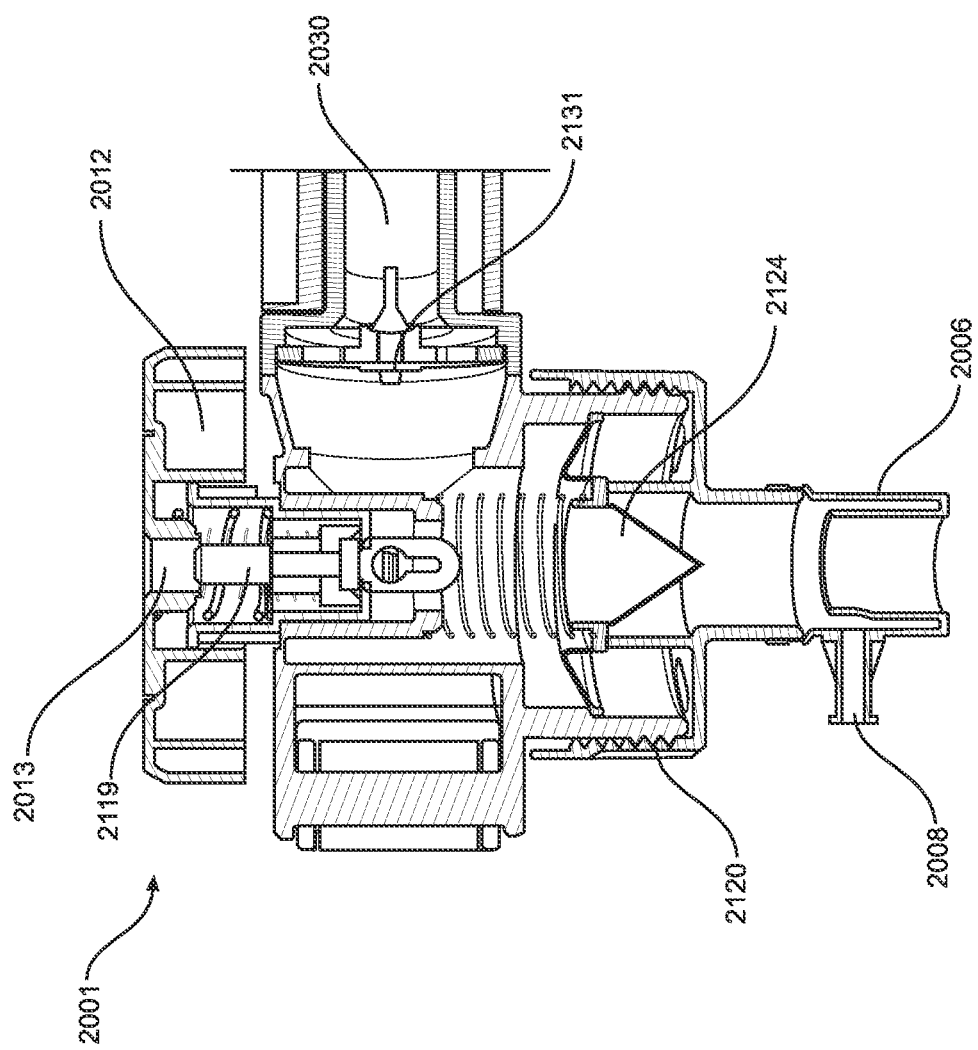
FIG. 39 illustrates a partial cutaway view of the valve housing member.

FIG. 39 illustrates a partial cutaway view of the valve housing member 2001 highlighting the bag connection member 2030. Air flow from the expandable bag 2004 through a valve 2131 in the bag connection member 2030 and into the valve housing member 2001. The valve 2131 prevents air from flowing from the valve housing member 2001 back into the expandable bag 2004.

Figure 40:
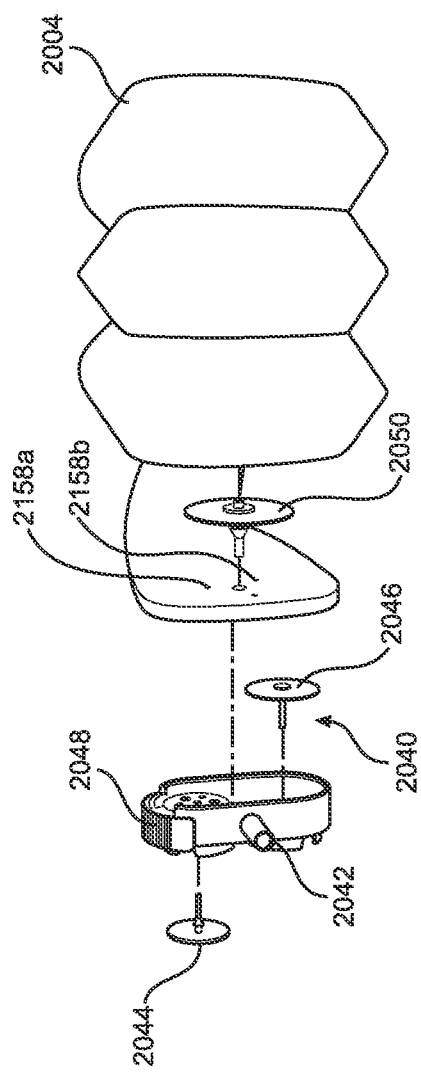
FIG. 40 illustrates an exploded view of the air intake mechanism.

FIG. 40 illustrates an exploded view of the air intake mechanism 2040 and the expandable bag 2004. Ambient air enters the air intake mechanism 2040 through an air inlet valve 2046, and oxygen enters the air intake mechanism 2040 through an oxygen inlet port 2042. The ambient air and the oxygen mix within the air intake mechanism 2040 and enter the expandable bag 2004 via one or more apertures 2158*a*, 2158*b*, the size and number of which are opened to the expandable bag 2004 are controlled by the override slide 2048.

The air intake mechanism 2040 includes the oxygen inlet port 2042 which provides the flow of oxygen with the atmospheric air through the air intake mechanism 2040. The oxygen inlet port 2042 only allows oxygen to flow into the air intake mechanism 2040.

The oxygen exhaust valve 2044 vents excess oxygen into the atmosphere, so it does not enter the expandable bag 2004 and allows for consistent filling times of the expandable bag 2004 regardless of oxygen flow rates from the oxygen source into the air intake mechanism. The override slide 2048 controls an aperture covering mechanism 2052 that determines either the size or the number of apertures 2158 that air is allowed to enter the expandable bag 2004 from the air intake mechanism 2040.

Figure 41:
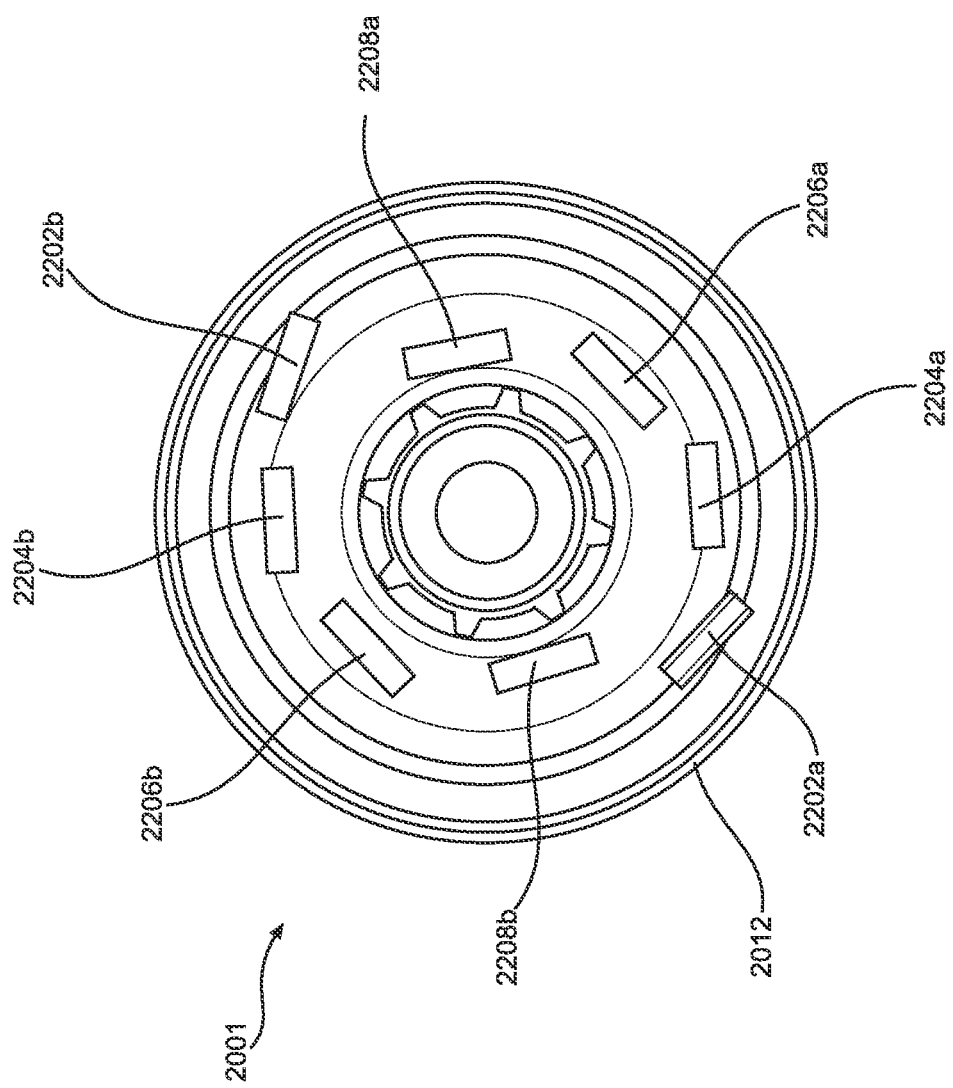
FIG. 41 illustrates a bottom view of the valve connection member.
Figure 42:
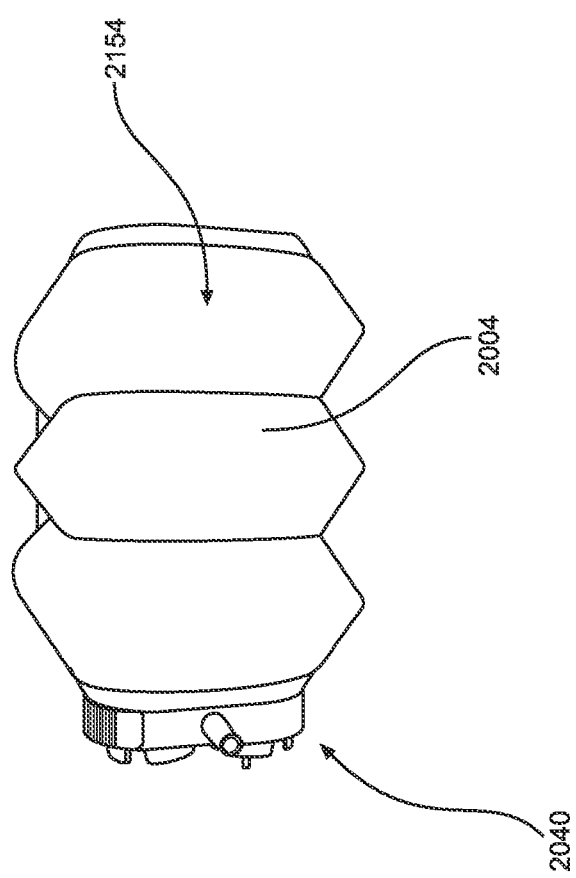
FIG. 42 illustrates a view of the expandable bag in an expanded configuration.

FIG. 41 illustrates a cutaway bottom view of the valve connection member 2001 highlighting the control dial 2012. The control dial 2012 extends around an exterior of the valve housing member 2001. The control dial 2012 comprises the tidal volume controller that has an octagonal shape (four pairs of settings 2202a, 2202b, 2204a, 2204b, 2206a, 2206b, 2208a, 2208b) that restrict the width that the first side panel 2002a and the second side panel 2002b are allowed to expand FIG. 42 illustrates a view of the expandable bag in an expanded configuration. As shown, an end 2154 of the expandable bag 2004 opposite the valve housing member 2001 expands more than an end 2156 adjacent the valve housing member 2001. In the embodiment shown, the air intake mechanism 2040 is located near the end 2154 of the side panel; however, the air intake mechanism 2040 may be located in other places in fluid communication with the expandable bag 2004.

Figure 43:
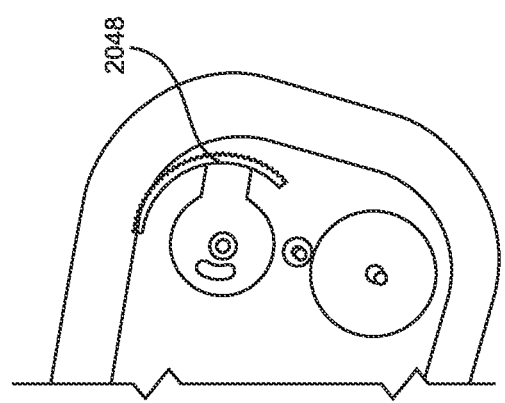
FIG. 43 illustrates an embodiment of the air intake mechanism with the slide in a first position.
Figure 44:
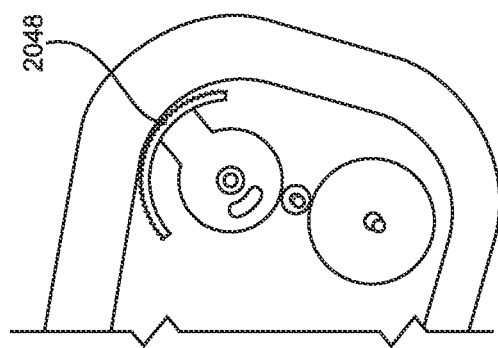
FIG. 44 illustrates an embodiment of the air intake mechanism with the slide in a second position.
Figure 45:
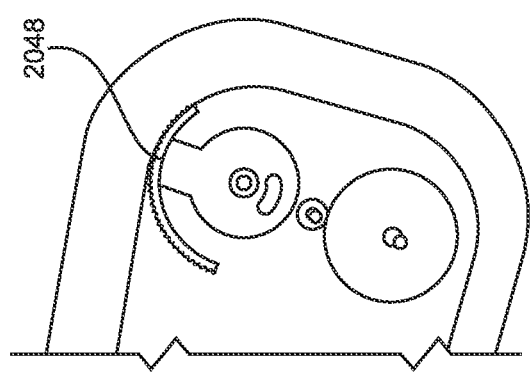
FIG. 45 illustrates an embodiment of the air intake mechanism with the slide in a third position.

FIGS. 43-45 illustrates an embodiment of the air intake mechanism 2040 with the slide in various positions. FIG. 43 illustrates an embodiment of the air intake mechanism with the slide in a first position. FIG. 44 illustrates an embodiment of the air intake mechanism with the slide in a second position. FIG. 45 illustrates an embodiment of the air intake mechanism with the slide in a third position.

Each position of the override slide 2048 corresponds to a different flow rate from the air intake mechanism 2040 to the expandable bag 2004. The first position of the override slide 2048 allows for air to flow into the expandable bag 2004 at a first rate, the second position of the override slide 2048 allows for air to flow into the expandable bag 2004 at a second rate, and the third position of the override slide 2048 allows for air to flow into the expandable bag 2004 at a third rate.

FIGS. 46A-49B illustrate another alternative embodiment of an expandable bag device 3000 whose configuration and operation generally corresponds to the configuration of expandable bag device 2000 with exceptions noted below. However, it should be noted that different features in each of the expandable bag device embodiments 1000, 2000, 3000 can be utilized in any of other expandable bag device embodiments without departing from the spirit or scope of the invention.

Figure 46A:
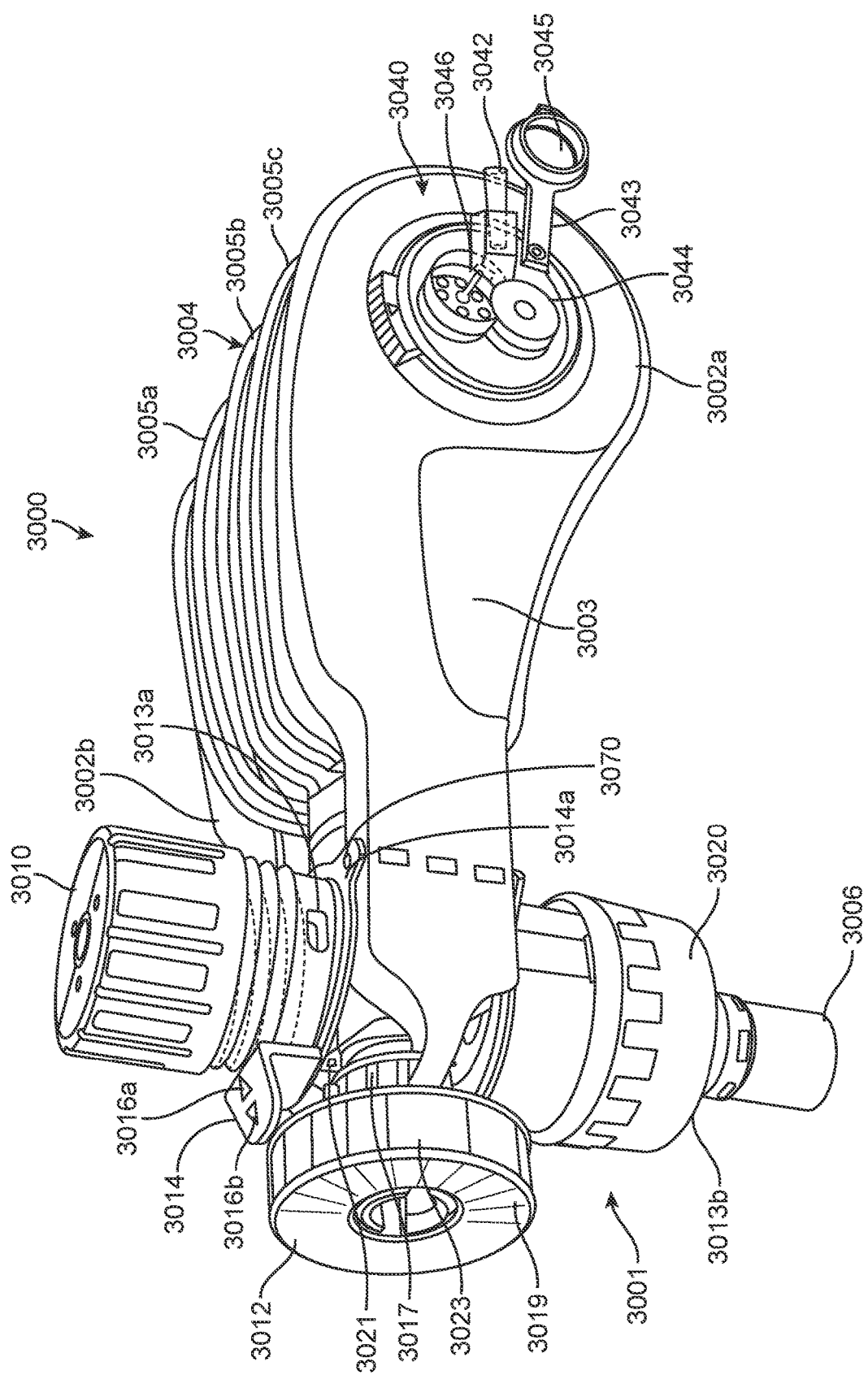
FIGS. 46A-46C illustrate a perspective view of an alternative embodiment of an expandable bag device, a close-up perspective view of a tidal volume control device usable with the expandable bag device of FIG. 46A, and an alternative embodiment of a tidal volume control device usable with the expandable bag device of FIG. 46A, respectively.
Figure 46B:
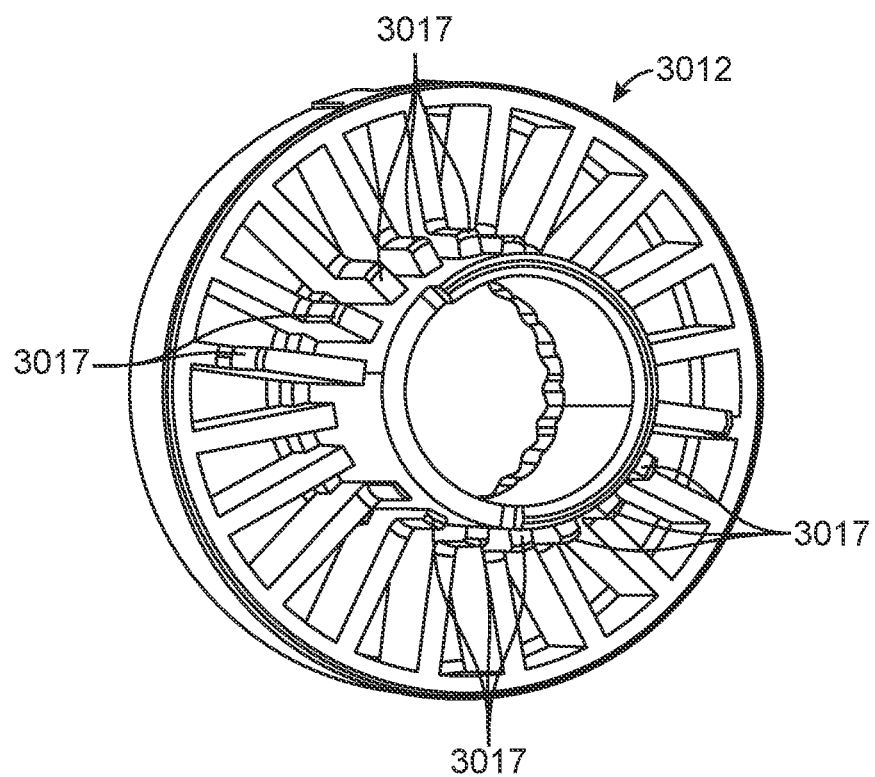

FIG. 46A shows the expandable bag device 3000 including an expandable bag 3004 located between a first side panel 3002a and a second side panel 3002b. The expandable bag device 3000 also includes a valve housing member 3001 extending from a first end of the first and second side panels 3002a, 3002b. The valve housing member 3001 may be attached to any type and size of mask or other patient breathing interface device, such as an endotracheal tube or laryngeal mask airway.

The first side panel 3002a and the expandable bag 3004 also include an air intake mechanism 3040. Air intake mechanism 3040 generally corresponds to and operates similarly to air intake mechanism 2040 of the expandable airbag device 2000 in that the air intake mechanism 3040 includes an exhaust valve 3044, an air inlet valve 3046, and a compressed gas inlet port 3042. However, the air intake mechanism 3040 of FIG. 46A additionally includes a mechanical inflation adjustment control device 3041 to adjust the flow rate of a compressed gas or gases (e.g., oxygen, helium, etc.) or of ambient air into the expandable bag 3004 through one or more apertures, e.g., apertures 2158a, 2158b (see FIG. 40) being supplied. The inflation adjustment control device 3041 adjusts the size of one or more apertures 3043 to one or more smaller size apertures 3043, which decrease the flow rate of the compressed gas/ambient air into the expandable bag 3004 resulting in a slower inflation time of the expandable airbag device 3000, and to one or more larger size apertures 3043, which increase the flow rate of the compressed gas/ambient air into the expandable bag 3004 resulting in a faster inflation time of the expandable airbag device 3000.

In certain embodiments, the air intake mechanism 3040 additionally includes a blocking cap 3045 that can be used to plug, or close off, the exhaust valve 3044. A blocking of the exhaust valve 3044 can assist the expandable bag device 3000 to provide Continuous Positive Airway Pressure (CPAP) when: (a) the expandable bag device 3000 is connected to compressed gas supply via compressed gas inlet port 3042; and (b) the PEEP valve 3020 is engaged. CPAP is a desirable feature when a patient utilizing the expandable bag device 3000 is already breathing. In certain embodiments, a blocking of the exhaust valve 3044 is not needed for the expandable bag device to provide CPAP, rather only items (a) and (b) are needed.

In certain embodiments, the air intake mechanism 3040 excludes one or both of the exhaust valve 3044 and the compressed gas inlet port 3042 for simplified construction.

The first and second side panels 3002a, 3002b of the expandable bag 3004 are of a stiffer material than that of the expandable bag 3004 allowing a user to hold the side panels 3002a, 3002b to compress the expandable bag 3004. The first and second side panels 3002a, 3002b, additionally include ergonomic recesses 3003, that are preferably textured, to accommodate a user's hand for singled-handed use of the expandable bag device 3000. The single-handed use includes performing compressions/decompressions of the expandable bag device 3000 while maintaining, with the expandable bag device 3000, a seal about a patient's mouth; dual-handed use of the expandable bag device 3000 is also possible.

Figure 52:
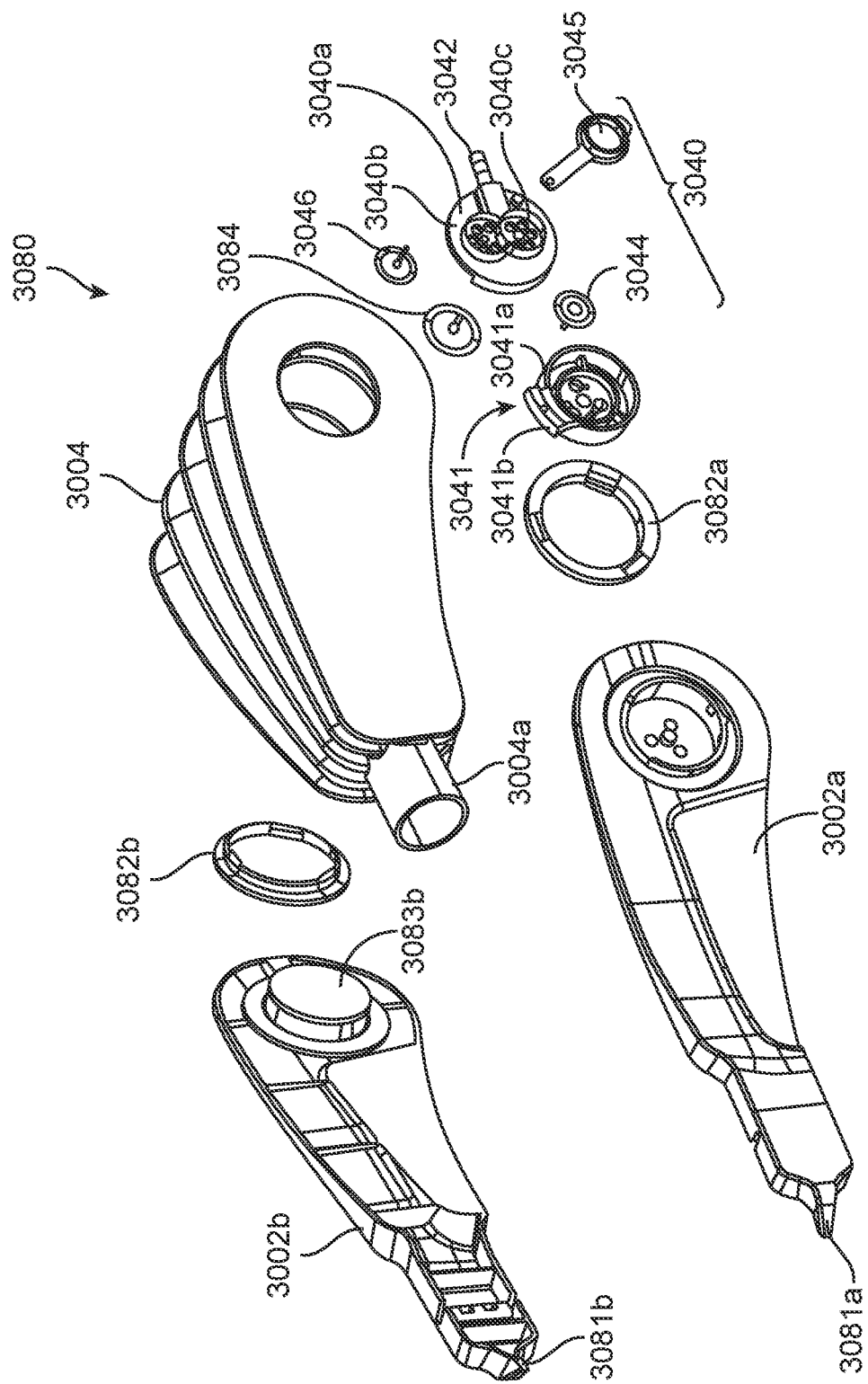
FIG. 52 is an exploded view of a rear portion of the expandable bag device of FIG. 46A.
Figure 57A:
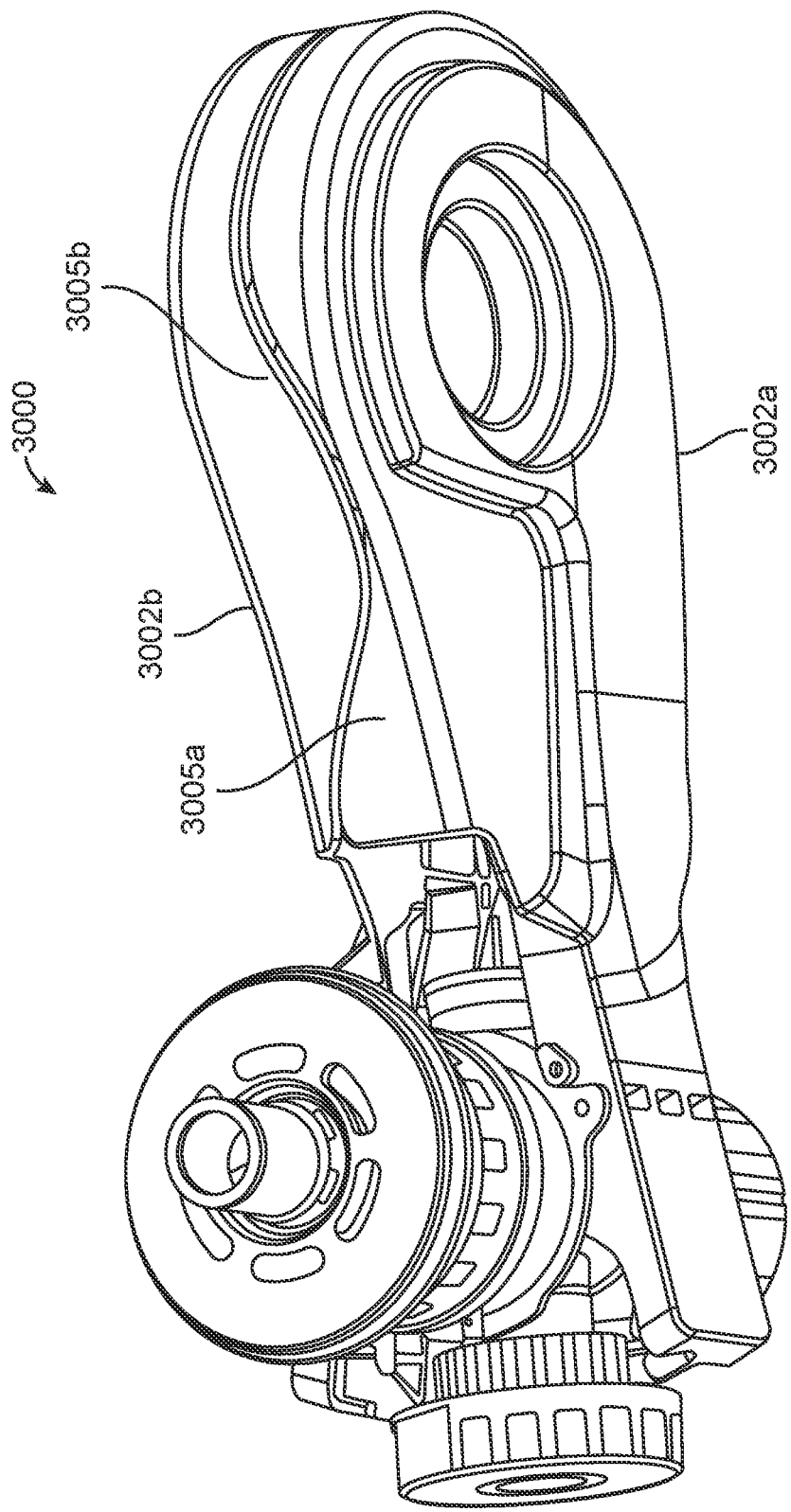

Within the expandable bag 3004 proximate each side panel 3002a, 3002b is provided an internal stop (see 3083a, 3083b of FIG. 52). During a full compression of the expandable bag device 3000, the internal stops will meet providing an auditory response (e.g., clicking sound, whistle, etc.) and/or a mechanical stopping point to indicate to the user that a full compression of the expandable bag device 3000 has occurred and to prevent delivery of imprecise volumes of air. In certain embodiments, referring to FIGS. 57A-57B, the side panels 3002a, 3002b include interfacing contoured edges 3005a, 3005b that operate as external stops to indicate a full compression of the expandable bag device 3000. The contoured edges 3005a, 3005b alternatively, or additionally, operate as an expandable bag distortion prevention feature that prevents outward ballooning of one or more folds 3007 of the expandable bag 3004 thereby helping to favor evacuation of air from the expandable bag 3004 and into the valve housing member 3001. The side panels 3002a, 3002b with contoured edges 3005a, 3005b also serve to completely enclose the expandable bag 3004 when the side panels 3002a, 3002b are fully compressed to provide the expandable bag 3004 with a protective hard shell. Referring to FIG.

57C, alternatively, or in addition to the contoured edges 3005a, 3005b, each of the side panels 3002a, 3002b includes one or more tabs, 3009a, 3009b that extend over one or more folds 3007 of the expandable bag 3004; the tabs 3009a, 3009b may serve as external stops and/or as a distortion prevention feature for the folds 3007 of the expandable bag 3004. In certain embodiments the contoured edges 3005a, 3005b and/or the tabs 3009a, 3009b are presented at both an upper surface and a lower surface of the side panels.

In certain embodiments, the expandable bag device 3000 is equipped with an adjustable timing mechanism (e.g., a timing light, an auditory notification, etc.) to inform a user when a next compression/decompression should occur. For example, a timing light is programmed to light every predetermined number of seconds with each occurrence of light indicating another compression/decompression should occur. In certain embodiments, the adjustable timing mechanism is pre-programmed to accommodate different types of patients (e.g., child, baby, or adult).

The valve housing member 3001 has been redesigned from the valve housing member 2001 of the expandable bag 2000. The valve housing member 3001 includes a body portion that presents a patient breathing interface connection member 3006, a mechanical PIP control device 3010, a mechanical tidal volume control device 3012, a control device indicator 3014 including first and second indicators 3016a, 3016b to indicate the position of the PIP control device 3010 and the tidal volume control device 3012, a mechanical PEEP control device 3020 and one or more pressure relief openings 3013a, 3013b. In certain embodiments, the tidal volume control device 3012 is positioned perpendicularly to the PIP control device 3010 as shown, however, other positionings of the tidal volume control device 3012 relative to the PIP control device are also possible. It should be noted that while the mechanical control devices 3010, 3012 and 3020 are illustrated as dials any other suitable adjustable control device (e.g., multi-position switches, buttons, or levers, etc.).

The PIP control device 3010 adjusts a length of a spring on an internal PIP valve (see FIGS. 34-35 for additional detail) by turning about threads on a body of the valve housing member 3001. Adjustment of this spring makes it possible to apply a variable amount of downward pressure on the upper aspect of the PIP valve (not shown). When the PIP valve is fully restricted, it will not allow venting of excess pressure (simulating the infinite peak pressure that is sometimes needed during use). Thus, an adjustment of PIP can modify the pressure at which excess pressure is vented from inside the valve housing member 3001 through one or more of the pressure openings 3013a, 30113b to the periphery. In certain embodiments, the PIP control device 3010 includes indicia representative of a plurality of PIP settings, which correspond to established PIP standards, to accommodate patients of different sizes. For example, in one configuration, the PIP control device 3010 and underlying valve may be calibrated and labeled with a plurality of PIP settings to accommodate one or more of a baby, a child, or an adult while in another configuration the PIP control device 3010 and underlying valve may be calibrated and labeled with a plurality of PIP settings to accommodate all patients. The PIP control device 3010 increases/decreases pressure on an internal component that is lifted in order to vent excess pressure to the periphery. Increasing the pressure on the internal component (done by compressing a spring on the internal component) raises the pressure needed to vent. Decreasing the pressure on the internal component (done by lengthening the spring) lowers the pressure on the internal component and allows it to vent more readily.

Figure 49A:
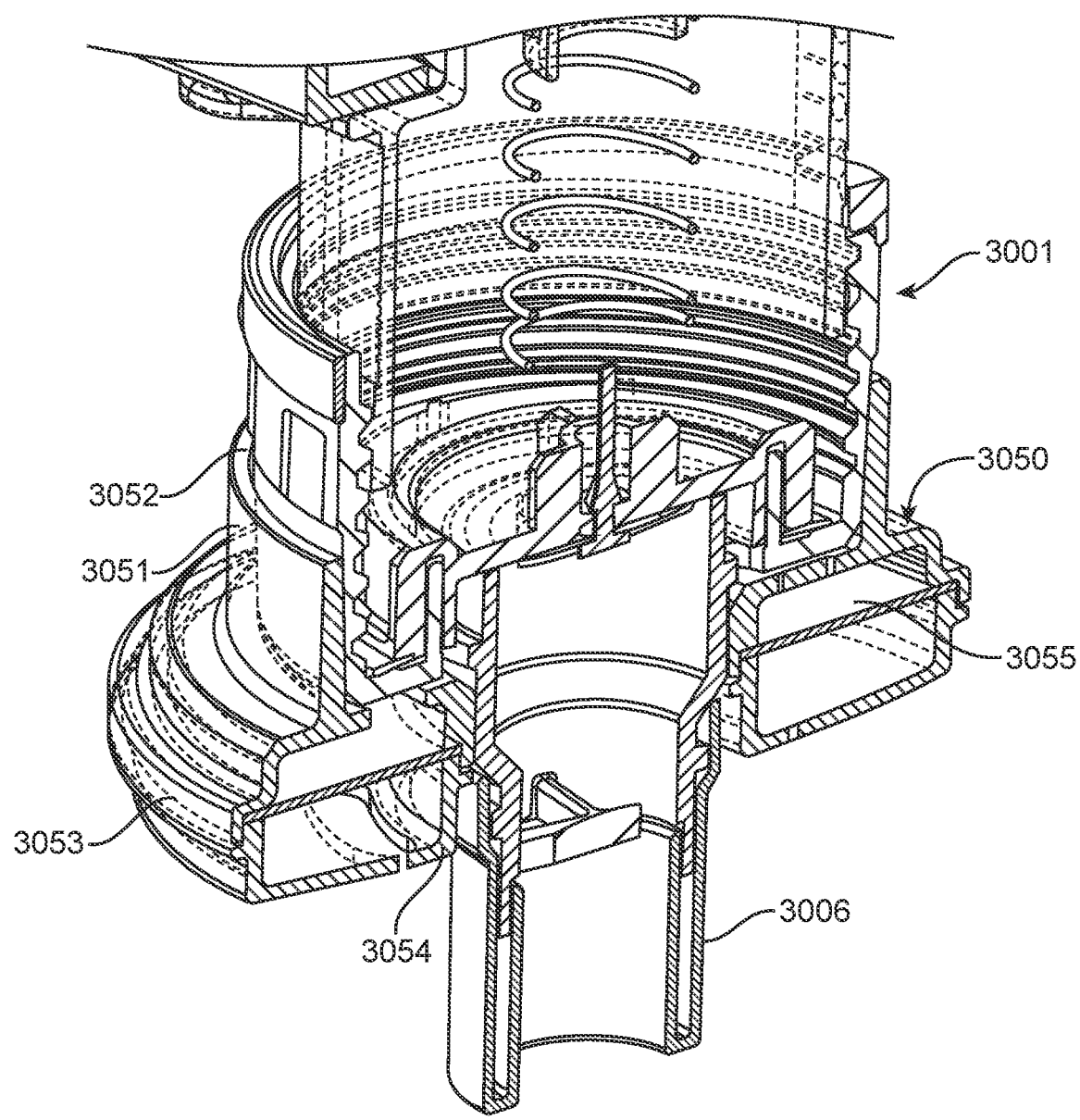
FIG. 49A illustrates a cross-sectional view of the filter body coupled to the expandable bag device of FIG. 46A
Figure 49B:
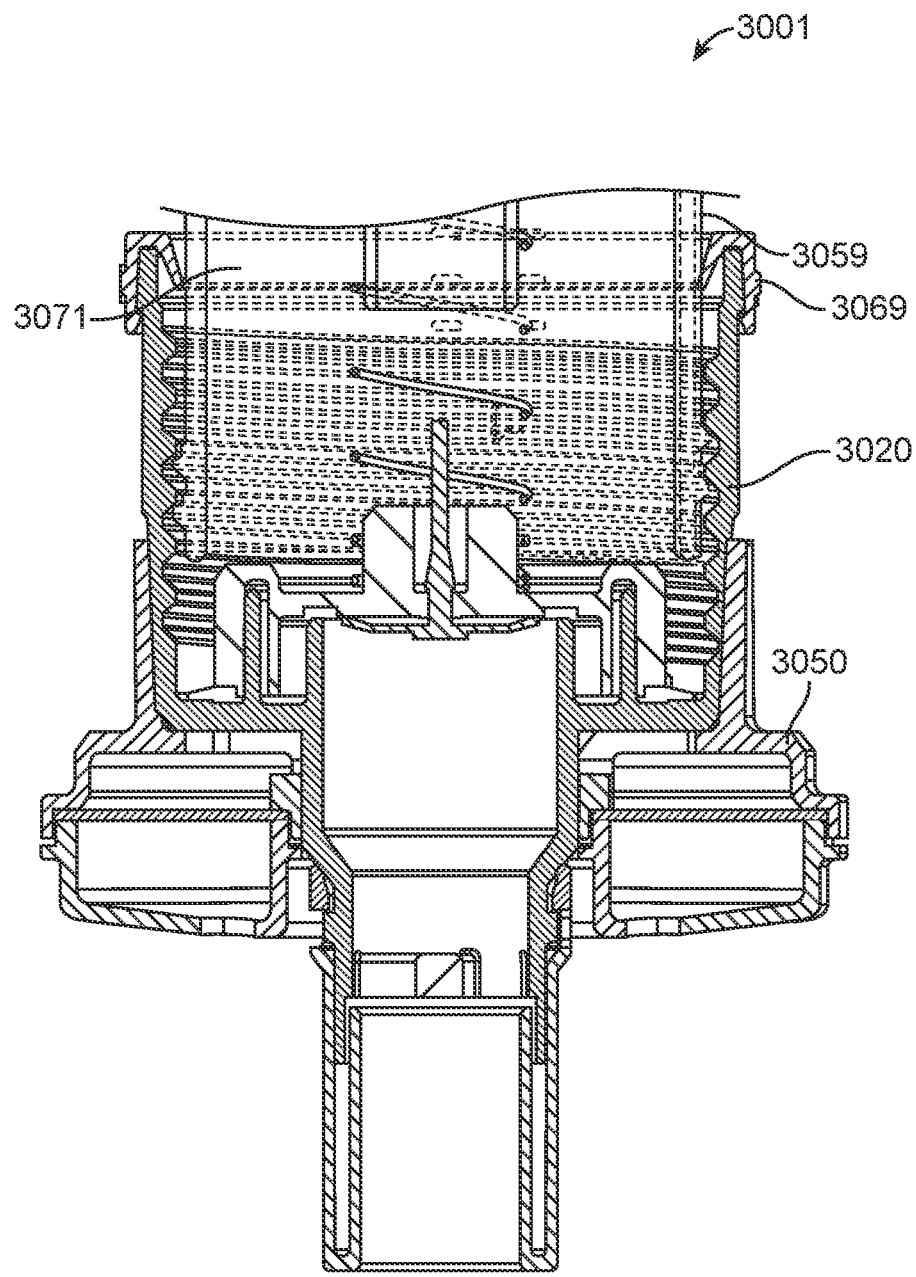
FIG. 49B illustrates the same cross-sectional view including a sealing feature.

The PEEP control device 3020 is turned to change the pressure required for the patient to exhale and is described in further detail elsewhere herein including details provided in reference to FIGS. 19, 20, 30 and 35. In certain embodiments, an o-ring or other type of sealant is provided intermediate the PEEP control device 3020 the main body 3059 of the valve housing member 3001 to prevent patient exhalations from escaping out a top edge of the PEEP control device 3020. By way of example, FIG. 49B illustrates that the PEEP control device 3020 is capped with a PEEP indicator ring 3069 that includes a sealing edge 3071 intermediate the PEEP control device 3020 the main body 3059 of the valve housing member 3001 to prevent the escape of patient exhalations.

Figure 46C:
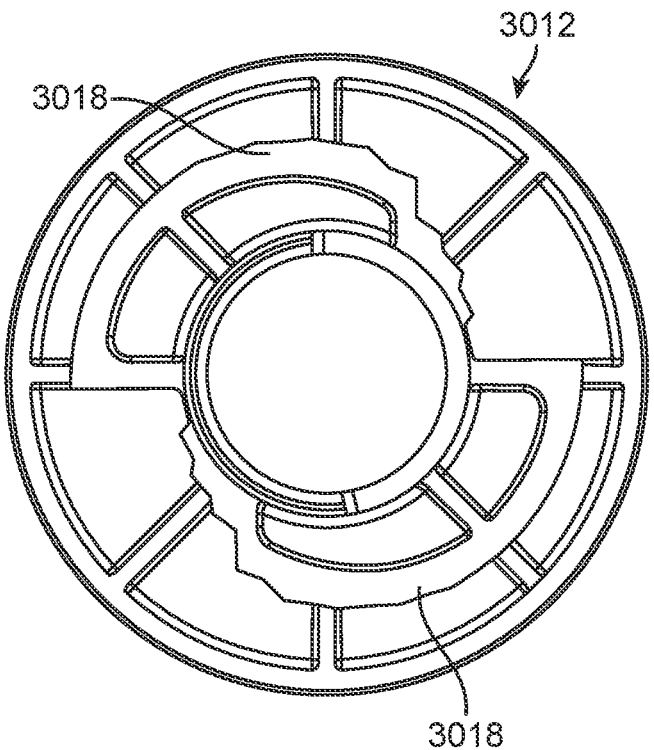
Figure 48:
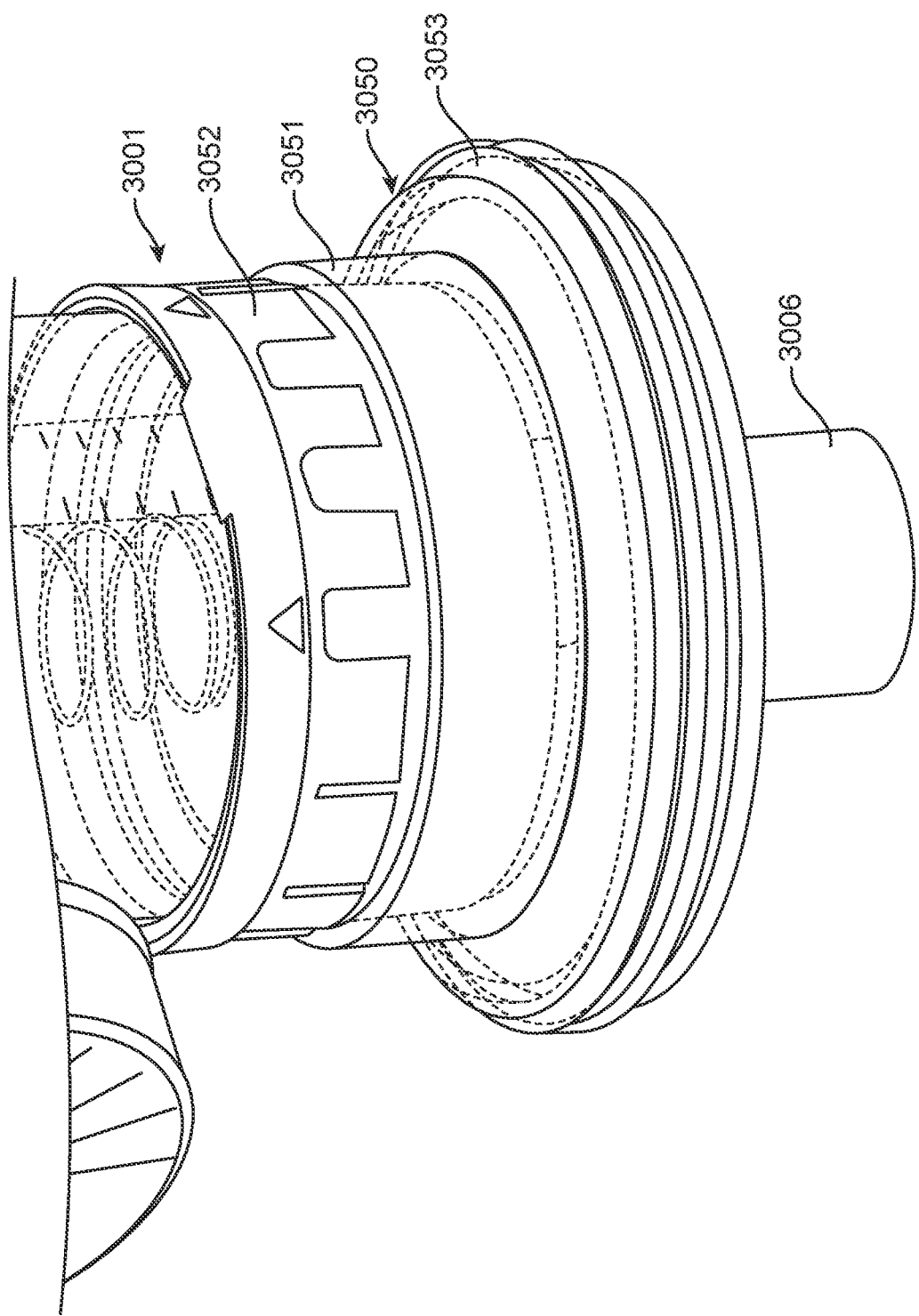
FIG. 48 illustrates a side perspective view of the filter body coupled to the expandable bag device of FIG. 46A.

The tidal volume control device 3012 operates to adjust biasing member projections 3081a, 3081b (see FIG. 51) that extend from the first and second side panels 3002a, 3002b to control how widely the expandable bag 3004 expands; the biasing member projections 3081a, 3081b project forward from the hinge pins 3070 that secure the first and second side panels 3002a, 3002b to the valve housing member 3001. The tidal volume control device 3012 is equipped with two sets of oppositely positioned cogs 3017 (see FIG. 46B). Within each set of cogs 3017, each cog 3017 varies in depth from the next proximate cog 3017. Corresponding opposing cogs 3017 are capable of interfacing corresponding biasing member projections 3081a and 3081b, respectively, to provide a desired volume. In certain embodiments, rather than presenting two sets of individually formed cogs with each proximate cog increasing in depth, two opposing ramped surfaces 3018 as illustrated in FIG. 46C, each of which gradually increases in depth, is provided. Each of the plurality of cogs 3017 (or position on the ramped surface 3018) corresponds to a different tidal volume of air that will be delivered to a patient; a tidal volume scale 3019 reflective of the tidal volume provided by each respective cog 3017 (or ramped surface 3018) is provided on the tidal volume control device 3012. For example, the tidal volume scale 3019 may identify increments (each of which corresponds to a respective cog 3017 (or position on the ramped surface)) of tidal volume between those suitable for an infant or child based on current resuscitation guidelines and/or suitable for an adult. In certain embodiments, tidal volume is configured on a single expandable device 3000 for infants, children, and adults. In certain embodiments, the tidal volume control device 3012 is additionally marked with color-coded indicia 3023 that correspond to established standards used to determine the volumes of air needed for a patient based on their length/height, weight, and/or age.

In certain embodiments, see FIGS. 47-49B, the expandable bag device 3000 includes a filter body 3050 that is fixedly or removably secured to the valve housing member 3001. In illustrated embodiment, the filter body 3050 is secured to the valve housing member 3001 via the PEEP control device 3020. The filter body 3050 includes a neck portion 3051 secured to a lower portion of the PEEP control device 3020 as well as an annular filter-holding portion 3053. A central opening 3054 extends through the filter body 3050 to accommodate its position about the patient breathing interface connection member 3006. An annular bio/viral filter 3055 lies within the annular filter-holding portion 3053 of the filter body 3050 to filter patient exhalations. In certain embodiments, the bio/viral filter 3055 generates its own PEEP (or resistance against exhalation). In certain embodiments, the filter body 3050 is detachable from the expandable bag device 3000. The bio/viral filter 3055 lies within the filter body 3050 and serves to filter viruses and bacteria from patent exhalations.

Figure 50B:
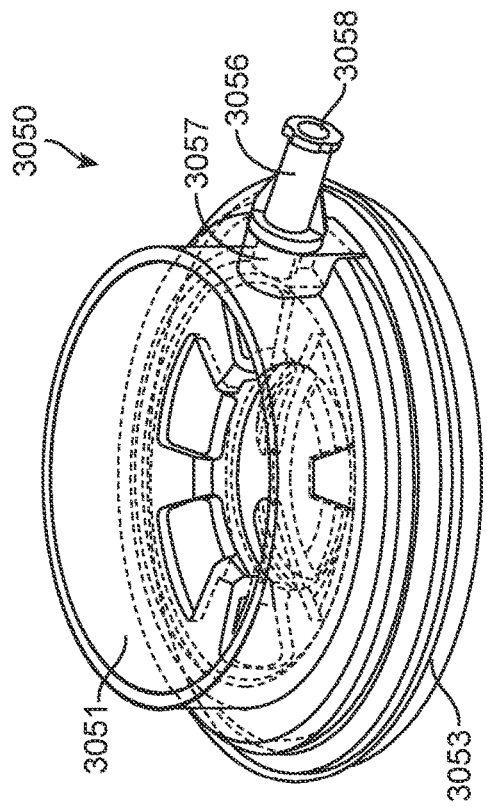
FIGS. 50A-50C illustrate an exploded view, an assembled view and a cross-sectional view, respectively, of an alternative embodiment of a filter body.
Figure 50A:
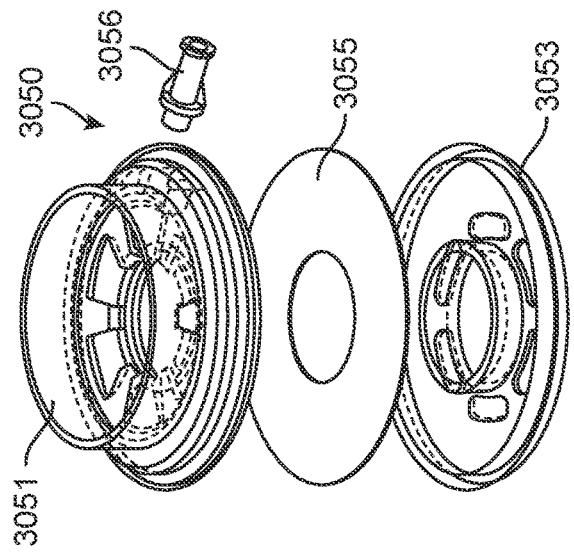
Figure 50C:
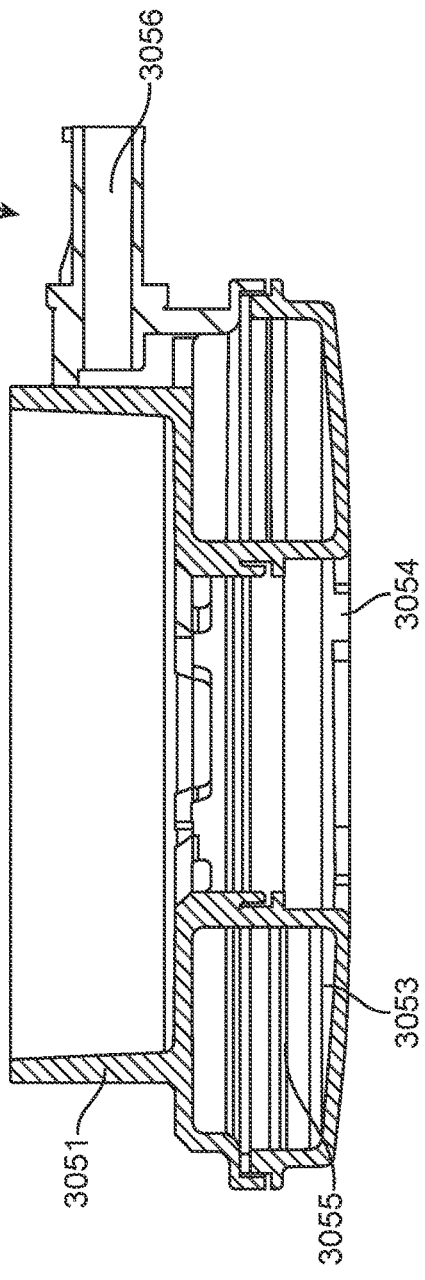

Referring to FIGS. 50A-50C, the filter body 3050 is equipped with an exhalation port in the form of a luer lock 3056 that can be fixedly secured or removably secured to the neck portion 3051 of the filter body. The luer lock 3056 includes a channel extending from a first end 3057 to a second end 3058. The first end 3057 provides access to patient exhalations at a position above the filter 3055 such as at the interior of the neck portion 3051 while the second end 3058 extends outward from the neck portion 3051. The second end 3058 is couplable by tubing to an end-tidal $CO_2$ monitor or other appropriate monitoring device. End-tidal $CO_2$ monitoring provides a user operating the expandable bag device 3000 with insight into the fraction of $CO_2$ present in a patient's exhalations. A lower fraction of $CO_2$ can provide an indication that a user operating the expandable bag device 3000 should decrease device compressions/expansions while a high fraction of $CO_2$ can provide an indication that the user should increase device compressions/expansions. In certain embodiments, when end-tidal $CO_2$ is not needed or is not available, the second end 3058 of the luer lock 3056 is capped with a removable cap.

In certain configurations, the expandable bag device 3000 is specifically configured for pediatric (child and/or infant) applications and includes appropriately configured components, e.g., dials, valves, and biasing members. In certain configurations, the expandable bag device 3000 is specifically configured for adult applications and includes appropriately configured components, e.g., dials, valves, and biasing members. In certain configurations, a single expandable bag device is configured for all types of patients.

Additional features of the expandable bag device 3000 can be appreciated with respect to FIGS. 51-55B.

Figure 51:
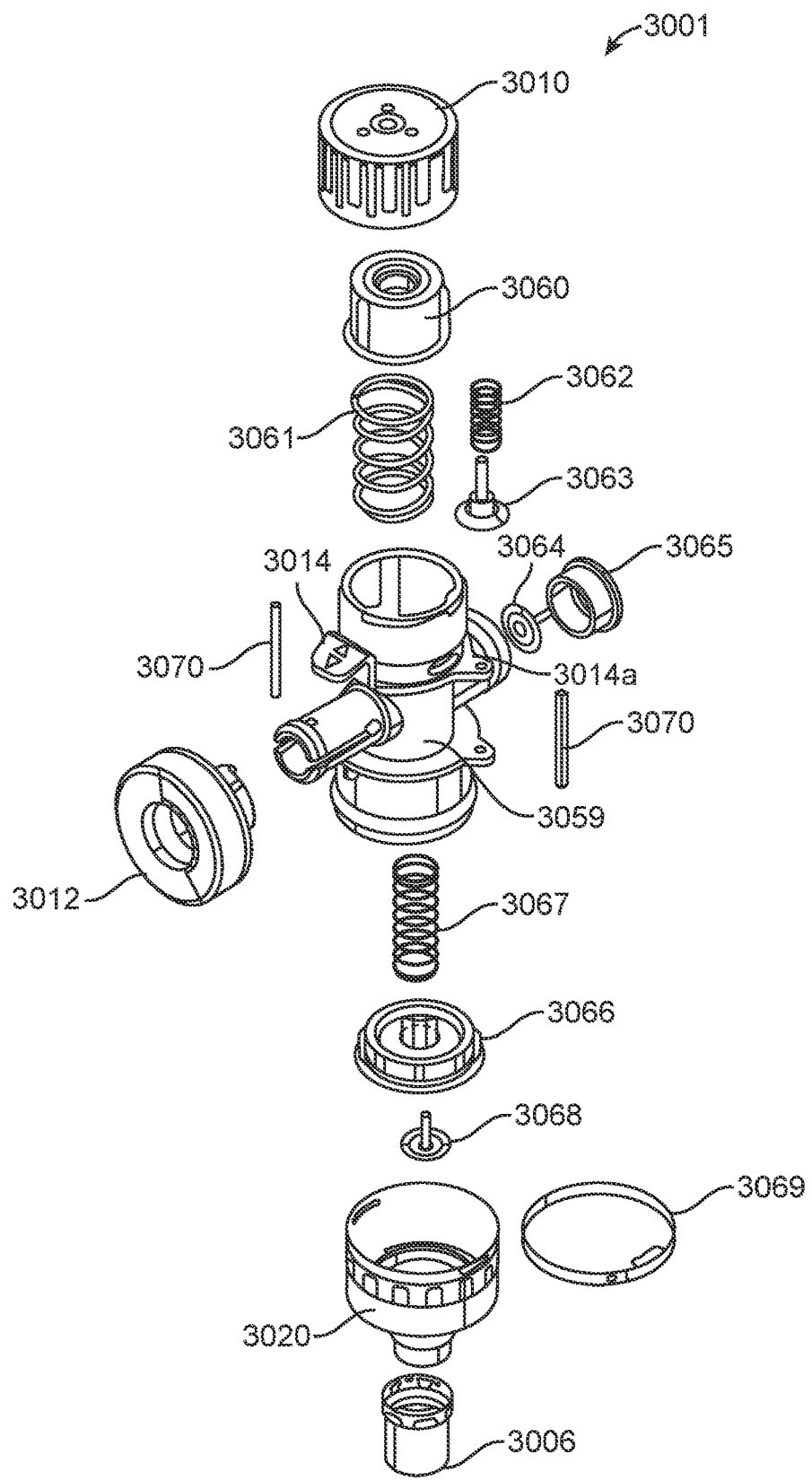
FIG. 51 is an exploded view of a valve housing member of the expandable bag device of FIG. 46A.

FIG. 51 provides an exploded view of the valve housing member 3001. As shown the valve housing member 3001 includes a main body 3059 that interfaces with the tidal volume control device 3012, the PIP control device 3010, and the PEEP control device 3020. The PIP control device 3010, when secured to the main body 3059, engages an inner control device 3060 to compress/decompress one or both of an outer spring 3061 and an inner spring 3062 to apply a variable amount of downward pressure on the PIP valve 3063; the control device indicator 3014 indicates the set positioning of the PIP control device 3010 and the tidal volume control device 3012; the control device indicator 3014 is supported by a ring 3014a positioned about the main body 3059. The valve housing member 3001 additionally includes a backflow valve 3064 and covering 3065 that interfaces with the main body 3059 to prevent a back flow of air from the valve housing member 3001 into the expandable bag 3004. Further, the valve housing member 3001 includes the PEEP control device 3020 that interfaces with the main body 3059 and engages an inner PEEP control device 3066 to compress/decompress a spring 3067 to exert pressure on a PEEP valve 3068 to control the pressure required for a patient to exhale. The PEEP indicator ring 3069 is also provided to indicate the setting of the PEEP. First and second side pins 3070a, 3070b act as hinges to connect the valve housing member 3001 to the first and second side panels 3002a, 3002b. In certain embodiments the PEEP indicator ring 3069 is distinct from the PEEP control device 3066 while in other embodiments the PEEP indicator ring 3069 is unitary with the PEEP control device 3066.

Figure 53:
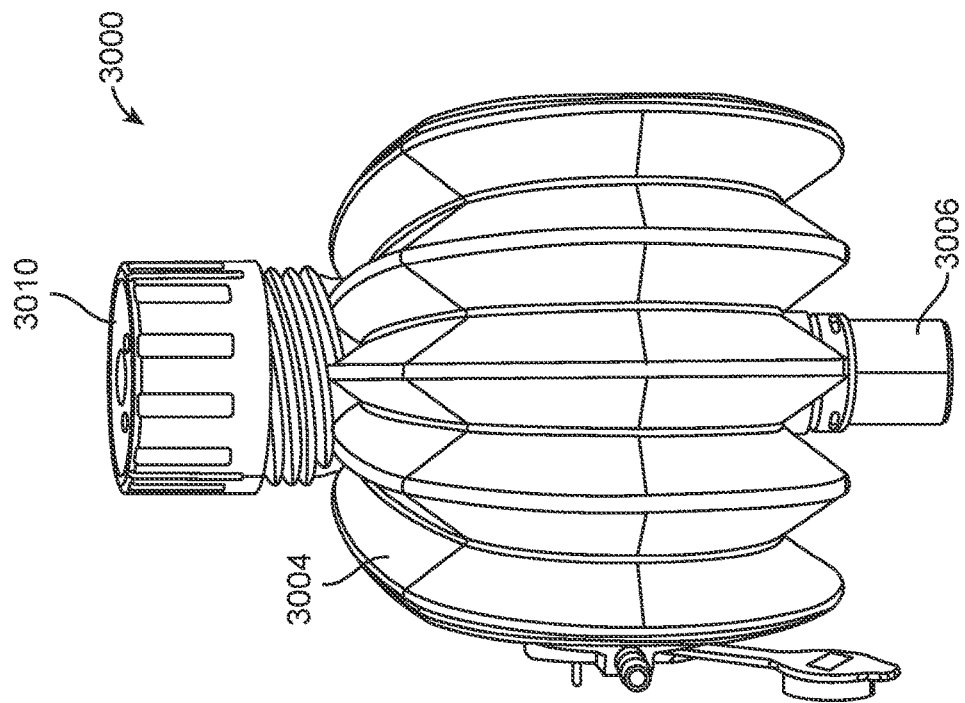
FIG. 53 is a rear perspective view of the expandable bag device of FIG. 46A with the expandable bag removed.
Figure 54:
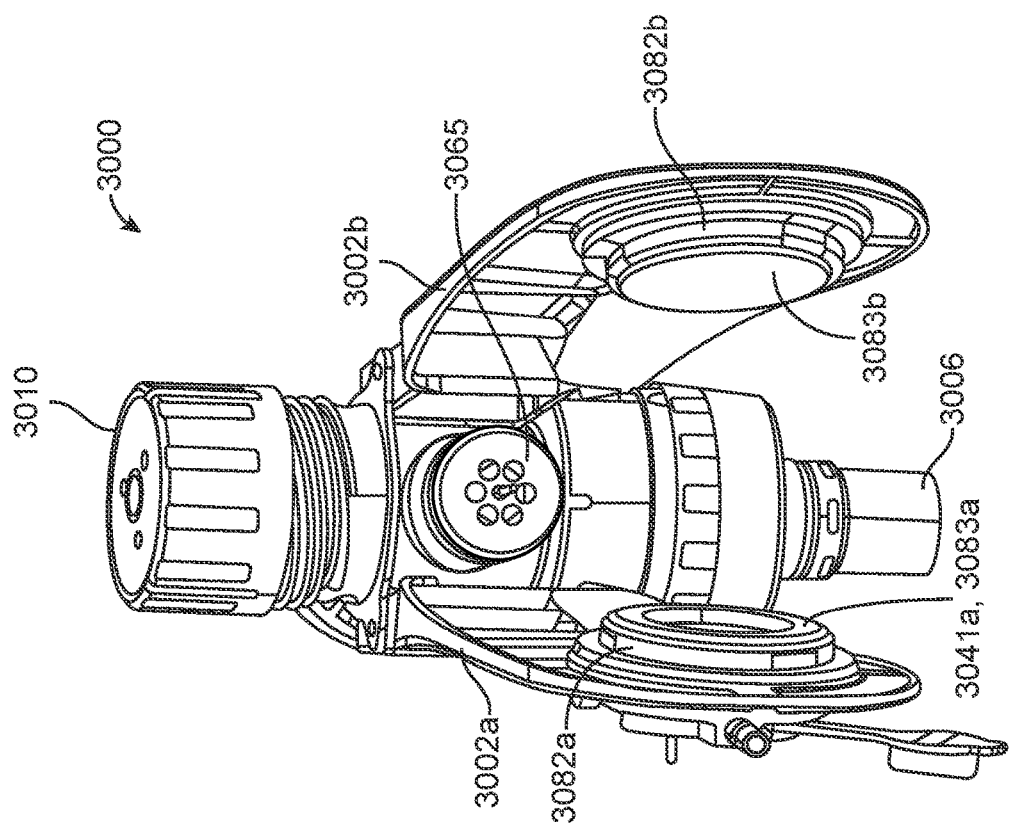
FIG. 54 is a rear perspective view of the expandable bag device of FIG. 46A with the expandable bag present.

FIG. 52 provides an exploded view of a rear portion 3080 of the expandable bag device 3000 beyond the valve housing member 3001. As shown the rear portion 3080 includes the expandable bag 3004, having a funnel portion 3004a, as well as first and second side panels 3002a, 3002b, which include forward narrowed projections 3081a, 3081b. First and second rings 3082a, 3082b serve to clamp the expandable bag 3004 to inner projections 3083a and 3083b of the first and second side panels 3002a, 3002b; the inner projections 3083a, 3083b serve as stops to one another providing an indication to the user when the expandable bag has been fully compressed. The rear portion 3080 of the expandable bag device 3000 additionally includes the air intake mechanism 3040 which includes a cover portion 3040a incorporating the compressed gas inlet port 3042 as well as an opening 3040b to the air inlet valve 3046 and an opening 3040c to the exhaust valve 3044; a pin 3040d is provided for securing the blocking cap 3045. The cover portion 3040a of the air intake mechanism is secured to a body portion 3041a of the inflation adjustment control device 3041. The body portion 3041a contains one or more apertures 3041b to adjust a flow rate of compressed gas or ambient air into the expandable bag 3004 through interior valve 3084 which is positioned over the apertures 3041b. FIGS. 53 and 54 provide additional insight into the configuration of the expandable bag device 3000 by illustrating a rear view of the assembled expandable bag device 3000 with the expandable bag 3004 removed, FIG. 53, and with the expandable bag 3004 present, FIG. 54.

Figure 55B:
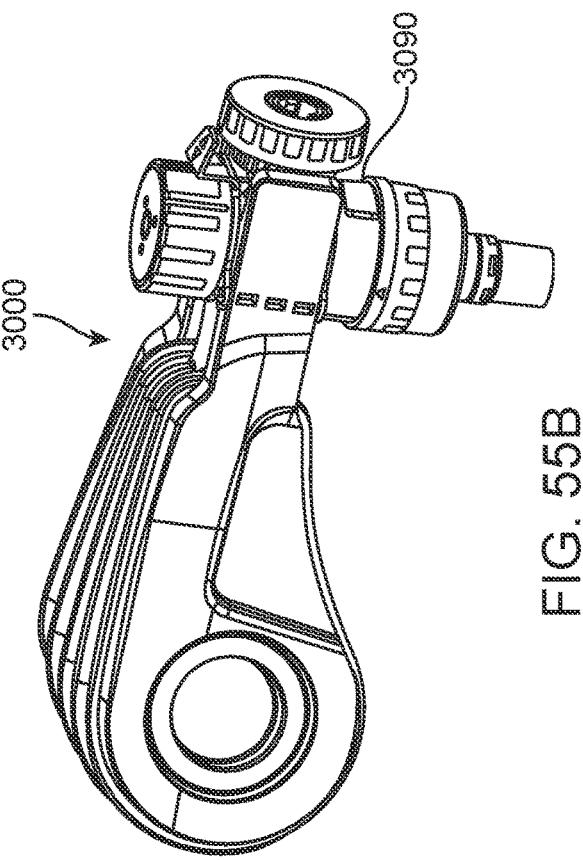
FIGS. 55A-55B illustrate a first side view and a second side view, respectively of the expandable bag device of FIG. 46A including a PEEP lock.
Figure 55A:
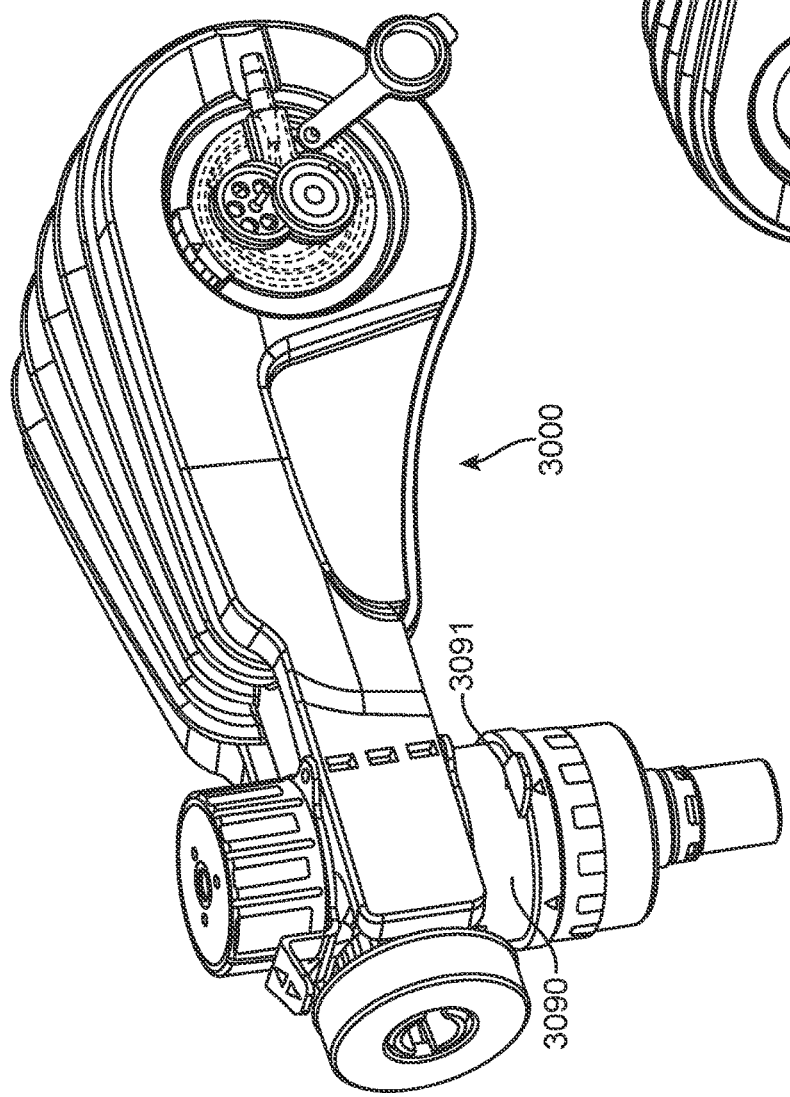

FIGS. 55A-55B illustrate the expandable bag device 3000 with a removable PEEP lock 3090 secured about the main body 3059 of the valve housing member 3001 proximate the PEEP control device 3020. When secured about the main body 3059, the PEEP lock 3090 prevents movement/adjustment of the PEEP control device 3020 and keeps the PEEP value at zero. Removal of the PEEP lock 3090, by pulling on tab 3091, permits adjustment of the PEEP control device 3020 and a corresponding increase in the PEEP value.

As mentioned herein, the expandable bag device 3000 can include internal projections 3083a, 3083b (see FIG. 52) that serve as internal stops that meet during a full compression of the expandable bag device 3000 and provide an auditory response (e.g., clicking sound, whistle, etc.) and/or a mechanical stopping point to indicate to the user that a full compression of the expandable bag device 3000 has occurred and to prevent delivery of imprecise volumes of air. In certain embodiments, with reference to FIGS. 56A-56B, the expandable bag device 3000 additionally or alternatively includes a projecting external stop 3092 on each of the first and second side panels 3002a, 3002b. Each of the projecting external stops 3092 interface with a recess 3093 formed in the ring 3014a of the control device indicator 3014 during compression of the expandable bag device 3000 to prevent further compression or over-compression of the expandable bag device and prevent delivery of imprecise air volumes.

The respiratory devices described herein provide respiratory support to a patient through an expandable bag that is fluidly connected to a valve housing via an inlet having a central axis. The respiratory support is delivered to the patient through an outlet of the valve housing where the outlet has a central axis that is perpendicular to the central axis of the inlet.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

The invention claimed is:

1. A respiratory device for providing respiratory support to a patient, the respiratory device comprising:
   an expandable bag having an air inlet valve and having first and second sides bounded, respectively, by first and second rigid side panels, each of the first and second rigid side panels including a biasing member projection; and
   a rigid valve housing in fluid communication with the expandable bag, the rigid valve housing including an adjustable tidal volume control device that interfaces with the biasing member projection of each of the first and second rigid side panels to set one of a plurality of predetermined tidal volumes for the expandable bag in an uncompressed or compressed configuration, the rigid valve housing additionally including a patient breathing interface connection member.

2. The respiratory device of claim 1, wherein the adjustable tidal volume control presents a first surface of varying depth and an opposing second surface of varying depth to respectively interface with the biasing member projection of each of the first and second rigid side panels.

3. The respiratory device of claim 1, wherein the adjustable tidal volume control device is mounted to a body portion of the rigid valve housing and wherein the respiratory device further comprises:
   an adjustable Peak Inspiratory Pressure (PIP) mechanism that is maintained within the body portion; and
   an adjustable PIP control device that is independently mounted to the body portion and adjusts the PIP mechanism to provide a predetermined peak inspiratory pressure value.

4. The respiratory device of claim 3, further comprising:
   a two-way valve maintained within the body portion that allows air to move from the expandable bag in a first direction through a first portion of the two-way valve and that directs air in an opposing direction through a second portion of the two-way valve to create Positive End Expiratory Pressure (PEEP); and
   an adjustable PEEP control device that is independently mounted to the body portion and adjusts the two-way valve to provide a predetermined PEEP.

5. The respiratory device of 3, wherein the adjustable PIP control device is labeled with indicia that corresponds to established PIP standards.

6. The respiratory device of claim 1, wherein the adjustable tidal volume control device is mounted to a body portion of the rigid valve housing and wherein the respiratory device further comprises:
   a two-way valve maintained within the body portion that allows air to move from the expandable bag in a first direction through a first portion of the two-way valve and that directs air in an opposing direction through a second portion of the two-way valve to create Positive End Expiratory Pressure (PEEP); and
   an adjustable PEEP control device that is independently mounted to the body portion and adjusts the two-way valve to provide a predetermined PEEP.

7. The respiratory device of claim 6, further comprising a filter body secured to at least one of: (a) the rigid valve housing; and (b) the PEEP control device, the filter body including a bio/viral filter that filters patient exhalations exiting the respiratory device.

8. The respiratory device of claim 7, wherein the filter body includes an exhalation port that is couplable to an end-tidal $CO_2$ monitor.

9. The respiratory device of claim 7, wherein the bio/viral filter generates its own PEEP.

10. The respiratory device of claim 6, further comprising a removable PEEP lock removably secured to the main body of the rigid valve housing, wherein the PEEP lock maintains a PEEP of zero and prevents adjustment of the PEEP control device.

11. The respiratory device of claim 6, further comprising a seal intermediate the main body of the rigid valve housing and the adjustable PEEP control device.

12. The respiratory device of 1, wherein the adjustable tidal volume control device is labeled with indicia that corresponds to established standards used to determine volumes of air needed for a patient based on their length, weight, and/or age.

13. The respiratory device of claim 1, further comprising first and second hinge pins that hingedly secure the first and second rigid side panels, respectively, to the rigid valve housing.

14. The respiratory device of claim 13, wherein the biasing member projection of each of the first and second rigid side panels is positioned forward of the respective hinge pin.

15. The respiratory device of claim 1, wherein each of the first and second rigid side panels includes an expandable bag distortion prevention feature comprising at least one of: (a) contoured edges; and (b) tabs.

16. The respiratory device of claim 1, wherein the first and second rigid side panels include edges that completely enclose the expandable bag when the expandable bag is fully compressed.

17. The respiratory device of claim 1, wherein each of the first and second rigid side panels includes a stop feature that prevents over-compression of the respiratory device, the stop feature comprising at least one of:
   (a) a projecting external stop that interfaces with a ring positioned about the rigid valve housing;
   (b) an internal stop extending from an interior surface of the respective rigid side panel, the internal stop of the first and second rigid side panel opposing one another and contacting one another upon full compression of the respiratory device;
   (c) a contour edge extending outward from an upper and/or lower surface of the respective rigid side panel, the contour edge of the first and second rigid side panel opposing one another and contacting one another upon full compression of the respiratory device; and
   (d) a tab extending outward from an upper and/or lower surface of the respective rigid side panel, a portion of the tab of a respective one of the rigid side panels interfacing with a portion of the other of the rigid side panels.

18. The respiratory device of claim 17, wherein the respiratory device provides Continuous Positive Airway Pressure (CPAP) upon both: (a) compressed gas being supplied to the respiratory device via the compressed gas inlet port; and (b) the adjustable PEEP control device being engaged.

19. The respiratory device of claim 1, further comprising an inflation adjustment dial to adjust a size of an aperture through which a compressed gas and/or ambient air communicates with the expandable bag.

20. The respiratory device of claim 1, further comprising an exhaust valve and a blocking cap, the blocking cap movable between two positions including a first position where the exhaust valve is unblocked and a second position where the exhaust valve is blocked.

21. The respiratory device of claim 1, wherein each of the first and second rigid side panels includes a textured ergonomic recess for single-handed operation of the respiratory device.

\* \* \* \* \*